(12) United States Patent
Sitdikov et al.

(10) Patent No.: US 9,599,610 B2
(45) Date of Patent: *Mar. 21, 2017

(54) TARGET CAPTURE SYSTEM

(71) Applicant: NanoMR, Inc., Albuquerque, NM (US)

(72) Inventors: Ravil A. Sitdikov, Albuquerque, NM (US); Eddie W. Adams, Albuquerque, NM (US); Magdalena A. Torrance, Albuquerque, NM (US); David K. Aley, Albuquerque, NM (US); Erik J. Smith, Los Lunas, NM (US); Victor C. Esch, Albuquerque, NM (US)

(73) Assignee: DNAE Group Holdings Limited, London (GB)

( * ) Notice: Subject to any disclaimer, the term of this patent is extended or adjusted under 35 U.S.C. 154(b) by 102 days.

This patent is subject to a terminal disclaimer.

(21) Appl. No.: 14/107,315

(22) Filed: Dec. 16, 2013

(65) Prior Publication Data

US 2014/0170652 A1    Jun. 19, 2014

Related U.S. Application Data

(60) Provisional application No. 61/739,644, filed on Dec. 19, 2012.

(51) Int. Cl.

| | | |
|---|---|---|
| *C12N 1/00* | (2006.01) | |
| *G01N 33/53* | (2006.01) | |
| *C12Q 1/68* | (2006.01) | |
| *C12N 13/00* | (2006.01) | |
| *G01N 33/543* | (2006.01) | |
| *C12N 1/20* | (2006.01) | |
| *A23C 9/144* | (2006.01) | |
| *A61K 38/00* | (2006.01) | |

(52) U.S. Cl.
CPC ........ *G01N 33/54326* (2013.01); *A23C 9/144* (2013.01); *A61K 38/00* (2013.01); *C12N 1/20* (2013.01); *C12Q 1/689* (2013.01); *C12Q 1/6827* (2013.01); *C12Q 1/6883* (2013.01); *G01N 2469/00* (2013.01)

(58) Field of Classification Search
CPC ........ C12N 1/20; A61K 38/00; C12Q 1/6883; C12Q 1/6827; C12Q 1/689; A23C 9/144
See application file for complete search history.

(56) References Cited

U.S. PATENT DOCUMENTS

| | | |
|---|---|---|
| 3,970,518 A | 7/1976 | Giaever |
| 4,018,886 A | 4/1977 | Giaever |
| 4,180,563 A | 12/1979 | Fauve |
| 4,230,685 A | 10/1980 | Senyei et al. |
| 4,267,234 A | 5/1981 | Rembaum |
| 4,434,237 A | 2/1984 | Dinarello |
| 4,452,773 A | 6/1984 | Molday |
| 4,551,435 A | 11/1985 | Liberti et al. |
| 4,554,088 A | 11/1985 | Whitehead et al. |
| 4,659,678 A | 4/1987 | Forrest et al. |
| 4,677,055 A | 6/1987 | Dodin et al. |
| 4,683,195 A | 7/1987 | Mullis et al. |
| 4,683,202 A | 7/1987 | Mullis |
| 4,695,393 A | 9/1987 | Chagnon et al. |
| 4,795,698 A | 1/1989 | Owen et al. |
| 4,851,330 A | 7/1989 | Kohne |
| 4,901,018 A | 2/1990 | Lew |
| 4,925,788 A | 5/1990 | Liberti |
| 4,942,124 A | 7/1990 | Church |
| 4,988,617 A | 1/1991 | Landegren et al. |
| 5,004,699 A | 4/1991 | Winters |
| 5,047,321 A | 9/1991 | Loken et al. |
| 5,057,413 A | 10/1991 | Terstappen et al. |
| 5,089,386 A | 2/1992 | Stackebrandt et al. |
| 5,108,933 A | 4/1992 | Liberti et al. |
| 5,136,095 A | 8/1992 | Tarnowski et al. |
| 5,149,625 A | 9/1992 | Church et al. |
| 5,164,297 A | 11/1992 | Josephson et al. |
| 5,186,827 A | 2/1993 | Liberti et al. |
| 5,200,084 A | 4/1993 | Liberti et al. |
| 5,229,724 A | 7/1993 | Zeiger |
| 5,234,816 A | 8/1993 | Terstappen |

(Continued)

FOREIGN PATENT DOCUMENTS

| | | |
|---|---|---|
| CA | 2 342 047 A1 | 9/2001 |
| EP | 1 304 581 A2 | 4/2003 |

(Continued)

OTHER PUBLICATIONS

Ramadan et al., Analytica Chimica Acta, 2010; 673: 101-108.*
International Search Report issued in PCT/US2013/076649, mailed on Feb. 27, 2014.
Armenean, et al., NMR Radiofrequency Microcoil Design: Electromagnetic Simulation Usefulness, Compes Rendus Biologies, 325(4):457-463 (2002).
Armenean, et al., Solenoidal and Planar Microcoils for NMR Spectroscopy, Proc. of the 25th Annual Int. Conf. of the IEEE Eng. in Med. and Bio. Soc., Cancun, Mexico, Sep. 17, 2003, pp. 3045-3048.
Behnia and Webb, Limited-Sample NMR Using Solenoidal Microcoils, Perfluorocarbon Plugs, and Capillary Spinning, Anal. Chem., 70:5326-5331 (1998).
Byrne, et al., Antibody-Based Sensors: Principles, Problems and Potential for Detection of Pathogens and Associated Toxins, Sensors, 9:4407-4445 (2009).

(Continued)

*Primary Examiner* — Gary Nickol
*Assistant Examiner* — Lakia Tongue
(74) *Attorney, Agent, or Firm* — Brown Rudnick LLP; Thomas C. Meyers

(57) ABSTRACT

The invention generally relates to a system for isolating or separating a target from a sample. In certain aspects, processes performed by the target capture system include introducing a plurality of magnetic particles, in which a plurality of the particles include at least one binding moiety specific to a target, into a sample to form at least one target/particle complex and applying a magnetic field to isolate the magnetic particle/target complexes from the sample. The process starts at inputting a sample into the system and ends at delivering a capture target or nucleic acids of the target into a container for further analysis.

17 Claims, 19 Drawing Sheets

(56) References Cited

U.S. PATENT DOCUMENTS

| | | |
|---|---|---|
| 5,242,794 A | 9/1993 | Whiteley et al. |
| 5,254,460 A | 10/1993 | Josephson et al. |
| 5,270,163 A | 12/1993 | Gold et al. |
| 5,338,687 A | 8/1994 | Lee et al. |
| 5,342,790 A | 8/1994 | Levine et al. |
| 5,460,979 A | 10/1995 | Levine et al. |
| 5,466,574 A | 11/1995 | Liberti et al. |
| 5,494,810 A | 2/1996 | Barany et al. |
| 5,512,332 A | 4/1996 | Liberti et al. |
| 5,541,072 A | 7/1996 | Wang et al. |
| 5,583,024 A | 12/1996 | McElroy et al. |
| 5,583,033 A | 12/1996 | Terstappen et al. |
| 5,597,531 A | 1/1997 | Liberti et al. |
| 5,604,097 A | 2/1997 | Brenner |
| 5,605,805 A | 2/1997 | Verwer et al. |
| 5,622,831 A | 4/1997 | Liberti et al. |
| 5,622,853 A | 4/1997 | Terstappen et al. |
| 5,636,400 A | 6/1997 | Young |
| 5,646,001 A | 7/1997 | Terstappen et al. |
| 5,654,636 A | 8/1997 | Sweedler et al. |
| 5,660,990 A | 8/1997 | Rao et al. |
| 5,674,713 A | 10/1997 | McElroy et al. |
| 5,677,133 A | 10/1997 | Oberhardt |
| 5,681,478 A | 10/1997 | Lea et al. |
| 5,684,401 A | 11/1997 | Peck et al. |
| 5,695,934 A | 12/1997 | Brenner |
| 5,695,946 A | 12/1997 | Benjamin et al. |
| 5,698,271 A | 12/1997 | Liberti et al. |
| 5,700,673 A | 12/1997 | McElroy et al. |
| 5,741,714 A | 4/1998 | Liberti |
| 5,768,089 A | 6/1998 | Finnigan |
| 5,770,461 A | 6/1998 | Sakazume et al. |
| 5,773,307 A | 6/1998 | Colin et al. |
| 5,776,710 A | 7/1998 | Levine et al. |
| 5,795,470 A | 8/1998 | Wang et al. |
| 5,821,066 A | 10/1998 | Pyle et al. |
| 5,834,217 A | 11/1998 | Levine et al. |
| 5,840,580 A | 11/1998 | Terstappen et al. |
| 5,846,719 A | 12/1998 | Brenner et al. |
| 5,863,722 A | 1/1999 | Brenner |
| 5,866,099 A | 2/1999 | Owen et al. |
| 5,869,252 A | 2/1999 | Bouma et al. |
| 5,876,593 A | 3/1999 | Liberti et al. |
| 5,925,573 A | 7/1999 | Colin et al. |
| 5,935,825 A | 8/1999 | Nishimura et al. |
| 5,948,412 A | 9/1999 | Murphy |
| 5,955,583 A | 9/1999 | Beavo et al. |
| 5,985,153 A | 11/1999 | Dolan et al. |
| 5,993,665 A | 11/1999 | Terstappen et al. |
| 6,013,188 A | 1/2000 | Terstappen et al. |
| 6,013,532 A | 1/2000 | Liberti et al. |
| 6,060,882 A | 5/2000 | Doty |
| 6,097,188 A | 8/2000 | Sweedler et al. |
| 6,100,099 A | 8/2000 | Gordon et al. |
| 6,120,856 A | 9/2000 | Liberti et al. |
| 6,136,182 A | 10/2000 | Dolan et al. |
| 6,138,077 A | 10/2000 | Brenner |
| 6,146,838 A | 11/2000 | Williams et al. |
| 6,150,516 A | 11/2000 | Brenner et al. |
| 6,172,214 B1 | 1/2001 | Brenner |
| 6,172,218 B1 | 1/2001 | Brenner |
| 6,194,900 B1 | 2/2001 | Freeman et al. |
| 6,228,624 B1 | 5/2001 | Terstappen |
| 6,235,475 B1 | 5/2001 | Brenner et al. |
| 6,236,205 B1 | 5/2001 | Ludeke et al. |
| 6,242,915 B1 | 6/2001 | Hurd |
| 6,265,150 B1 | 7/2001 | Terstappen et al. |
| 6,287,791 B1 | 9/2001 | Terstappen et al. |
| 6,307,372 B1 | 10/2001 | Sugarman et al. |
| 6,326,787 B1 | 12/2001 | Cowgill |
| 6,348,318 B1 | 2/2002 | Valkirs |
| 6,352,828 B1 | 3/2002 | Brenner |
| 6,361,749 B1 | 3/2002 | Terstappen et al. |
| 6,361,944 B1 | 3/2002 | Mirkin et al. |
| 6,365,362 B1 | 4/2002 | Terstappen et al. |
| 6,397,094 B1 | 5/2002 | Ludeke et al. |
| 6,404,193 B1 | 6/2002 | Dourdeville |
| 6,456,072 B1 | 9/2002 | Webb et al. |
| 6,469,636 B1 | 10/2002 | Baird et al. |
| 6,487,437 B1 | 11/2002 | Viswanathan et al. |
| 6,495,357 B1 | 12/2002 | Fuglsang et al. |
| 6,512,941 B1 | 1/2003 | Weiss et al. |
| 6,514,415 B2 | 2/2003 | Hatch et al. |
| 6,551,843 B1 | 4/2003 | Rao et al. |
| 6,555,324 B1 | 4/2003 | Olweus et al. |
| 6,582,938 B1 | 6/2003 | Su et al. |
| 6,587,706 B1 | 7/2003 | Viswanathan |
| 6,594,517 B1 | 7/2003 | Nevo |
| 6,620,627 B1 | 9/2003 | Liberti et al. |
| 6,623,982 B1 | 9/2003 | Liberti et al. |
| 6,623,983 B1 | 9/2003 | Terstappen et al. |
| 6,645,731 B2 | 11/2003 | Terstappen et al. |
| 6,660,159 B1 | 12/2003 | Terstappen et al. |
| 6,696,838 B2 | 2/2004 | Raftery et al. |
| 6,700,379 B2 | 3/2004 | Peck et al. |
| 6,788,061 B1 | 9/2004 | Sweedler et al. |
| 6,790,366 B2 | 9/2004 | Terstappen et al. |
| 6,818,395 B1 | 11/2004 | Quake et al. |
| 6,822,454 B2 | 11/2004 | Peck et al. |
| 6,845,262 B2 | 1/2005 | Albert et al. |
| 6,858,384 B2 | 2/2005 | Terstappen et al. |
| 6,867,021 B2 | 3/2005 | Maes et al. |
| 6,876,200 B2 | 4/2005 | Anderson et al. |
| 6,890,426 B2 | 5/2005 | Terstappen et al. |
| 6,898,430 B1 | 5/2005 | Liberti et al. |
| 6,914,538 B2 | 7/2005 | Baird et al. |
| 6,958,609 B2 | 10/2005 | Raftery et al. |
| 7,011,794 B2 | 3/2006 | Kagan et al. |
| 7,056,657 B2 | 6/2006 | Terstappen et al. |
| 7,078,224 B1 | 7/2006 | Bitner et al. |
| 7,096,057 B2 | 8/2006 | Hockett et al. |
| 7,141,978 B2 | 11/2006 | Peck et al. |
| 7,169,560 B2 | 1/2007 | Lapidus et al. |
| 7,200,430 B2 | 4/2007 | Thomas et al. |
| 7,202,667 B2 | 4/2007 | Barbic |
| RE39,793 E | 8/2007 | Brenner |
| 7,271,592 B1 | 9/2007 | Gerald, II et al. |
| 7,274,191 B2 | 9/2007 | Park et al. |
| 7,282,180 B2 | 10/2007 | Tibbe et al. |
| 7,282,337 B1 | 10/2007 | Harris |
| 7,282,350 B2 | 10/2007 | Rao et al. |
| 7,304,478 B2 | 12/2007 | Tsuda et al. |
| 7,332,288 B2 | 2/2008 | Terstappen et al. |
| 7,345,479 B2 | 3/2008 | Park et al. |
| 7,393,665 B2 | 7/2008 | Brenner |
| 7,403,008 B2 | 7/2008 | Blank et al. |
| 7,405,567 B2 | 7/2008 | McDowell |
| 7,523,385 B2 | 4/2009 | Nguyen et al. |
| 7,537,897 B2 | 5/2009 | Brenner et al. |
| 7,544,473 B2 | 6/2009 | Brenner |
| 7,564,245 B2 | 7/2009 | Lee |
| 7,666,308 B2 | 2/2010 | Scholtens et al. |
| 7,688,777 B2 | 3/2010 | Liberti, Jr. et al. |
| 7,764,821 B2 | 7/2010 | Coumans et al. |
| 7,815,863 B2 | 10/2010 | Kagan et al. |
| 7,828,968 B2 | 11/2010 | Tibbe et al. |
| 7,863,012 B2 | 1/2011 | Rao et al. |
| 7,901,950 B2 | 3/2011 | Connelly et al. |
| 7,943,397 B2 | 5/2011 | Tibbe et al. |
| 8,067,938 B2 | 11/2011 | McDowell |
| 8,102,176 B2 | 1/2012 | Lee |
| 8,110,101 B2 | 2/2012 | Tibbe et al. |
| 8,111,669 B2 | 2/2012 | Liberti, Jr. et al. |
| 8,128,890 B2 | 3/2012 | Droog et al. |
| 8,841,104 B2* | 9/2014 | Dryga et al. ............... 435/173.9 |
| 8,889,368 B2 | 11/2014 | Barbreau et al. |
| 2001/0018192 A1 | 8/2001 | Terstappen et al. |
| 2002/0009759 A1 | 1/2002 | Terstappen et al. |
| 2002/0012669 A1 | 1/2002 | Presnell et al. |
| 2002/0098531 A1 | 7/2002 | Thacker |
| 2002/0130661 A1 | 9/2002 | Raftery et al. |
| 2002/0132228 A1 | 9/2002 | Terstappen et al. |
| 2002/0141913 A1 | 10/2002 | Terstappen et al. |
| 2002/0164629 A1 | 11/2002 | Quake et al. |

(56) References Cited

U.S. PATENT DOCUMENTS

| | | |
|---|---|---|
| 2002/0164659 A1 | 11/2002 | Rao et al. |
| 2002/0172987 A1 | 11/2002 | Terstappen et al. |
| 2003/0003441 A1 | 1/2003 | Colston et al. |
| 2003/0022231 A1 | 1/2003 | Wangh et al. |
| 2003/0054376 A1 | 3/2003 | Mullis et al. |
| 2003/0088181 A1 | 5/2003 | Gleich |
| 2003/0092029 A1 | 5/2003 | Josephson et al. |
| 2003/0129676 A1 | 7/2003 | Terstappen et al. |
| 2003/0203507 A1 | 10/2003 | Liberti et al. |
| 2003/0206577 A1 | 11/2003 | Liberti et al. |
| 2003/0222648 A1 | 12/2003 | Fan |
| 2004/0004043 A1 | 1/2004 | Terstappen et al. |
| 2004/0018611 A1 | 1/2004 | Ward et al. |
| 2004/0072269 A1 | 4/2004 | Rao et al. |
| 2004/0076990 A1 | 4/2004 | Picard et al. |
| 2004/0087032 A1 | 5/2004 | Chandler et al. |
| 2004/0101443 A1 | 5/2004 | Kagan et al. |
| 2004/0118757 A1 | 6/2004 | Terstappen et al. |
| 2004/0151629 A1 | 8/2004 | Pease et al. |
| 2005/0003464 A1 | 1/2005 | Tibbe et al. |
| 2005/0006990 A1 | 1/2005 | Williquette et al. |
| 2005/0026144 A1 | 2/2005 | Maes et al. |
| 2005/0043521 A1 | 2/2005 | Terstappen et al. |
| 2005/0069900 A1 | 3/2005 | Lentrichia |
| 2005/0079520 A1 | 4/2005 | Wu |
| 2005/0111414 A1 | 5/2005 | Liberti et al. |
| 2005/0128985 A1 | 6/2005 | Liberti et al. |
| 2005/0181353 A1 | 8/2005 | Rao et al. |
| 2005/0181463 A1 | 8/2005 | Rao et al. |
| 2005/0245814 A1 | 11/2005 | Anderson et al. |
| 2006/0024756 A1 | 2/2006 | Tibbe et al. |
| 2006/0115380 A1 | 6/2006 | Kagan et al. |
| 2006/0129327 A1 | 6/2006 | Kim et al. |
| 2006/0147901 A1 | 7/2006 | Jan et al. |
| 2006/0194192 A1 | 8/2006 | Rao et al. |
| 2006/0233712 A1 | 10/2006 | Penades et al. |
| 2006/0257847 A1 | 11/2006 | Scholtens et al. |
| 2006/0257945 A1 | 11/2006 | Masters et al. |
| 2006/0281094 A1 | 12/2006 | Squirrell et al. |
| 2007/0037173 A1 | 2/2007 | Allard et al. |
| 2007/0037231 A1 | 2/2007 | Sauer-Budge et al. |
| 2007/0090836 A1 | 4/2007 | Xiang et al. |
| 2007/0114181 A1 | 5/2007 | Li et al. |
| 2007/0116602 A1 | 5/2007 | Lee |
| 2007/0117158 A1 | 5/2007 | Coumans et al. |
| 2007/0152669 A1 | 7/2007 | Park et al. |
| 2007/0152670 A1 | 7/2007 | Park et al. |
| 2007/0154960 A1 | 7/2007 | Connelly et al. |
| 2007/0166835 A1 | 7/2007 | Bobrow et al. |
| 2007/0183935 A1 | 8/2007 | Clemmens et al. |
| 2007/0231926 A1 | 10/2007 | Ikeda |
| 2007/0296413 A1 | 12/2007 | Park et al. |
| 2008/0026451 A1 | 1/2008 | Braman et al. |
| 2008/0042650 A1 | 2/2008 | McDowell |
| 2008/0081330 A1 | 4/2008 | Kahvejian |
| 2008/0099715 A1 | 5/2008 | Adams et al. |
| 2008/0113350 A1 | 5/2008 | Terstappen |
| 2008/0199851 A1 | 8/2008 | Egan et al. |
| 2008/0204011 A1 | 8/2008 | Shoji |
| 2008/0204022 A1 | 8/2008 | Sillerud et al. |
| 2008/0272788 A1 | 11/2008 | McDowell |
| 2008/0286838 A1 | 11/2008 | Yuan et al. |
| 2008/0315875 A1 | 12/2008 | Sillerud |
| 2009/0026082 A1 | 1/2009 | Rothberg et al. |
| 2009/0061456 A1 | 3/2009 | Allard et al. |
| 2009/0061476 A1 | 3/2009 | Tibbe et al. |
| 2009/0061477 A1 | 3/2009 | Tibbe et al. |
| 2009/0127589 A1 | 5/2009 | Rothberg et al. |
| 2009/0134869 A1 | 5/2009 | Lee |
| 2009/0136946 A1 | 5/2009 | Connelly et al. |
| 2009/0146658 A1 | 6/2009 | McDowell et al. |
| 2009/0148847 A1 | 6/2009 | Kokoris et al. |
| 2009/0156572 A1 | 6/2009 | Ikeura et al. |
| 2009/0173681 A1 | 7/2009 | Siddiqi |
| 2009/0191535 A1 | 7/2009 | Connelly et al. |
| 2009/0227044 A1 | 9/2009 | Dosev et al. |
| 2009/0246796 A1 | 10/2009 | Bernard et al. |
| 2009/0256572 A1 | 10/2009 | McDowell |
| 2009/0258365 A1 | 10/2009 | Terstappen et al. |
| 2009/0286264 A1 | 11/2009 | Scholtens et al. |
| 2010/0035252 A1 | 2/2010 | Rothberg et al. |
| 2010/0068723 A1 | 3/2010 | Jovanovich et al. |
| 2010/0072994 A1 | 3/2010 | Lee et al. |
| 2010/0129785 A1 | 5/2010 | Pris et al. |
| 2010/0137143 A1 | 6/2010 | Rothberg et al. |
| 2010/0144005 A1* | 6/2010 | Bin Kingombe et al. . 435/173.9 |
| 2010/0188073 A1 | 7/2010 | Rothberg et al. |
| 2010/0197507 A1 | 8/2010 | Rothberg et al. |
| 2010/0219824 A1 | 9/2010 | Sillerud et al. |
| 2010/0225315 A1 | 9/2010 | McDowell |
| 2010/0282617 A1 | 11/2010 | Rothberg et al. |
| 2010/0282788 A1 | 11/2010 | Liberti |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0326587 A1 | 12/2010 | Kagan et al. |
| 2011/0014686 A1 | 1/2011 | Tibbe et al. |
| 2011/0018538 A1 | 1/2011 | Lee |
| 2011/0044527 A1 | 2/2011 | Tibbe et al. |
| 2011/0046475 A1 | 2/2011 | Assif et al. |
| 2011/0052037 A1 | 3/2011 | Coumans et al. |
| 2011/0059444 A1 | 3/2011 | Stromberg et al. |
| 2011/0070586 A1 | 3/2011 | Slezak et al. |
| 2011/0086338 A1 | 4/2011 | Hwang et al. |
| 2011/0091987 A1 | 4/2011 | Weissleder et al. |
| 2011/0104718 A1 | 5/2011 | Rao et al. |
| 2011/0137018 A1 | 6/2011 | Chang-Yen et al. |
| 2011/0183398 A1 | 7/2011 | Dasaratha et al. |
| 2011/0262893 A1* | 10/2011 | Dryga et al. ............. 435/5 |
| 2011/0262925 A1 | 10/2011 | Dryga et al. |
| 2011/0262926 A1 | 10/2011 | Esch et al. |
| 2011/0262927 A1 | 10/2011 | Dryga et al. |
| 2011/0262932 A1 | 10/2011 | Esch et al. |
| 2011/0262933 A1 | 10/2011 | Dryga et al. |
| 2011/0262989 A1 | 10/2011 | Clarizia et al. |
| 2011/0263833 A1 | 10/2011 | Dryga et al. |
| 2011/0300551 A1 | 12/2011 | Rao et al. |
| 2011/0300609 A1 | 12/2011 | Lim et al. |
| 2011/0301042 A1 | 12/2011 | Steinmann et al. |
| 2012/0045828 A1 | 2/2012 | Davis et al. |
| 2012/0094275 A1 | 4/2012 | Rao et al. |
| 2012/0100546 A1 | 4/2012 | Lowery, Jr. et al. |
| 2012/0112744 A1 | 5/2012 | McDowell et al. |
| 2012/0164644 A1* | 6/2012 | Neely ............... G01N 24/08 435/6.11 |
| 2013/0109590 A1 | 5/2013 | Clarizia et al. |
| 2013/0196875 A1 | 8/2013 | Neely et al. |
| 2013/0203634 A1* | 8/2013 | Jovanovich et al. ......... 506/26 |
| 2013/0316355 A1 | 11/2013 | Dryga et al. |
| 2014/0100136 A1 | 4/2014 | Clarizia et al. |
| 2014/0170021 A1 | 6/2014 | Dryga |
| 2014/0170639 A1 | 6/2014 | Norvell |
| 2014/0170640 A1 | 6/2014 | Dykes |
| 2014/0170641 A1 | 6/2014 | Macemon |
| 2014/0170652 A1 | 6/2014 | Sitdikov et al. |
| 2014/0170667 A1 | 6/2014 | Dykes et al. |
| 2014/0170669 A1 | 6/2014 | Vandervest |
| 2014/0170727 A1 | 6/2014 | Dryga et al. |
| 2014/0171340 A1 | 6/2014 | Dykes et al. |
| 2015/0212079 A1 | 7/2015 | Dryga et al. |

FOREIGN PATENT DOCUMENTS

| | | |
|---|---|---|
| EP | 2261650 A2 | 12/2010 |
| WO | 88/03957 A1 | 6/1988 |
| WO | 89/06699 A1 | 7/1989 |
| WO | 90/08841 A1 | 8/1990 |
| WO | 91/02811 A1 | 3/1991 |
| WO | 92/08805 A1 | 5/1992 |
| WO | 92/15883 A1 | 9/1992 |
| WO | 95/31481 A1 | 11/1995 |
| WO | 98/20148 A1 | 5/1998 |
| WO | 99/53320 A1 | 10/1999 |

(56) References Cited

FOREIGN PATENT DOCUMENTS

| | | |
|---|---|---|
| WO | 01/73460 A1 | 10/2001 |
| WO | 02/098364 A2 | 12/2002 |
| WO | 2005/026762 A1 | 3/2005 |
| WO | 2005106480 A1 | 11/2005 |
| WO | 2007/018601 A1 | 2/2007 |
| WO | 2007/123345 A1 | 11/2007 |
| WO | 2007/135099 A1 | 11/2007 |
| WO | 2007123342 A1 | 11/2007 |
| WO | 2008/119054 A1 | 10/2008 |
| WO | 2008/139419 A1 | 11/2008 |
| WO | 2009/048673 A2 | 4/2009 |
| WO | 2009/055587 A1 | 4/2009 |
| WO | 2009/122216 A1 | 10/2009 |
| WO | 2011/019874 A1 | 2/2011 |
| WO | 2011/133630 A1 | 10/2011 |
| WO | 2011/133632 A1 | 10/2011 |
| WO | 2011/133759 A1 | 10/2011 |
| WO | 2011/133760 A1 | 10/2011 |

OTHER PUBLICATIONS

Chapman, et al., Use of commercial enzyme immunoassays and immunomagnetic separation systems for detecting *Escherichia coli* O157 in bovine fecal samples, Applied and Environmental Microbiology, 63(7):2549-2553 (1997).
Ciobanu and Pennington, 3D Micron-scale MRI of Single Biological Cells, Solid State Nucl. Magn. Reson., 25:138-141 (2004).
Cross, et al., Choice of Bacteria in Animal Models of Sepsis, Infec. Immun. 61(7):2741-2747 (1983).
Djukovic, et al., Signal Enhancement in HPLC/Microcoil NMR Using Automated Column Trapping, Anal. Chem., 18:7154-7160 (2006).
Drancourt, et al., Diagnosis of Mediterranean Spotted Fever by Indirect Immunofluorescence of Rickettsia conorii in circulating Endothelial Cells Isolated with Monoclonal Antibody-Coated Immunomagnetic Beads, J. Infectious Diseases, 166(3):660-663, 1992.
Fan, et al., Self-assembly of ordered, robust, three-dimensional gold nanocrystal/silica arrays, Science, 304:567-571 (2004).
Fu, et al., Rapid Detection of *Escherichia coli* O157:H7 by Immunogmagnetic Separation and Real-time PCR, Int. J. Food Microbiology, 99(1):47-57, (2005).
Goding, J.W., Conjugation of antibodies with fluorochromes: modifications to the standard methods, J. Immunol. Meth., 13:215-226 (1976).
Goloshevsky, et al., Development of Low Field Nuclear Magnetic Resonance Microcoils, Rev. Sci. Inst.., 76:024101-1 to 024101-6 (2005).
Goloshevsky, et al., Integration of Biaxial Planar Gradient Coils and an RF Microcoil for NMR Flow Imaging, Meas. Sci. Technol., 16:505-512 (2005).
Grant, et al., Analysis of Multilayer Radio Frequency Microcoils for Nuclear Magnetic Resonance Spectroscopy, IEEE Trans. Magn., 37:2989-2998 (2001).
Grant, et al., NMR Spectroscopy of Single Neurons, Magn. Reson. Med., 44:19-22 (2000).
Halbach, Design of Permanent Multipole Magnets with Oriented Rare Earth Cobalt Material, Nuclear Instrum Methods, 169:1-10 (1980).
Harada, et al., Monoclonal antibody G6K12 specific for membrane-associated differentiation marker of human stratified squamous epithelia and squamous cell carcinoma, J. Oral. Pathol. Med., 22(4):1145-152 (1993).
Harlow, et al., 1988, 'Antibodies', Cold Spring Harbor Laboratory, pp. 93-117.
Hijmans, et al., An immunofluorescence procedure for the detection of intracellular immunoglobulins, Clin. Exp. Immunol., 4:457 (1969).

Hirsch, et al., Easily reversible desthiobiotin binding to streptavidin, avidin, and other biotin-binding proteins: uses for protein labeling, detection, and isolation, Anal. Biochem., 208(2):343-57 (2002).
Hoult and Richards, The Signal-to-Noise Ratio of the Nuclear Magnetic Resonance Experiment, J. Magn. Reson., 24:71-85 (1976).
Hunter, et al., Immunoassays for Clinical Chemistry, pp. 147-162, Churchill Livingston, Edinborough (1983), Forrest et al. (Hunter is the Editor).
Inai, et al., Immunohistochemical detection of an enamel protein-related epitope in rat bone at an early stage of osteogenesis, Histochemistry, 99(5):335-362 (1993).
Engvall, Enzyme immunoassay ELISA and EMIT, Meth. in Enzymol., 70:419-439 (1980).
ISR and Written Opinion in PCT/US2008/058518, mailed Jul. 7, 2008, 21 pages.
ISR and Written Opinion in PC/US2008/062473, mailed Oct. 29, 2008, 20 pages.
ISR and Written Opinion in PCT/US2008/080983, mailed Mar. 3, 2009, 14 pages.
ISR and Written Opinion in PCT/US2009/067577, mailed Feb. 5, 2010, 13 pages.
International Search Report in PCT/US2011/33184, mailed Jul. 25, 2011, 2 pages.
International Search Report in PCT/US2011/33186, mailed Jun. 22, 2011, 1 page.
ISR and Written Opinion in PCT/US2011/48447, mailed Dec. 22, 2011, 7 pages.
ISR and Written Opinion in PCT/US2011/48452, mailed Dec. 22, 2011, 7 pages.
International Search Report in PCT/US2011/33411, mailed Jun. 22, 2011, 1 page.
International Search Report in PCT/US2011/33410, mailed Jul. 19, 2011, 2 pages.
Johne, et al., *Staphylococcus aureus* exopolysaccharide in vivo demonstrated by immunomagnetic separation and electron microscopy, J. Clin. Microbiol. 27:1631-1635 (1989).
Johnson, Thermal Agitation of Electricity in Conductors, Phys. Rev., 32:97-109 (1928).
Kaittanis, et al., One-step nanoparticle mediated bacterial detection with magentic relaxation, Nano Lett., 7(2):381-383 (2007).
Lee, et al., Chip-NRM Biosensor for detection and molecular analysis of cells, Nature Medicine, 14(8):869-874 (2008).
Lund, et al., Immunomagnetic separation and DNA hybridization for detection of enterotoxigenic *Escherichia coli* in a piglet model, J. Clin. Microbiol., 29:2259-2262 (1991).
Magin, et al., Miniature Magnetic Resonance Machines, IEEE Spectrum 34(10):51-61 (1997).
Malba, et al., Laser-lathe Lithography—A Novel Method for Manufacturing Nuclear Magnetic Resonance Microcoils, Biomed. Microdev., 5:21-27 (2003).
Massin, et al., Planar Microcoil-based magnetic resonance imaging of cells, Transducers '03, The 12th Int. Conf. on Solid State Sensors, Actuators, and Microsystems, Boston, Jun. 8-12, pp. 967-970 (2003).
Massin, et al., Planar Microcoil-based Microfluidic NMR Probes, J. Magn. Reson., 164:242-255 (2003).
McDowell, et al., Operating Nanoliter Scale NMR Microcoils in a Itesla Field, J. Mag. Reson., 188(1):74-82 (2007).
Minard, et al., Solenoidal Microcoil Design, Part I: Optimizing RF Homogeneity and coil dimensions, Concepts in Magn. Reson., 13(2):128-142 (2001).
Moresi and Magin, Miniature Permanent Magnet for Table-top NMR, Concept. Magn. Res., 19B:35-43 (2003).
Mulder, et al., Characterization of two human monoclonal antibodies reactive with HLA-B12 and HLA-B60, respectively, raised by in vitro secondary immunization of peripheral blood lymphocytes, Hum. Immunol., 36 (3):186-192 (1993).
Nyquist, Thermal Agitation of Electrical Charge in Conductors, Phys. Rev., 32:110-113 (1928).
Margin, et al., High resolution microcoil 1H-NMR for mass-limited, nanoliter-volume samples, Science, 270:1967 (1995).

(56) References Cited

OTHER PUBLICATIONS

Olson et al., High-resolution microcoil NMR for analysis of mass-limited, nanoliter samples, Anal. Chem., 70:645-650 (1998).
Pappas, et al., Cellular Separations: A Review of New Challenges in Analytical Chemistry, Analytica Chimica Acta, 601 (1):26-35 (2007).
Peck, et al., Design and Analysis of Microcoils for NMR Microscopy, J. Magn. Reson. B 108:114-124 (1995).
Peck, et al., RF Microcoils patterned using microlithographic techniques for use as microsensors in NMR, Proc. 15th Ann. Int. Conf. of the IEEE, Oct. 28-31, pp. 174-175 (1993).
Perez, et al., Viral-induced self-assembly of magnetic nanoparticle allows detection of viral particles in biological media, J. Am. Chem. Soc., 125:10192-10193 (2003).
Qiu, et al., Immunomagnetic separation and rapid detection of bacteria using bioluminescence and microfluidics, Talanta, 79:787-795 (2009).
Rogers, et al., Using microcontact printing to fabricate microcoils on capillaries for high resolution proton nuclear magnetic resonance on nanoliter volumes, Appl. Phys. Lett., 70:2464-2466 (1997).
Seeber, et al., Design and Testing of high sensitivity Microreceiver Coil Apparatus for Nuclear Magnetic Resonance and Imaging, Rev. Sci. Inst., 72:2171-2179 (2001).
Seeber, et al., Triaxial Magnetic Field Gradient System for Microcoil Magnetic Resonance Imaging, Rev. Sci. Inst., 11:4263-4272 (2000).
Sillerud, et al., 1H NMR Detection of Superparamagnetic Nanoparticles at 1 T using a Microcoil and Novel Tuning Circuit, J. Magn. Reson. 181:181-190 (2006).
Skjerve, et al., Detection of Listeria monocytogenes in foods by immunomagnetic separation, Appl. Env. Microbiol., 56:3478 (1990).
Sorli, et al., Micro-spectrometer for NMR: analysis of small quantities in vitro, Meas. Sci. Technol., 15:877-880 (2004).
Stauber, et al., Rapid generation of monoclonal antibody-secreting hybridomas against African horse sickness virus by in vitro immunization and the fusion/cloning technique, J. Immunol. Methods, 161(2):157-168 (1993).
Stocker, et al., Nanoliter volume, high-resolution NMR Microspectroscopy using a 60 um planer microcoil, IEEE Trans. Biomed. Eng., 44:1122-1127 (1997).
Subramanian, et al., RF Microcoil Design for Practical NMR of Mass-Limited Samples, J. Magn. Reson., 133:227-231 (1998).
Taktak, et al., Multiparameter Magnetic Relaxation Switch Assays, Analytical Chemistry, 79(23):8863-8869 (2007).
Torensama, et al., Monoclonal Antibodies Specific for the Phase-Variant O-Acetylated Ki Capsule of *Escherichia coli*, J. Clin. Microbiol., 29(7):1356-1358 (1991).
Trumbull, et al., Integrating microfabricated fluidic systems and NMR spectroscopy, IEEE Trans. Biomed. Eng., 47 (1):3-7 (2000).
Van Bentum, et al., Towards Nuclear Magnetic Resonance (MU)-Spectroscopy and (MU)-Imaging, Analyst, Royal Society of Chemistry, London, 129(9):793-803 (2004).
Venkateswaran, et al., Production of Anti-Fibroblast Growth Factor Receptor Monoclonal Antibodies by In Vitro Immunization, Hybridoma, 11(6):729-739 (1992).
Vermunt, et al., Isolation of salmonelas by immunomagnetic separation, J. Appl. Bact., 72:112-118 (1992).
Wang and Irudayaraj, Multifunctional Magnetic-Optical Nanoparticle Probes for Simultaneous Detection, Separation, and Thermal Ablation of Multiple Pathogens, Small, 6(2):283-289 (2010).
Webb and Grant, Signal-to-Noise and Magnetic Susceptibility Trade-offs in Solenoidal Microcoils for NMR, J. Magn. Reson. B, 113:83-87 (1996).
Wensink, et al., High Signal to Noise Ratio in Low-field NMR on a Chip: Simulations and Experimental Results, 17th IEEE MEMS, 407-410 (2004).
Williams and Wang, Microfabrication of an electromagnetic power micro-relay using SU-8 based UV-LIGA technology, Microsystem Technologies, 10(10):699-705 (2004).
Wu, et al., 1H-NMR Spectroscopy on the Nanoliter Scale for Static and On-Line Measurements, Anal. Chem., 66:3849 (1994).
Zhao, et al., A rapid bioassay for single bacterial cell quantitation using bioconjugated nanoparticles, PNAS, 101 (42):15027-15032 (2004).
Zordan, et al., Detection of Pathogenic *E. coli* O157:H7 by a Hybrid Microfluidic SPR and Molecular Imaging Cytometry Device, Cytometry A, 75A:155-162 (2009).
Extended European Search Report, issued on Oct. 15, 2013 for EP application No. 11772606.7.
Chungang Wang et al. "Multifunctional Magnetic-OPtical Nanoparticle Probes for Simultaneous Detection, Separation, and Thermal Ablation of Multiple Pathogens", Small, vol. 6, No. 2 Jan. 18, 2010, pp. 283-289.
Madonna A J, et al. "Detection of Bacteria from Biological Mixtures Using Immunomagnetic Separation Combined with Matrix-Assisted Laser Desorption/Ionization Time-of-flight Mass Spectrometry", Rapid Communications in Mass Spectrometry, John Wiley & Sons, GB, vol. 15, No. 13, Jan. 1, 2001, pp. 1068-1074.
Extended European Search Report issued in EP 11864030.9, mailed on Aug. 20, 2014.
Fung, M-C., et al. PCR amplification of mRNA directly from a crude cell lysate prepared by thermophilic protease digestion, Nucleic Acids Research, vol. 19 (15), p. 4300, 1991.
Dynabeads® for Immunoassay IVD, retrieved from http://www.invitrogen.com/site/i3s/en/home/Products-and-Services/Applications/DiagnosticsClinical-Research/Bead-based-IVD-Assavs/Bead-based-Immunoassav-iVD.html on May 29, 2013, four pages).
Burtis et al. (Burtis, C.A. (Ed.), Tietz Textbook of Clinical Chemistry, 3rd Edition (1999), W.B. Saunders Company, Philadelphia, PA, pp. 1793-1794).
Cooper et al., 2011, A micromagnetic flux concentrator device for isolation and visualization of pathogens. 15th International Conference on Miniaturized Systems for Chemistry and Life Sciences. Oct. 2-6, 2011, Seattle, Washington, USA.
Griffiths et al., 1994, Isolation of high affinity human antibodies directly from large synthetic repertoires. EMBO J. 13 (14):3245-3260.
Moreira et al., 2008, Detection of *Salmonella typhimurium* in Raw Meats using In-House Prepared Monoclonal Antibody Coated Magnetic Beads and PCR Assay of the fimA Gene. Journal of Immunoassay & Immunochemistry 29:58-69.
Yeung et al., 2002, Quantitative Screening of Yeast Surface-Displayed Polypeptide Libraries by Magnetic Bead Capture. Biotechnol. 18:212-220.
International Search Report for PCT/US2013/076649 with an International filing date of Dec. 19, 2013, 2 pages.
ISR and Written Opinion in PCT/US2008/058518, date of issuance Sep. 29, 2009, 15 pages.
Gu et al., 2003, Using Biofunctional Magentic Nanoparticles to Capture Vancomycin-Resistant Enterococci and Other Gram-Positive Bacteria at Ultralow Concentration, J. Am. Chem. Soc., 125:15702-15703.
Gu et al., 2006, Biofunctional magnetic nanoparticles for protein separation and pathogen detection, Chem. Commun.:941-949.
Heijnen et al., 2009, Method for rapid detection of viable *Escherichia coli* in water using real-time NASBA, Water Research, 43:3124-3132.
Li et al., 2010, Chemiluminescent Detect of *E. coli* O157:H7 Using Immunological Method Based on Magnetic Nanoparticles, J. of Nanoscience and Nanotechnology 10:696-701.
Sista et al., 2008, Heterogeneous Immunoassays Using Magnetic beads on a Digital Microfluidic Platform, Lab Chip 8 (2):2188-2196.
Butter et al., 2002, Synthesis and properties of iron ferrofluids, J. Magn. Magn. Mater. 252:1-3.
Lu et al., 2007, Magnetic Nanoparticles: Synthesis, Protection, Functionalization, and Application, Angew. Chem. Int. Ed. 46:1222-1244.

(56) References Cited

OTHER PUBLICATIONS

Matar et al., 1990, Magnetic particles derived from iron nitride, IEEE Transactions on magnetics 26(1):60-62.
Cold Spring Harbor Protocols, Recipe for Dulbecco's phosphate-buffered saline (Dulbecco's PBS, 2009, retrieved from http://cshprotocols.cshlp.Org/content/2009/3/pdb.rec11725. full?text_only=true on Mar. 9, 2015, one page.
Cheng et al, 2012, Concentration and detection of bacteria in virtual environmental samples based on non-immunomagnetic separation and quantum dots by using a laboratory-made system, Proc. of SPIE:82310Y-1-82310Y-18.
Ohno et al, 2011, Effects of Blood Group Antigen-Binding Adhesin Expression during Helicobacter pylori Infection of Mongolian Gerbils, The Journal of Infectious Diseases 203:726-735.
Narang et al., Methods Enzymol., 68:90 (1979).
Brown et al., Methods Enzymol., 68:109 (1979).
Myers and Gelfand, Biochemistry 30:7661-7661 (1991).
Levin, Cell 88:5-8 (1997).
Barany, F., Genome research, 1:5-16 (1991).
Margulies et al., Nature, 437: 376-380 (2005).
Olsvik_et_al_Magnetic_Seperation_Techniques_in_Diagnostic_Microbiology_Clinical_Microbiol_Rev_1994_7_43_54.
Chandler et al., Automated immunomagnetic separation and microarray detection of *E. Coli* O157:H7 from poultry carcass rinse, Int. J. Food Micro., 70 (2001) 143-154.
Bruno et al., "Development of an Immunomagnetic Assay System for Rapid Detection of Bacteria and Leukocytes in Body Fluids," J Mol Recog, 9 (1996) 474-479.
Andreassen, Jack, "One micron magnetic beads optimised for automated immunoassays" as Published in CLI Apr. 2005, retrieved from http://www.cli-online.com/uploads/tx_ttproducts/datasheet/one-micron-magnetic-beads-optimised-for-automatedimmunoassays.pdf on Dec. 28, 2015, four pages.
Safarik et al., "The application of magnetic separations in applied Microbiology" Journal of Applied Bacteriology 1995, 78, 575-585.
Dam et al. "Garlic (*Allium sativum*) Lectins Bind to High Mannose Oligosaccharide Chains", Journal of Biological Chemistry vol. 273, No. 10, Issue of Mar. 6, pp. 5528-5535, 1998.
Fenwick et al., 1986, Mechanisms Involved in Protection Provided by Immunization against Core Lipopolysaccarides of *Escherichia coli* J5 from Lethal Haemophilus pleuropneumoniae Infections in Swine, Infection and Immunity 53 (2):298-304.
Yu et al. "Development of a Magnetic Microplate Chemifluorimmunoassay for Rapid Detection of Bacteria and Toxin in Blood", Analytical Biochemistry 261 (1998), pp. 1-7.
The United States Naval Research Laboratory (NRL), "The FABS Device: Magnetic Particles", retrieved from http://www.nrl.navy.mil/chemistry/6170/6177/beads.php on Jan. 8, 2013, two pages.
Life Technologies, "Dynabeads® for Immunoassay IVD", retrieved from http://www.invitrogen.com/site/us/en/home/Productsand-Services/Applications/Diagnostics-Clinical-Research/Bead-based-IVD-Assays/Bead-based-Immunoassay-IVD.html on May 29, 2013, four pages.
Campuzano, et al., Bacterial Isolation by Lectin Modified Microengines, Nano Lett. Jan. 11, 2012; 12(1): 396-401.
Agrawal et al., 1990, Tetrahedron Letters 31:1543-46.
Harkins and Harrigan, "Labeling of Bacterial Pathogens for Flow Cytometric Detection and Enumeration" Curr Prot Cytom (2004) 11.17.1-11.17.20.
Takagi et al., Appl. Environ. Microbiol. 63:4504 (1997).
Cariello et al., Nucl Acids Res, 19:4193-4198 (1991).
Lecomte et al. Nucl Acids Res. 11:7505-7515 (1983).
Cann et al., Proc. Natl. Acad. Sci. 95:14250-14255 (1998).
Braslavsky et al., PNAS, 100:3960-3964 (2003).
Moudrianakis et al., Proc. Natl. Acad. Sci. 53:564-71 (1965).
Vandeventer, J. Clin. Microbiol. Jul. 2011, 49(7):2533-39.
Carroll, N. M., E. E. Jaeger, et al. (2000). "Detection of and discrimination between grampositive and gram-negative bacteria in intraocular samples by using nested PCR." J Clin 15 Microbiol 38(5): 1753-1757.
Klaschik, S., L. E. Lehmann, et al. (2002). "Real-time PCR for detection and differentiation of gram-positive and gram-negative bacteria" J Clin Microbiol 40(11): 4304-4307.
Chien et al., J. Bacteriol, 127:1550-1557 (1976).
Nordstrom et al., J. Biol. Chem. 256:3112-3117 (1981).
Elnifro, Elfath M., et al. "Multiplex PCR: optimization and application in diagnostic virology." Clinical Microbiology Reviews 13.4 (2000): 559-570.
Soni et al., Clin Chem 53:1996-2001 (2007).
Diaz et al., Braz J. Med. Res., 31:1239-1242 (1998).
Verma, Biochim Biophys Acta. 473:1-38 (1977).
Harris et al., Science 320:106-109 (2008).
Dover, Jason E., et al. "Recent advances in peptide probe-based biosensors for detection of infectious agents." Journal of microbiological methods 78.1 (2009): 10-19.

\* cited by examiner

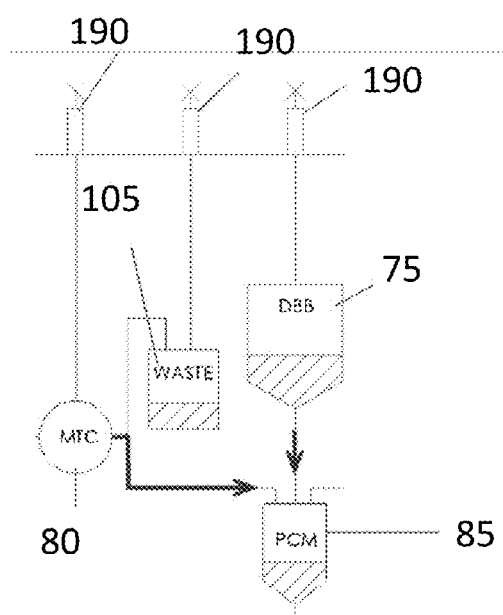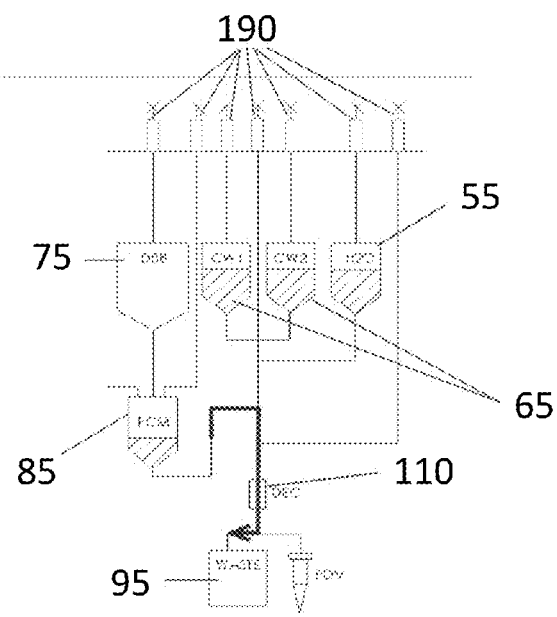
FIG 18
FIG 19

TARGET CAPTURE SYSTEM

RELATED APPLICATION

The present application claims the benefit of and priority to U.S. provisional patent application Ser. No. 61/739,644, filed Dec. 19, 2012, the content of which is incorporated by reference herein in its entirety.

TECHNICAL FIELD

This invention generally relates to cartridges for separating targets from a sample and methods related thereto.

BACKGROUND

Many laboratory and clinical procedures involve processing a sample to separate a target from the sample for subsequent identification and analysis of the target. Such processes are commonly used to detect a wide range of targets, including biological entities such as cells, viruses, proteins, bacterium, nucleic acids, etc., and have applications in clinical diagnostics, biohazard screenings, and forensic analyses.

Often there is an immediate need to identify the target, whether to determine the proper course of treatment or to develop response protocol for biohazard threat. For example, blood-borne pathogens are a significant healthcare problem because a delayed or improper diagnosis can lead to sepsis. Sepsis, a severe inflammatory response to infection, is a leading cause of death in the United States and early detection of the blood-borne pathogens underlying the infection is crucial to preventing the onset of sepsis. With early detection, the pathogen's drug/antibiotic resistant profile can be obtained which allows the clinician to determine the appropriate anti-microbial therapy for a quicker and more effective treatment.

Pathogens during active blood-borne infection or after antibiotic treatment are typically present in minute levels per mL of body fluid. Several techniques have been developed for isolation of pathogens in a body fluid sample, which include molecular detection methods, antigen detection methods, and metabolite detection methods. These conventional methods often require culturing specimens, such as performing an incubation or enrichment step, in order to detect the low levels of pathogens. The incubation/enrichment period is intended to allow for the growth of bacteria and an increase in bacterial cell numbers to more readily aid in isolation and identification. In many cases, a series of two or three separate incubations is needed to isolate the target bacteria. Moreover, enrichment steps require a significant amount of time and can potentially compromise test sensitivity by killing some of the cells sought to be measured. In certain cases, a full week may be necessary to reach the desired levels of bacteria.

The above techniques can be carried out on microfluidic devices to separate the pathogen or target from the sample. However, current microfluidic devices require extensive sample preparation prior to introducing the sample into the device for subsequent isolation. Microfluidic devices by definition are designed to conduct reactions and process at a microfluidic scale. To isolate pathogens in a microfluidic device, it is necessary to incubate/enrich the sample to expand the levels of pathogens to increase the chance that the small volume of sample introduced into the microfluidic device contains a pathogen. Alternatively, a large volume of fluid suspected of containing a pathogen is introduced at an extremely slow pace through a tube or by piecemeal pipetting the sample into the microfluidic device. These methods are equally time consuming as incubation and can result in loss of clinically relevant sample (i.e. sample with sufficient levels of targets for capture). In addition, the transfer of large volume of fluid into the microfluidic device may expose the sample to contamination.

Currently, there is no effective device capable of rapidly and effectively isolating a target that is fast and sensitive in order to provide data critical for patient treatment and biohazard analysis in a clinically relevant time frame.

SUMMARY

The invention provides a system (target capture system) that allows rapid isolation of a target analyte from a sample without the need for sample preparation or extensive manual operation. A target capture system of the invention concentrates essentially all of a clinically relevant portion of a sample (less than 1 mL) from an initial sample volume of about 10 mL. The ability to isolate small, clinically relevant, volumes of sample improves the efficiency in which nucleic acids can be extracted from a target for subsequent analysis.

The target capture systems generally include a cartridge and an instrument. The cartridge includes components such as channels, mixing chambers, and traps to process the sample for target isolation. The cartridge may interface with an instrument having one or more assemblies, such as mechanical, magnetic, pneumatic, and fluidic assemblies, that interact with the cartridge to assist/drive the processes performed on the cartridge. The target capture systems of the invention are integrated to perform several processes on a sample inputted into the cartridge to achieve a final result without user manipulation. The final result can be capture of live/whole target cells or isolation of nucleic acids from target cells within the sample.

In certain aspects, the processes performed by the target capture system include introducing a plurality of magnetic particles, in which a plurality of the particles include at least one captured moiety specific to a target, into a sample to form a mixture that includes sample and particles. The mixture is incubated to form at least one target/particle complex and a magnetic field is applied to isolate the magnetic particle/target complexes from the sample. The process starts at inputting a sample and ends at delivering a capture target (or nucleic acids of the target) into a container for further analysis.

Cartridges of the invention can include a chamber for holding and releasing the magnetic particles into a sample to form a mixture and at least one magnetic trap for receiving the sample/magnetic particle mixture. The magnetic trap engages with a magnetic assembly to isolate the magnetic particles from the sample. In certain embodiments, the cartridge includes a first magnetic trap in communication with a second magnetic trap, in which both magnetic traps engage with a magnetic assembly to isolate magnetic particles from a sample. In one embodiment, the first magnetic trap isolates magnetic particles from the sample and the isolated magnetic particles are then transferred through the second magnetic trap. The second magnetic trap engages with a second magnetic assembly to isolate the plurality of magnetic particles from the first magnetic trap. A lysing mechanism operably associated with the second magnetic trap can be used to lyse at least one target cell bound to at least one of the magnetic particles within the second magnetic trap. The cartridge may further include a matrix for receiving lysate from the first magnetic trap and retaining nucleic acid from the lysate. In one embodiment, the matrix is an affinity column. The cartridge can further include a reaction chamber, such as a bubble mixer, in communication with the matrix for pre-treating the lysate.

In one embodiment, the cartridge is for use with an instrument and the instrument includes a first magnetic assembly, a second magnetic assembly, and a lysing mechanism. The first and second magnetic assemblies generate magnetic fields to isolate magnetic particles disposed within a sample against a surface of a corresponding magnetic trap. The lysing mechanism may perform cell lysis on targets bound to the magnetic particles. The lysing mechanism can be a sonication device. Lysis can be achieved by placing the sonication against a surface of a magnetic trap and generating sonic wave to invoke cell lysis on any targets bound to the magnetic particles within the magnetic trap. The instrument can also include a drive mechanism for driving and controlling movement of the sample, the magnetic particles, and any other fluids or substances into, within, and out of the cartridge. The drive mechanism can be pneumatic, mechanical, magnetic and/or fluidic.

For isolation and detection assays conducted on cartridges or chips, it is important to transfer the entire obtained sample from a collection device into the cartridge to increase the efficiency of isolation or detection. Especially in situations where there is little sample, which is often the case in forensic analysis, or where there is a small concentration of targets per mL of sample (e.g. 1 CFU/mL), which is often the case for pathogenic detection.

Accordingly, the cartridges of the invention may include a cartridge/vessel interface designed to maximize the amount of sample transferred from the vessel and into the cartridge to avoid loss of clinically relevant sample within a sample collection vessel and/or during sample transfer. This ensures that substantially all clinically relevant sample is transferred into the cartridge and processed. The cartridge/vessel interface places the vessel containing the sample in two-way communication with the cartridge. The communication between the vessel and the cartridge can be pneumatic, fluidic, or both. In certain embodiments, the cartridge/vessel interface can include an input member and an output member. The output member introduces fluids, gases, and substances from the cartridge into the vessel and the input member transfers the sample and any introduced fluids, gases, and substances from vessel into the cartridge. Typically, the input and output members define a lumen and include a penetrating tip. The input and output members may be designed to penetrate and extend into the vessel.

In certain embodiments, the cartridge includes a cartridge/vessel interface, a chamber, and a magnetic trap. The cartridge/vessel interface couples a vessel containing a sample to the cartridge. The chamber is in communication with the cartridge/interface and can releasably hold fluid or substance for introducing the fluid or substance into the vessel. The magnetic trap is in communication with the vessel at the interface and receives the contents of the vessel. The vessel contents can include the sample and the fluid or substances introduced into the vessel from the chamber. In one embodiment, the chamber contains a plurality of magnetic particles to release into the vessel. The magnetic particles can include one or more binding moieties specific to a target within the sample. The sample and magnetic particles are transferred into the magnetic trap of the cartridge. The magnetic trap can engage with a magnetic assembly to isolate the magnetic particles from the sample.

A significant advantage of certain embodiments is that the cartridge includes both macrofluidic and microfluidic components so that the cartridge can process both macrofluidic and microfluidic volumes of fluid. This aspect of the invention accounts for the fact that a minute amount of target cells may be present in a sample having a macrofluidic volume which necessitates processing the entire macrofluidic volume in order to increase the likelihood that the target cell will be isolated. To isolate pathogens in a microfluidic device, the entire macrofluidic volume of sample would have to be transferred slowly or in a piecemeal fashion (e.g. via pipetting) into a microfluidic device at microfluidic rate, which undesirably takes a long amount of time and risks losing the target analyte of interest during the transfer. In certain aspects, the cartridge is designed to consolidate a sample of macrofluidic volume into a concentrated microfluidic volume of fluid that contains target cells of interest. The concentrated microfluidic volume is then processed at the microfluidic level.

In certain aspects, the target capture system includes a macrofluidic portion and a microfluidic portion. The macrofluidic portion includes a first magnetic trap and is configured to process a macro-scale volume of fluid including a sample, in which processing includes introducing a quantity of magnetic particles into the macro-scale volume of fluid. The microfluidic portion is in communication with the macrofluidic portion and includes a second magnetic trap. The microfluidic portion is configured to isolate a micro-scale volume of the macro-scale volume of fluid in which the micro-scale volume of fluid contains substantially the entire quantity of magnetic particles. In certain embodiments, the magnetic particles include a binding moiety specific to a target within the sample. Within the cartridge, the magnetic particles initially bind to targets in a macrofluidic volume of fluid and then the magnetic particles are concentrated into a micro-scale volume of fluid. This allows one to isolate targets initially present in a macro-scale volume into an easy to process micro-scale volume of fluid.

Magnetic particles suitable for use in the target capture system are conjugated to a capture moiety specific to a target analyte. In certain embodiments, the target capture system utilizes compositions that include a plurality of sets of magnetic particles conjugated to capture moieties to capture different targets of interest. For example, each set of the plurality of magnetic particles may be conjugated with capture moieties having different specificities for different pathogens. The capture moieties conjugated to the magnetic particles may be of the same class or different class. For example, one set of capture moieties may be antibodies specific to a first pathogen, and the other set of capture moieties may be other antibodies specific to a second pathogen. In another example, one set of capture moieties may be antibodies specific to a first pathogen, and the other set of capture moieties may be lectins specific to a second pathogen. In certain embodiments, each magnetic particle of a set is conjugated to at least two different sets of capture moieties specific to different pathogens. That is, one magnetic particle may have two or more capture moieties specific to different pathogens. The two or more capture moieties conjugated to a magnetic particle may be of the same class or different class.

BRIEF DESCRIPTION OF THE DRAWINGS

FIGS. 8-22 depict the processing steps for target capture within the cartridge of the target capture system according to certain embodiments.

DETAILED DESCRIPTION

The invention generally relates to target capture systems configured to carry out the processes necessary to isolate a target analyte from a sample without the need for sample preparation or manual operation. The target capture systems generally include a cartridge and an instrument. The cartridge includes components such as channels, reaction chamber, and reservoirs, etc. configured to perform processes for isolating a target from a sample. The cartridge interfaces with an instrument having one or more assemblies or subsystems, such as mechanical, magnetic, pneumatic, and fluidic assemblies, that interact with the cartridge to assist/drive the processes performed on the cartridge. The systems of the invention are fully integrated to perform several processes on a sample inputted into the cartridge to achieve a final result, such as live cell capture or isolated nucleic acids from a target cell, without user manipulation.

Various embodiments of the target capture system including the cartridge and the instrument and processes performed by the target capture system are described in detail below.

In certain aspects, the processes performed by the target capture systems generally include introducing a plurality of magnetic particles, in which each particle includes at least one binding moiety specific to a target, into a sample to form at least one target/particle complex and applying a magnetic field to isolate the magnetic particle/target complexes from the sample. The process starts at inputting a sample and ends at delivering a capture target (or nucleic acids of the target) into a container for further analysis.

Figure 1:
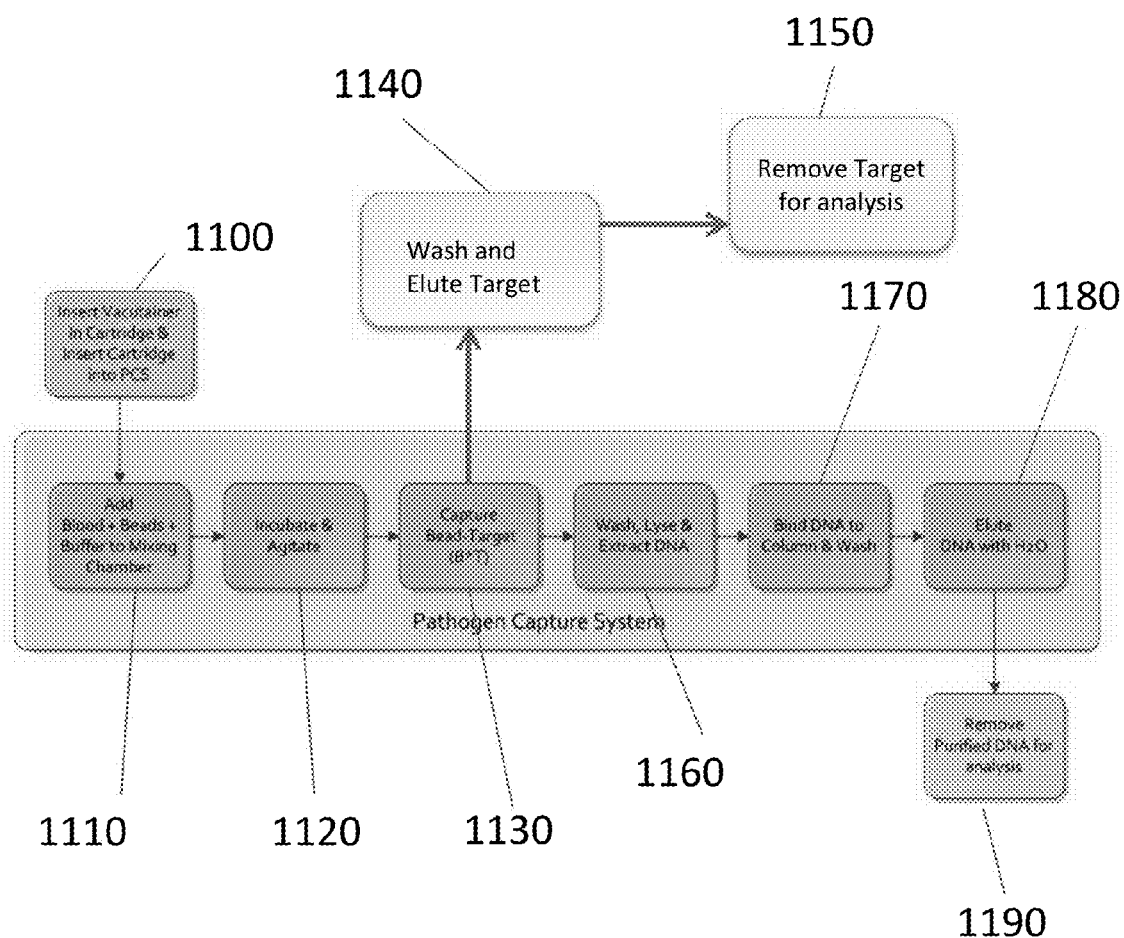
FIG. 1 outlines the processing steps of the target capture system according to certain embodiments.

FIG. 1 outlines the processing steps for isolating a target using the target capture system according to one embodiment. In step 1100, a vessel is coupled to an interface on a cartridge to place the cartridge in direct communication with the vessel. The cartridge is then loaded into the instrument. The instrument is then activated to perform the following processes. In step 1110, magnetic capture particles from the cartridge are introduced into the vessel from the cartridge through the interface. The capture particles may include binding moieties specific to a target so that targets within the sample will bind to the particles. In certain aspects, the capture particles are disposed within a fluid, such as a buffer, to facilitate introduction of the capture particles and fluid in the vessel. The sample/capture particles/fluid mixture is transferred from the vessel into the cartridge. The fluid introduced into the vessel rinses any remaining sample from the vessel. In addition, air can be introduced into the vessel to force transfer of the vessel contents (sample/fluid/particles) into the cartridge. In step 1120, the sample/particle/fluid mixture is incubated and agitated within the cartridge to form target/magnetic field complexes. In step 1130, a magnetic field is applied to capture the target/magnetic field is applied to capture the target/magnetic particles on surface of a chamber/trap of the cartridge. As in steps 1140 and 1160, the surface of the magnetic trap is then washed with a wash solution that removes any unbound sample and/or removes the bound targets from the magnetic particles. In step 1150, the target capture system elutes the target/magnetic particles complexes or targets directly into a vial for subsequent analysis. This allows one to capture, for example, the whole cell/live cell for subsequent analysis. Alternatively and in step 1160, the target capture system can continue to process the capture target to extract and isolate nucleic acids from the target. In this embodiment, the magnetic particle/target complexes are subject to a cell lysis/nucleic acid extraction step after the wash to obtain nucleic acids from the target cell. In step 1170, the resulting lysate is driven through an affinity column for capturing nucleic acids from the target cells. In step 1180, the affinity column is then eluted to drive purified nucleic acids into a vial. The vial with the isolated targets can then be removed from the target capture system by an operator for further analysis as in step 1190.

In addition to the methods of target capture described herein, the target capture system may be utilized to isolate pathogens using other methods, including the methods described in co-owned U.S. publication nos. 2011/0263833, 2011/0262925, 2011/0262932, 2011/0262933, 2011/0262926, and 2011/0262927, the entireties of which are incorporated by reference.

Sample

In certain aspects, the target capture system is designed to isolate targets from biological samples including, for example, blood, serum, plasma, buffy coat, saliva, wound exudates, pus, lung and other respiratory aspirates, nasal aspirates and washes, sinus drainage, bronchial lavage fluids, sputum, medial and inner ear aspirates, cyst aspirates, cerebral spinal fluid, stool, diarrheal fluid, urine, tears, mammary secretions, ovarian contents, ascites fluid, mucous, gastric fluid, gastrointestinal contents, urethral discharge, synovial fluid, peritoneal fluid, meconium, vaginal fluid or discharge, amniotic fluid, penile discharge, or the like may be tested. In addition, fluidic samples formed from swabs or lavages representative of mucosal secretions and epithelia are acceptable, for example mucosal swabs of the throat, tonsils, gingival, nasal passages, vagina, urethra, rectum, lower colon, and eyes, as are homogenates, lysates and digests of tissue specimens of all sorts. In addition to biological samples, samples of water, industrial discharges, food products, milk, air filtrates, and so forth are suitable for use with the target capture system. These include food, environmental and industrial samples. In certain embodiments, fluidization of a generally solid sample may be required and is a process that can readily be accomplished off-cartridge.

In certain aspects, the target capture system can process macro-scale and micro-scale volumes of fluid. Macro-scale volumes are considered volumes 1 mL and above and micro-scale volumes are considered volumes below 1 mL. The cartridge of the target capture system may be designed to directly couple to a vessel containing the sample. Vessels suitable for use with the target capture system can be macrofluidic vessels or microfluidic vessels. For example, the target capture system can process a sample from a vessel that contains fluid having a volume of 1 mL to 100 mL, preferably around 5 mL to 20 mL. Alternatively, the target capture system can process a sample from a vessel that contains a fluid having a volume of 10 to 500 µL. In one aspect, the cartridge of the target capture system is designed to couple to a 10 mL collection tube, such as a blood collection tube (e.g., VACUTAINER (test tube specifically designed for venipuncture, commercially available from Becton, Dickinson and company). However, the invention is not limited to coupling with a VACUTAINER (test tube specifically designed for venipuncture, commercially available from Becton, Dickinson and company) and can coupled with any enclosed vessel with a top that is configured to directly couple to an interface on the cartridge. The vessel and vessel/cartridge interface are described in more detail hereinafter.

Targets

The target capture system of the invention can be used to isolate any target from the sample. The target refers to the substance in the sample that will be captured and isolated by the target capture system. The target may be bacteria, fungi, a protein, a cell (such as a cancer cell, a white blood cell a virally infected cell, or a fetal cell circulating in maternal circulation), a virus, a nucleic acid (e.g., DNA or RNA), a receptor, a ligand, a hormone, a drug, a chemical substance, or any molecule known in the art.

In certain embodiments, the target is a pathogenic bacterium, fungus or both. Exemplary fungal species that may be captured by methods of the invention include species from the *Candida* genus, *Aspergillus* genus, and *Cryptococcus* genus. In particular embodiments, the specific fungal species include *C. albicans, C. glabarata, C. parasilosis, C. tropicalis, C. krusei, Cryptococcus neoformans, Cryptococcus gattii*. Exemplary bacterial species that may be captured and isolated by methods of the invention include species from the following genera *Escherichia, Listeria, Clostridium, Enterobacteriaceae, Mycobacterium, Shigella, Borrelia, Campylobacter, Bacillus, Salmonella, Enterococcus, Pneumococcus, Streptococcus, Staphylococcus, Acinetobacter, Strenotrophomonas, Pseudomanos, Neisseria, Haemophilus, Clostridium*, and *Enterococcus*. The method may also be used to detect the mecA gene, which is a bacterial gene associated with antibiotic resistance. In addition, the specific species of pathogen selected for capture and isolation may be based on a certain phenotypic characteristic. Devices and methods of the invention may be used to isolate only gram positive bacteria from a sample, or, alternatively, used to isolate only gram negative bacteria from a sample. In certain embodiments, devices and methods of the invention are used to isolate both gram positive and gram negative bacteria from a sample.

Magnetic Particles

In certain aspects, the target capture system may use magnetic particles to isolate a target from the sample. Any type of magnetic particles can be used in conjunction with the target capture system. Production of magnetic particles and particles for use with the invention are known in the art. See for example Giaever (U.S. Pat. No. 3,970,518), Senyi et al. (U.S. Pat. No. 4,230,685), Dodin et al. (U.S. Pat. No. 4,677,055), Whitehead et al. (U.S. Pat. No. 4,695,393), Benjamin et al. (U.S. Pat. No. 5,695,946), Giaever (U.S. Pat. No. 4,018,886), Rembaum (U.S. Pat. No. 4,267,234), Molday (U.S. Pat. No. 4,452,773), Whitehead et al. (U.S. Pat. No. 4,554,088), Forrest (U.S. Pat. No. 4,659,678), Liberti et al. (U.S. Pat. No. 5,186,827), Own et al. (U.S. Pat. No. 4,795,698), and Liberti et al. (WO 91/02811), the content of each of which is incorporated by reference herein in its entirety.

Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic particles. In certain embodiments, the magnetic particle is an iron containing magnetic particle. In other embodiments, the magnetic particle includes iron oxide or iron platinum.

In certain embodiments, the magnetic particles include at least about 10% superparamagnetic particles by weight, at least about 20% superparamagnetic particles by weight, at least about 30% superparamagnetic particles by weight, at least about 40% superparamagnetic particles by weight, at least about 50% superparamagnetic particles by weight, at least about 60% superparamagnetic particles by weight, at least about 70% superparamagnetic particles by weight, at least about 80% superparamagnetic particles by weight, at least about 90% superparamagnetic particles by weight, at least about 95% superparamagnetic particles by weight, or at least about 99% superparamagnetic particles by weight. In a particular embodiment, the magnetic particles include at least about 70% superparamagnetic particles by weight.

In certain embodiments, the superparamagnetic particles are less than 100 nm in diameter. In other embodiments, the superparamagnetic particles are about 150 nm in diameter, are about 200 nm in diameter, are about 250 nm in diameter, are about 300 nm in diameter, are about 350 nm in diameter, are about 400 nm in diameter, are about 500 nm in diameter, or are about 1000 nm in diameter. In a particular embodiment, the superparamagnetic particles are from about 100 nm to about 250 nm in diameter.

In certain embodiments, the particles are particles (e.g., nanoparticles) that incorporate magnetic materials, or magnetic materials that have been functionalized, or other configurations as are known in the art. In certain embodiments, nanoparticles may be used that include a polymer material that incorporates magnetic material(s), such as nanometal material(s). When those nanometal material(s) or crystal(s), such as $Fe_3O_4$, are superparamagnetic, they may provide advantageous properties, such as being capable of being magnetized by an external magnetic field, and demagnetized when the external magnetic field has been removed. This may be advantageous for facilitating sample transport into and away from an area where the sample is being processed without undue particle aggregation.

One or more or many different nanometal(s) may be employed, such as $Fe_3O_4$, FePt, or Fe, in a core-shell configuration to provide stability, and/or various others as may be known in the art. In many applications, it may be advantageous to have a nanometal having as high a saturated moment per volume as possible, as this may maximize gradient related forces, and/or may enhance a signal associated with the presence of the particles. It may also be advantageous to have the volumetric loading in a particle be as high as possible, for the same or similar reason(s). In order to maximize the moment provided by a magnetizable nanometal, a certain saturation field may be provided. For example, for $Fe_3O_4$ superparamagnetic particles, this field may be on the order of about 0.3 T.

The size of the nanometal containing particle may be optimized for a particular application, for example, maximizing moment loaded upon a target, maximizing the number of particles on a target with an acceptable detectability, maximizing desired force-induced motion, and/or maximizing the difference in attached moment between the labeled target and non-specifically bound targets or particle aggregates or individual particles. While maximizing is referenced by example above, other optimizations or alterations are contemplated, such as minimizing or otherwise desirably affecting conditions.

In an exemplary embodiment, a polymer particle containing 80 wt % $Fe_3O_4$ superparamagnetic particles, or for example, 90 wt % or higher superparamagnetic particles, is produced by encapsulating superparamagnetic particles with a polymer coating to produce a particle having a diameter of about 250 nm.

Binding Moiety

Magnetic particles for use with the target capture system can have a target-specific binding moiety (capture moiety) that allows for the particles to specifically bind the target of interest in the sample. The capture moiety may be any molecule known in the art and will depend on the target to be captured and isolated. In certain embodiments, the target capture system utilizes compositions that include a plurality of sets of magnetic particles conjugated to capture moieties specific to different targets of interest. Compositions of magnetic particles for isolating pathogens in heterogeneous samples are described in more detail in co-owned U.S. publication no. 2011/0263833 and 2011/0262925, as well co-owned U.S. provisional app. No. 61/739,616, filed Dec. 19, 2012.

The one or more different sets of magnetic particles may be coupled to one or more classes of capture moieties. Exemplary classes of capture moieties include oligonucleotides (including nucleic acid probes), proteins, ligands, lectins, antibodies, aptamers, bactertiophages, host innate immunity biomarkers (e.g., CD14), host defense peptides (e.g., defensins), bacteriocins (e.g., pyocins), and receptors. The capture moiety may be specific to a certain species within a genus of pathogen, or the capture moiety may be generally specific to several species within or the entire genus of pathogen. A class of capture moieties may include one or more different types of that class, e.g. an antibody specific to one pathogen and an antibody specific to another pathogen. In addition, one set of magnetic particles may be conjugated to a class of capture moieties that are different from a class of capture moieties conjugated to another set. For example, one set of magnetic particles may be conjugated to an antibody specific to a pathogen and another set of magnetic particles may be conjugated to a lectin specific to a different pathogen. The classes and types of capture moieties utilized will depend on the target to be captured and isolated.

In certain embodiments, each magnetic particle of a set is conjugated to at least two different sets of capture moieties specific to different pathogens. That is, one magnetic particle may have two or more capture moieties specific to different pathogens. The two or more capture moieties conjugated to a magnetic particle may be of the same class or different class. For example, a magnetic particle may have two or more antibodies specific to different pathogens. In another example, a magnetic particle may be conjugated to an antibody specific to a pathogen and a lectin specific to a different pathogen.

In particular embodiments, the capture moiety is an antibody, such as an antibody that binds a particular pathogen. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such the target bacteria, effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

Polyclonal antibodies, monoclonal antibodies, or both can be conjugated to magnetic particles in accordance with compositions and methods of the invention. Polyclonal antibodies are antibodies that are secreted by different B cell lineages, and are a collection of immunoglobulin molecules that react against a specific antigen, each identifying a different eptitope. Thus, polyclonal antibodies recognize multiple epitopes on any one antigen. Polyclonal antibodies are useful in identifying homologous pathogens, and allow for general isolation and capture of a range of species. In contrast, monoclonal antibodies are constructive from one cell line, and recognize only one epitope on an antigen. Monoclonal antibodies are more specific, and typically only bind to the epitope of the specific target cell (e.g. less likely to bind to a range of species).

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Any antibody or fragment thereof having affinity and specific for the bacteria of interest is within the scope of the invention provided herein. Immunomagnetic particles against *Salmonella* are provided in Vermunt et al. (J. Appl. Bact. 72:112, 1992). Immunomagnetic particles against *Staphylococcus aureus* are provided in Johne et al. (J. Clin. Microbiol. 27:1631, 1989). Immunomagnetic particles against *Listeria* are provided in Skjerve et al. (Appl. Env. Microbiol. 56:3478, 1990). Immunomagnetic particles against *Escherichia coli* are provided in Lund et al. (J. Clin. Microbiol. 29:2259, 1991).

In certain embodiments, the target-specific binding moiety is a lectin. Lectins are sugar-binding proteins that are highly specific for their sugar moieties. Exemplary lectins that may be used as target-specific binding moieties include Concanavalin (ConA), Wheat Germ Extract WGA). Lectins that specifically bind to bacteria and fungi are known, see, e.g. Stoddart, R. W., and B. M. Herbertson. "The use of fluorescein-labelled lectins in the detection and identification of fungi pathogenic for man: a preliminary study." Journal of medical microbiology 11.3 (1978): 315-324; and U.S. Pat. No. 5,004,699. In addition, other lectins that have pathogen-binding properties are shown in Table 1 below.

TABLE 1

Lectins with Carbohydrate Specificity

| Lectin | Source | Carbohydrate Specificity |
|---|---|---|
| AMA | *Arum maculatum* (AMA) from 'lords and ladies' flower | Mannose |
| ASA | *Allium sativum* (ASA) from garlic | Mannose |
| Con-A | *Canavalia ensiformis* (Con-A) from jack bean | α-D-Mannose, α-D-Glucose, branched mannose |
| GS-II | *Griffonia simplicoflia* (GS-II) from shrub GS | Terminal α- or β-N-Acetylglucosamine |
| HHA | *Hippeastrum* hybrid (HHA) from amaryllis | Mannonse (int and term residues) |
| IRA | Iris hybric (IRA) from Dutch Iris | N-Acetyl-D-Galactosamine |
| LEA | *Lycopersicon esculentum* (LEA) from tomato | β(1,4)-linked N-Acetylglucosamine |
| LPA | *Limulus polyphemus* (LPA) from horseshoe crab | Sialic Acid (N-Acetylneuraminic acid) |
| MIA | *Mangidera indica* (MIA) from mango | Exact specificity unknown |
| PAA | *Perseau americana* (PAA) from avocado | Exact specificity unknown |
| WGA | *Triticum vulgaris* (WGA) from Wheat Germ | (GlcNAc-β-(1,4)-GlcNAc)1-4>β-GlcNAc>Neu5Ac |
| WGA-S | Succinyl *Triticum vulgare* (WGA-S) from wheat germ | (GlcNAc-β-(1,4)-GlcNAc)1-4>β-GlcNAc>Neu5Ac |

Capture moieties suitable for use in methods of the invention may also include a nucleic acid ligand (aptamer). A nucleic acid ligand (aptamer) is a nucleic acid macromolecule (e.g., DNA or RNA) that binds tightly to a specific molecular target. Like all nucleic acids, a particular nucleic acid ligand may be described by a linear sequence of nucleotides (A, U, T, C and G), typically 15-40 nucleotides long. In solution, the chain of nucleotides forms intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the picomolar to low nanomolar range.

Nucleic acid ligands are generally discovered using an in vitro selection process referred to as SELEX (Systematic Evolution of Ligands by EXponential enrichment). See for example Gold et al. (U.S. Pat. No. 5,270,163). SELEX is an iterative process used to identify a nucleic acid ligand to a chosen molecular target from a large pool of nucleic acids. The process relies on standard molecular biological techniques, using multiple rounds of selection, partitioning, and amplification of nucleic acid ligands to resolve the nucleic acid ligands with the highest affinity for a target molecule.

In addition, the capture moiety may be a nucleic acid probe, typically an oligonucleotide, that specifically binds to a target nucleic acid sequence. A probe is generally a single-stranded nucleic acid sequence complementary to some degree to a nucleic acid sequence sought to be detected ("target sequence"). A probe may be labeled with a reporter group moiety such as a radioisotope, a fluorescent or chemiluminescent moiety, or with an enzyme or other ligand which can be used for detection. Standard techniques are used for nucleic acid and peptide synthesis. These molecular biological techniques may be performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y.,). Synthesis of complementary DNA is described in, for example, Nature Methods 2, 151-152 (2005) doi:10.1038/nmeth0205-151. Background descriptions of the use of nucleic acid hybridization to detect particular nucleic acid sequences are given in Kohne, U.S. Pat. No. 4,851,330 issued Jul. 25, 1989, and by Hogan et al., International Patent Application No. PCT/US87/03009, entitled "Nucleic Acid Probes for Detection and/or Quantitation of Non-Viral Organisms," both references hereby incorporated by reference herein. Hogan et al., supra, describe methods for determining the presence of a non-viral organism or a group of non-viral organisms in a sample (e.g., sputum, urine, blood and tissue sections, food, soil and water).

Reporter phages may also be used as a capture moiety. Reporter phages, such as bacteriophages, are typically genetically modified phages used to introduce a gene of interest into a host pathogen. The reporter gene incorporates detectable codes for a fluorescent or substrate dependent colorimetric marker into host pathogen, which allows for subsequent pathogen detection. Bacteriophages used for pathogen detection are described in detail in Singh, Amit, et al. "Bacteriophage based probes for pathogen detection." Analyst 137.15 (2012): 3405-3421; Dover, Jason E., et al. "Recent advances in peptide probe-based biosensors for detection of infectious agents." Journal of microbiological methods 78.1 (2009): 10-19.

Methods for attaching the target-specific binding moiety to the magnetic particle are known in the art. Coating magnetic particles with antibodies is well known in the art, see for example Harlow et al. (Antibodies, Cold Spring Harbor Laboratory, 1988), Hunter et al. (Immunoassays for Clinical Chemistry, pp. 147-162, eds., Churchill Livingston, Edinborough, 1983), and Stanley (Essentials in Immunology and Serology, Delmar, pp. 152-153, 2002). Such methodology can easily be modified by one of skill in the art to bind other types of target-specific binding moieties to the magnetic particles. Certain types of magnetic particles coated with a functional moiety are commercially available from Sigma-Aldrich (St. Louis, Mo.).

Since each set of particles is conjugated with capture moieties having different specificities for different pathogens, compositions used in methods of the invention may be provided such that each set of capture moiety conjugated particles is present at a concentration designed for detection of a specific pathogen in the sample. In certain embodiments, all of the sets are provided at the same concentration. Alternatively, the sets are provided at different concentrations. For example, compositions may be designed such that sets that bind gram positive bacteria are added to the sample at a concentration of $2 \times 10^9$ particles per/ml, while sets that bind gram negative bacteria are added to the sample at a concentration of $4 \times 10^9$ particles per/ml. Compositions used with methods of the invention are not affected by antibody cross-reactivity. However, in certain embodiments, sets are specifically designed such that there is no cross-reactivity between different antibodies and different sets.

The sets of magnetic particles may be mixed together to isolate certain fungi, bacteria, or both. These sets can be mixed together to isolate for example, *E. coli* and *Listeria*; or *E. coli, Listeria*, and *Clostridium*; or *Mycobacterium, Campylobacter, Bacillus, Salmonella*, and *Staphylococcus*, etc. One set may be specific to a certain bacterium and another set may be specific to a certain fungus. Any combination of sets may be used and compositions of the invention will vary depending on the suspected pathogen or pathogens to be isolated. In certain embodiments, compositions include two, three, four, five . . . 10, 20, etc. different sets of magnetic particles conjugated to different pathogens.

In preferred embodiments, sets of magnetic particles conjugated to capture moieties that are specific to different targets within multi-plex detection panel. For example, sets of modified magnetic particles may be chosen to isolate two or more certain pathogens. The two or more certain pathogens chosen may be causal of similar symptoms (e.g. digestive abnormalities), commonly found in the type of body fluid (e.g. stool), or pathogens common to a certain area (e.g. hospital setting). The following tables show exemplary panels of fungal (Table 2) targets and bacterial (Table 3) targets. "Sp" means a target species within a genus, and "Sp" means a target.

TABLE 2

Fungal Panels-Compositions of the invention will include capture moieties bound to magnetic particles specific to each of the targets in the panel.

| Fungi Assay | Target 1 | Target 2 | Target 3 | Target 4 | Target 5 |
|---|---|---|---|---|---|
| Panel A | Species of Candida genus | *C. albicans* | *C. glabrata* | *C. parapsilosis* (or *C. tropicalis*) | N/A |
| Panel B | Species of Candida genus | *C. albicans* | *C. glabrata* | *C. parapsilosis/ C. tropicalis* | *C. krusei* |
| Panel C | Species of Candida genus | *C. albicans* | *C. glabrata/ C. krusei* | *C. parapsilosis/ C. tropicalis* | *Cryptococcus* spp. |
| Panel D | Candida genus | *C. albicans/C. parapsilosis/ C. tropicalis* | *C. glabrata/C. krusei* | *Aspergillus* spp. | *Cryptococcus* spp. |
| Panel E | *Cryptococcus neoformans* | *C. albicans/C. parapsilosis/ C. tropicalis* | *C. glabrata/C. krusei* | *Aspergillus* spp. | *Cryptococcus gattii* |

TABLE 3

Bacteria Panels-Compositions of the invention will include capture moieties bound to magnetic particles specific to each of the targets in the panel.

| Bacteria Assay | Target 1 | Target 2 | Target 3 | Target 4 | Target 5 |
|---|---|---|---|---|---|
| Panel A- Gram Positive Panel | *S. aureus* | CoNS | mecA | *Streptococcus* sp./*Enterococcocus* sp. | N/A |
| Panel B- Gram Negative Panel | Enterobacteriaceae | *Pseudomonas aeruginosa* | *Acinetobacter* sp. | *Stenotrophomonas maltophilia* (or other GNR such as *Neisseria, Haemophilus*) | N/A |
| Panel C | *Staphylococcus* sp. | CoNS | Enterobacteriaceae | *Pseudomonas aeruginosa* | N/A |
| Panel D | *Staphylococcus* sp. | *Enterococcus* sp./*Streptococcus* sp. | *E. coli* | *Pseudomonas aeruginosa* | N/A |
| Panel E | *Staphylococcus aureus* | CoNS | *Enterococcus* sp./*Streptococcus* sp. | Enterobacteriaceae | N/A |
| Panel F | *Staphylococcus* sp. | *Enterococcus* sp./*Streptococcus* sp. | Enterobacteriaceae | *Candida* spp. | N/A |

TABLE 3-continued

Bacteria Panels-Compositions of the invention will include capture moieties bound to magnetic particles specific to each of the targets in the panel.

| Bacteria Assay | Target 1 | Target 2 | Target 3 | Target 4 | Target 5 |
|---|---|---|---|---|---|
| Panel G- Gram Positive Panel | S. aureus | CoNS | mecA | Streptococcus sp. | Enterococcocus sp. |
| Panel H- Gram Negative Panel | Enterobacteriaceae | Pseudomonas aeruginosa | Acinetobacter sp. | Stenotrophomonas maltophilia | Neisseria meningitidis |
| Panel I | Staphylococcus sp. | Enterococcus sp. | Streptococcus sp. | Enterobacteriaceae | Pseudomonas aeruginosa |
| Panel J | Staphylococcus sp. | Enterococcus sp. | Streptococcus sp. | E. coli | Pseudomonas aeruginosa |
| Panel K | Staphylococcus aureus | CoNS | Enterococcus sp./Streptococcus sp. | Enterobacteriaceae | Pseudomonas aeruginosa |
| Panel L | Staphylococcus sp. | Enterococcus sp./Streptococcus sp. | Enterobacteriaceae | Pseudomonas aeruginosa | Acinetobacter sp. |

In certain embodiments, compositions of the invention include at least one set magnetic particles conjugated to a capture moiety specific to an internal control (IC). For example, an IC detectable marker may be placed into a clinical sample suspected of containing a pathogen. For detection of the pathogen, a plurality of sets of magnetic particles are introduced to that clinical sample, in which at least one set is conjugated to a capture moiety designed to bind the IC detectable marker and one or more other sets are conjugated to capture moieties designed to bind to the suspected pathogens. When the assay is conducted to capture and isolate the pathogen, the presence or absence of the IC detectable marker indicates whether the assay properly separated the marker from the sample. That is, the introduction of a detectable marker allows one to determine whether the sets of magnetic particles conjugated to capture moieties are properly capturing or isolating the target pathogens that are present within the fluid. This is important to distinguish between a failed assay (i.e. failure to identify a target pathogen present in the sample) and a positive assay (i.e. positively determining the absence of a target pathogen). The presence of the marker indicates that the assay worked properly; and thus any detection of pathogen (or the absence of the pathogen) is accurate and not the result of a failed assay. Use of IC detectable markers is described in more detail in co-owned U.S. provisional application No. 61/739,577, filed Dec. 18, 2012. The panels listed in Tables 2 and 3 above may include the addition of an IC detectable marker inserted into the sample, and the sets of magnetic particles would include sets conjugated to capture moieties specific to targets listed in the panel as well as the internal control.

Methods of the invention that utilize the internal control involve obtaining a sample suspected of containing a pathogen and introducing a detectable maker into the sample. An assay is conducted to detect the suspected pathogen and the detectable marker in the sample using a plurality of sets of magnetic particles (as described herein). Members of at least one set of magnetic particles are conjugated to binding entity specific to a pathogen, and members of at least one set of magnetic particles are conjugated to a binding entity specific to the detectable marker. After the conducting step, the presence of absence of the marker in the sample is determined. Based on the presence or absence of the detectable marker, a determination is made about the presence or absence of targets in the sample. The presence of the marker indicates that the assay worked properly; and thus any detection of pathogen (or the absence of pathogen) is accurate and not the result of a failed assay.

Any detectable marker may be used for an internal control. In certain embodiments, the IC detectable marker may be a microbe, including a viable or nonviable microbe. In addition, the IC detectable marker can be sufficiently similar to the target such that the assay performs functionally in the same manner for the detectable marker and the target. The detectable marker may be labeled or otherwise modified to allow for their differentiation from targets originally present in the sample. For example, but not by way of limitation, the detectable marker can be genetically modified so as to express a fluorescent protein, or alternatively, the detectable marker could be pre-stained with a persistent stain to allow their differentiation from microbes that are originally present in the fluid composition. In addition, the detectable marker may be chosen based a chromogen dye specific reaction to the presence of the detectable marker.

Reagents and Buffers

The target capture system can employ reagents and buffers for carrying the processes of the target capture system. In certain aspects, the cartridge of the target capture system includes reservoirs for storing the reagents and buffers. The cartridge also includes components such as channels, valves, ect. that provide a means for delivering the reagent and buffers within the cartridge. Accordingly, each of the reagents, buffers, and fluids described below can be stored within the cartridge and delivered into the sample to carry out the various processes of the target capture system.

In certain embodiments, a buffer solution is added to the sample along with the magnetic particles to facilitate binding of the particles to targets within the sample. The buffer can be stored within a reagent reservoir within the cartridge and introduced to the sample during processing. An exemplary buffer includes Tris(hydroxymethyl)-aminomethane hydrochloride at a concentration of about 75 mM. It has been found that the buffer composition, mixing parameters (speed, type of mixing, such as rotation, shaking etc., and temperature) influence binding. It is important to maintain osmolality of the final solution (e.g., blood+buffer) to maintain high label efficiency. In certain embodiments, buffers used in devices and methods of the invention are designed to prevent lysis of blood cells, facilitate efficient binding of targets with magnetic beads and to reduce formation of bead aggregates. It has been found that the buffer solution containing 300 mM NaCl, 75 mM Tris-HCl pH 8.0 and 0.1% Tween 20 meets these design goals.

Without being limited by any particular theory or mechanism of action, it is believed that sodium chloride is mainly responsible for maintaining osmolality of the solution and for the reduction of non-specific binding of magnetic bead through ionic interaction. Tris(hydroximethyl)-aminomethane hydrochloride is a well-established buffer compound frequently used in biology to maintain pH of a solution. It has been found that 75 mM concentration is beneficial and sufficient for high binding efficiency. Likewise, Tween 20 is widely used as a mild detergent to decrease nonspecific attachment due to hydrophobic interactions. Various assays use Tween 20 at concentrations ranging from 0.01% to 1%. The 0.1% concentration appears to be optimal for the efficient labeling of bacteria, while maintaining blood cells intact.

Additionally, devices and methods of the invention employ wash solutions to reduce particle aggregation and remove unwanted sample, non-specific target entities, and buffer. Exemplary solutions include heparin, Tris-HCl, Tris-borate-EDTA (TBE), Tris-acetate-EDTA (TAE), Tris-cacodylate, HEPES (4-(2-hydroxyethyl)-1-piperazineethanesulphonic acid), PBS (phosphate buffered saline), PIPES (piperazine-N,N'-bis(2-ethanesulfonic acid), MES (2-N-morpholino)ethanesulfonic acid), Tricine (N-(Tri(hydroximethyl)methyl)glycine), and similar buffering agents. In particular embodiments, the wash solution includes heparin. For embodiments in which the body fluid sample is blood, the heparin also reduces probability of clotting of blood components after magnetic capture. These wash solutions can be contained in one or more reagent reservoirs of the cartridge and are typically introduced into a magnetic trap flow through chamber during separation of the magnetic particles.

In certain embodiments, the target capture system includes introducing a solution to invoke cell lysis in capture target cells in order to release the nucleic acid. The solution can be any suitable lysis fluid/buffer capable of lysing the cells and/or particles of interest in the fluid sample. An example of a suitable lysis buffer is 100 mM Tris/HCl, 8 M GuSCN (pH 6.4).

In addition, the target capture system may also utilize an elutant fluid to elute purified nucleic acids from a nucleic acid extraction column. The eluant fluid can be any fluid suitable for eluting purified nucleic acids from the nucleic acid extraction unit. Examples of suitable elution fluids include water and 10 mM Tris/HCl, 1 mM EDTA Na$_2$ (pH 8).

In addition, a reagent can be used that disrupts the interaction between the particle and the target cell, e.g. disrupts an antibody-antigen reaction. This reagent may be used after capture of the target/magnetic particle complexes to separate isolated whole target cells from the magnetic particles.

Cartridge

The target capture system of the invention includes a cartridge that is a single structure having one or more components (such as reagent reservoirs, magnetic traps, storage reservoirs, flow chambers, etc.) that are formed within the cartridge. These components can be connected via channels formed within the system. As such, there is no need for external tubing or other external attachments to connect the components of the cartridge.

A significant advantage of certain embodiments is that the cartridge includes both macrofluidic and microfluidic components and can process macrofluidic and microfluidic volumes of fluids to isolate a target. This aspect of the invention accounts for the fact that a minute amount of targets (such as pathogens) may be present in a sample having a macrofluidic volume which necessitates processing the entire macrofluidic volume in order to increase the likelihood that the target will be isolated. To isolate targets in a microfluidic device, the entire macrofluidic volume of sample would have to be transferred slowly or in a piecemeal fashion (e.g. via pipetting) into a microfluidic device at microfluidic rate, which undesirably takes a long amount of time and risks losing the target analyte of interest during the transfer. In certain aspects, the cartridge is designed to consolidate a sample of macrofluidic volume into a concentrated microfluidic volume of fluid that contains target cells of interest. The concentrated microfluidic volume is then processed at the microfluidic level.

Generally, microfluidics relates to small sample volumes and small channel pathways. For example, microfluidic volumes are normally below 1 mL, or on the microliter (μL) scale or smaller, for example, nL (nanoliters) and pL (picoliters). As used herein, microfluidic volumes relate to volumes less than 1 mL. In addition, microfluidics relates to small channel pathways on the micrometer scale. As used herein, microfluidic channels within systems of the invention refer to channels that have channel heights and/or widths equal to or less than 500 μm. See "Microfluidics and Nanofluidics: Theory and Selected Applications," Kleinstruer, C., John Wiley & Sons, 2013, which is incorporated by reference. The channel height or width is defined as the height or width of the path that the sample volume must pass through within the cartridge. Comparatively, macrofluidics volumes relate to volumes greater than the microliter (μL) scale, for example, sample volumes on the milliliter (mL) scale. As used herein, macrofluidic volumes are volumes of 1 mL or greater. Macrofluidic channels within systems of the invention are channels having channel heights and/or widths of greater than 500 μm.

Other macrofluidic components are chambers, reservoirs, traps, mixers, etc. Such macrofluidic components are dimensioned to hold 1 mL or more of fluid. For example, the individual volume can range without limitation from about 10 to about 50 mL. Other microfluidic components are chambers, reservoirs, traps, mixers, etc. Such microfluidic components are dimensioned to hold less than 1 mL of fluid. For example, the individual volumes can range without limitation from about 1 μL to about 500 μL.

The cartridge includes channels to facilitate transportation of substances and fluids through into, within, and out of the cartridge. The channel generally will include characteristics that facilitate control over fluid transport, e.g., structural characteristics (an elongated indentation) and/or physical or chemical characteristics (e.g. lined with a solution or substance that prevents or reduces adherence aggregation of sample/particulates) and/or other characteristics that can exert a force (e.g., a containing force) on a sample or fluid. The channels can be independent, connected, and/or networked between components of the cartridge. Some (or all) of the channels may be of a particular size or less, for example, having a dimension perpendicular to the flow of fluid to achieve a desired fluid flow rate out of one component and into another. The channels can be designed to transfer macro and micro scales of fluid.

The channels of the cartridge can connect to and interconnect the components of the cartridge. The cartridge can include one or more of the following components: through holes, slides, foil caps, alignment features, liquid and lyophilized reagent storage chambers, reagent release chambers, pumps, metering chambers, lyophilized cake reconstitution chambers, ultrasonic chambers, joining and mixing chambers, mixing elements such as a mixing paddle and other mixing gear, membrane regions, filtration regions, venting elements, heating elements, magnetic traps/chambers, reaction chambers, waste chambers, membrane regions, thermal transfer regions, anodes, cathodes, and detection regions, drives, plugs, piercing blades, valve lines, valve structures, assembly features such as o-rings, instrument interface regions, cartridge/vessel interfaces, one or more needles associated with the sample interface, optical windows, thermal windows, and detection regions. These components can have macro- or micro-volumes.

The cartridge includes at least one inlet for introducing sample into the cartridge and at least one inlet for allowing the instrument to introduce air pressure, e.g., to drive fluid flow, or to introduce fluids into the cartridge. The cartridge further includes at least one outlet to deliver a final product to the operator, e.g. a captured target or nucleic acids of a captured target into a removable vial for further analysis. In preferred embodiments, the inlet and outlet are associated with the cartridge/vessel interface of the invention described in detail hereinafter.

In one embodiment, the cartridge further includes sensing elements to determine the stage of the processes performed within the cartridge. The sensing elements can be used to gauge the flow within the cartridge and the timing for when certain subsystems of the instrument interact with the cartridge. The sensing elements include, but are not limited to, optical sensors (e.g. for monitoring the stage of processing within the chamber), timers (e.g., for determining how long a sample is in a mixing chamber or in a reaction chamber); air displacement sensors (e.g. for determining the volume of fluid within one or more chambers); temperature sensors (e.g. for determining the temperature of a reaction), bubble sensor (e.g. for detecting air and/or volume of fluid within chambers and fluid flow; pressure sensors for determining, e.g., rate of fluid flow.

In certain aspects, fluids and substances are driven into, within, and out the cartridge via one or more drive mechanisms. The drive mechanisms can be located on the cartridge itself or located on an instrument in combination with the cartridge. The drive mechanisms provide a means for fluid control within the cartridge and allows for transport of fluid and substances within the cartridge. In addition, the drive mechanisms provide a means for transferring fluids and substances between the cartridge and the vessel at the cartridge/vessel interface. In one embodiment, the drive mechanism is a part of the instrument and is operably associated with the cartridge at one or more cartridge/instrument interface. The cartridge can include a filter at the cartridge/instrument interface to prevent unwanted particles from entering the cartridge from the drive mechanism or instrument. The filter also prevents sample and other fluids from exiting the cartridge at the cartridge/instrument interface. The drive mechanisms of the instrument are discussed in more detail hereinafter.

The cartridge (whether including macrofluidic components, microfluidic components, or both) can be fabricated using a variety of methods, including without limitation, computer numerical control (CNC) techniques, traditional lithographic techniques, soft lithography, laminate technologies, hot embossing patterns, die cutting, polymer molding, combinations thereof, etc. The cartridge can be fabricated from any etchable, machinable or moldable substrate. The term machining as used herein includes, without limitation printing, stamping cutting and laser ablating.

Suitable materials for the cartridge include but are not limited to non-elastomeric polymers, elastomeric polymers, fiberglass, Teflon, polystyrene and co-polymers of styrene and other materials, polypropylene, polyethylene, polybutylene, polycarbonate, polyurethanes, TEFLON (polytetrafluoroethylene, commercially available by the DuPont company), and derivatives thereof. Preferably, the cartridge and the cartridge components are formed primarily from plastic. Plastics are cost-efficient and allow for the cartridge to be economically manufactured at a large scale. As such, the cartridge can be designed as a single use, disposable cartridge.

There are some components of the cartridge that are not plastic, and these components can be formed from, for example, metals, silicon, quartz, and glass. These components include but are not limited to surfaces, glass ampoules, filters, assembly materials (such as screws and other fasteners), electrode pins, membrane, affinity columns, and collection vials.

The cartridge can also include thin film layers that form structures/interfaces (such as walls and valves) on the cartridge, interfaces between components within the cartridge, and interfaces between the cartridge and the instrument. In one aspect, the thin film layers are for bonding fabricated components together (such as CNC components and lithographic components), sealing components together, providing conduits between components, transferring stimulation between components (e.g. capable of transferring physical or mechanical stimulation from an assembly/system on the instrument to a chamber in the cartridge), supporting elements, covering the channel, functioning as a cap and/or frangible seal for reservoirs or chambers, and performing as a valve. The thin film can be elastomeric or non-elastomeric material. In certain aspects, the thin film is a polymer or thermoplastic polymer. Exemplary polymers or thermoplastic polymers can include, but are not limited to, polymers selected from the group consisting of polymethyl methacrylate (PMMA), polycarbonate (PC), polyvinylacetate (PVAc), polystyrene (PS), polypropylene, polyethylene, polymethyl methacrylate, poly(amides), poly(butylene), poly(pentadiene), polyvinyl chloride, polycarbonate, polybutylene terephthalate, polysulfone, polyimide, cellulose, cellulose acetate, ethylene-propylene copolymer, ethylene-butene-propylene terpolymer, polyoxazoline, polyethylene oxide, polypropylene oxide, polyvinylpyrrolidone, and combinations thereof. In addition, thin film can be an elastomer, polymer blend and copolymer selected from the group consisting of poly-dimethylsiloxane (PDMS), poly(isoprene), poly(butadiene), and combinations thereof. In some embodiments, the thin film includes rubber (including silicone) alone or in combination with a polymer.

In a preferred embodiment, the cartridge is pre-assembled prior to shipment to distributors/customers. The pre-assembled cartridge may also include one or more of reagents, capture particles (including magnetic particles), lysing beads, water, and other substances/fluids pre-loaded into one or more chambers or reservoirs formed within the cartridge. The pre-assembled cartridge may be partially pre-loaded, e.g. loaded with only a portion of the components necessary to isolate a target. If pre-assembled, the cartridge can include reagents and magnetic particles specific certain isolation assays and/or specific to certain target analytes. In addition, the cartridge can include magnetic particles with binding moieties specific to a plurality of different targets to provide for isolation of a target when the suspected target is not known. See co-pending and co-assigned U.S. application Ser. No. 13/091,506 that describes compositions for isolating a target sample from a heterogeneous sample. It is also contemplated that the cartridge is partially-assembled prior to shipment to distributors/customers to allow the individual customer to load the cartridge with reagents, beads, ect. that are tailored to the analysis/identification needs of the customer.

Figure 2:
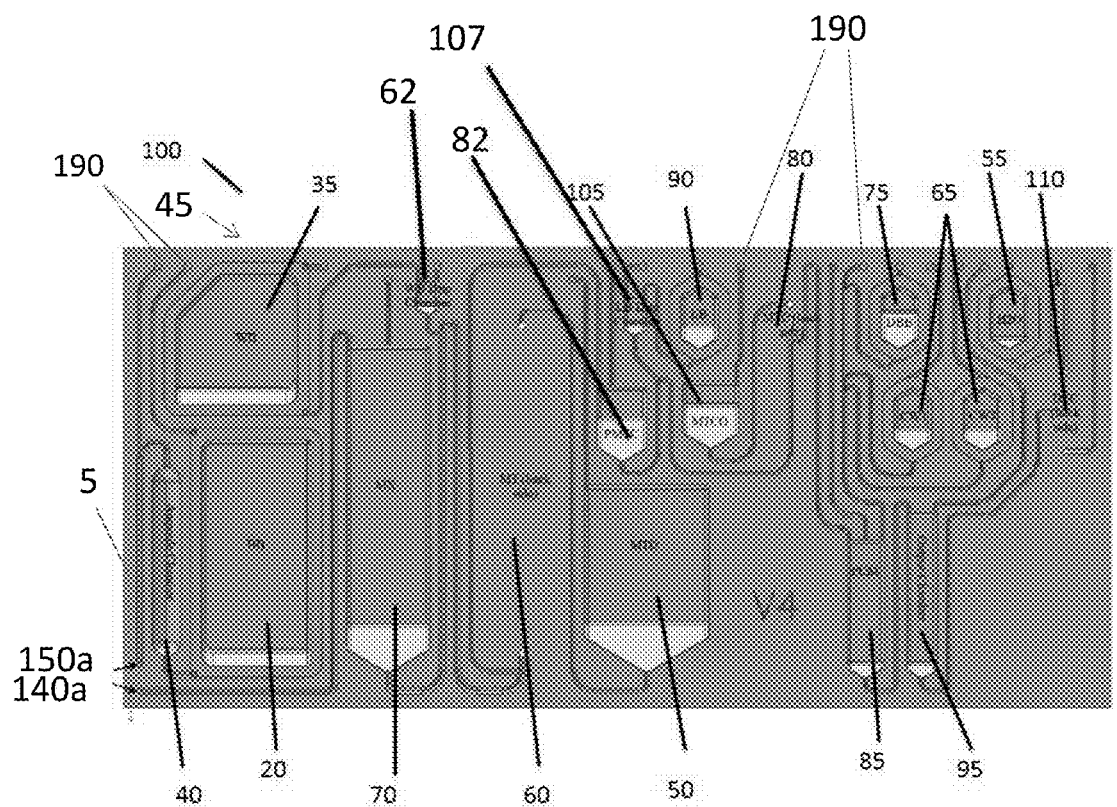
FIG. 2 depicts a schematic overview of a cartridge according to certain embodiments.
Figure 3:
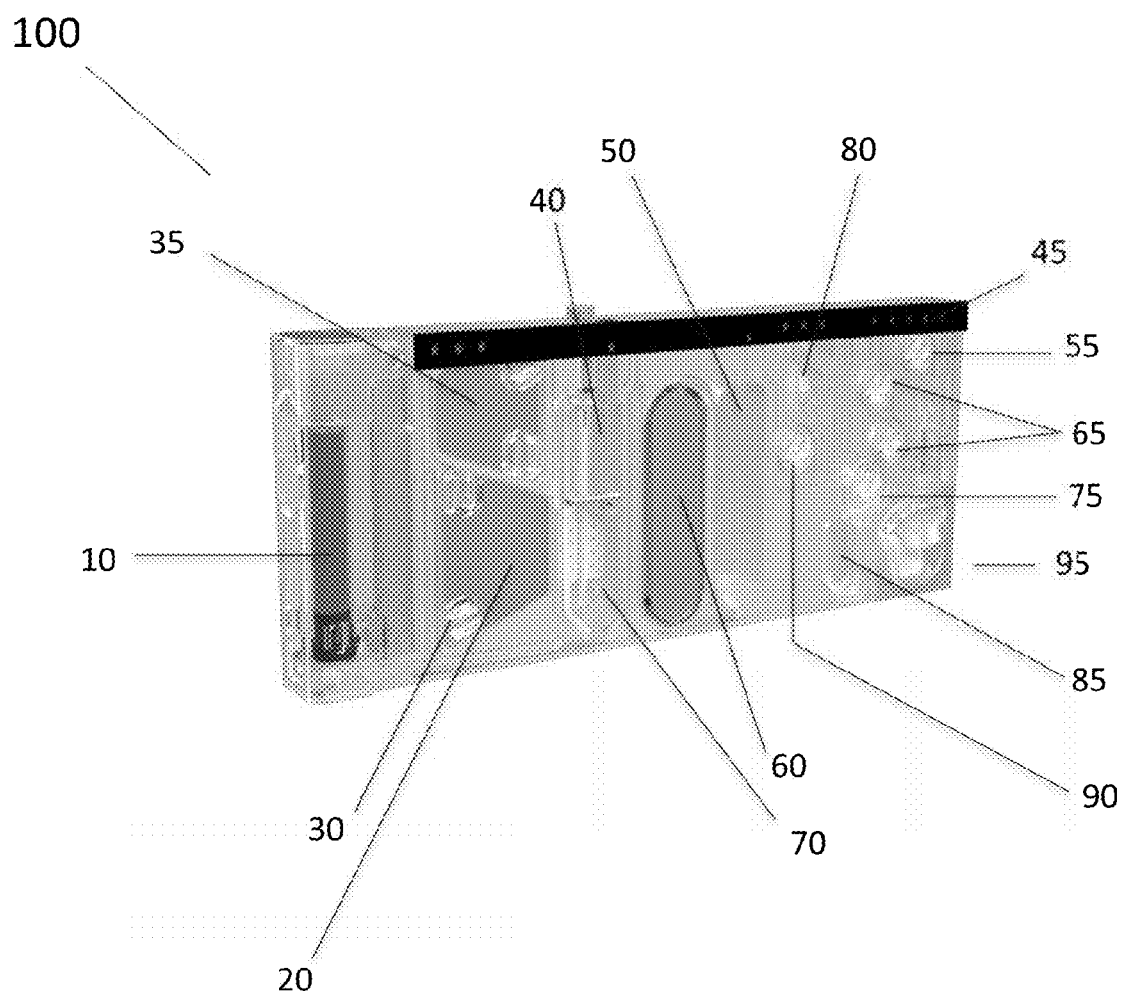
FIG. 3 depicts an external view of the cartridge according to certain embodiments.

FIG. 2 depicts a schematic overview of a cartridge 100 according to the invention. FIG. 3 depicts the various chambers as described in the schematic overview of the cartridge in FIG. 2. The cartridge 100 as depicted in FIG. 2 includes both macrofluidic and microfluidic components. However, it is understood that the cartridge could be constructed with only macrofluidic or microfluidic components. Channels, valves, and other structures are included in the cartridge to facilitate and control communication between cartridge components.

As shown in FIG. 2, the cartridge 100 includes inlet port 140a and outlet port 150a. In inlet port 140a can introduce sample or other fluids into the cartridge and outlet port 150a allows for transfer of fluid/substances/pressure out of the cartridge and into a vessel 10 containing sample. Preferably, the inlet port 140a and outlet port 150a corresponds to the cartridge/vessel interface, which includes inlet member 140 and outlet member 150 (not shown). Inlet members 140 and outlet member 150 extend to into the vessel 10 containing sample coupled to the cartridge. The outlet port 150a allows fluids/substances to be transferred out of the cartridge 100 and into a sample vessel 10. The inlet port allows transfer of sample/fluids/substances from the vessel 10 to the cartridge 100. The inlet port 140a and outlet port 150a are associated with channels within the cartridge that direct fluid flow and can also be associated with one or more valves. The valves can be used to start, stop, increase, and/or decrease fluid into the inlet port 140a and out of the outlet port 150a.

Along the top of the cartridge 100 are several drive ports 190 at the instrument interface 45. The drive ports 190 connect various features on the cartridge 100 to the instrument's 200 drive mechanism. As shown in FIG. 2, a port 190 is in communication with a particle buffer reservoir 20. The particle buffer reservoir 20 can contain a buffer that promotes binding of particles and targets. The particle buffer reservoir 20 is in communication with a particle chamber 40 containing a plurality of magnetic particles. The plurality of magnetic particles may be used to isolated one or more targets of interest. As discussed above, the plurality of magnetic particles may include different sets of magnetic particles in which each set is conjugated to capture moiety specific to a different target of interest (e.g. for multiplex capture of targets). The particle chamber 40 is typically a glass ampoule. Glass ampoules are ideal because they are able to keep the magnetic particles in a constant environment (e.g. of a certain air pressure and/or humidity). The plurality of particles within the particle chamber 40 can include moieties specific to a target. The particle buffer reservoir 20 and the particle chamber 40 are in communication with the outlet port 150a. The particles and buffer can be transported by the drive mechanism out of the outlet port 150a and directly into the vessel 10 containing a sample.

The inlet port 140a is connected to a channel that directs the contents of the vessel (sample/particle/buffer) into a mixing chamber 170. The mixing chamber 70 can be used to incubate and agitate the sample/particle/buffer mixture. The mixing chamber 70 can include a mixing paddle disposed therein. A portion of the mixing paddle is operably associated with a mechanical drive on the instrument that causes the mixing paddle to move or rotate within the mixing chamber 70.

The mixing chamber 170 is in communication with a first magnetic trap 60 and a magnetic trap overflow 50. The first magnetic trap 60, as shown in FIG. 2, is a flow through chamber in which fluid can be driven into and out of the first magnetic trap 60. The first magnetic trap 60 can be a flow chamber having a planar or orthogonal inlet. In one embodiment, the first magnetic trap 60 has an orthogonal inlet because this inlet shape creates a uniform flow profile through the magnetic trap. The magnetic trap 60 is configured to engage with a magnet assembly of the instrument 200 to separate particles from the sample/buffer via application of a magnetic field. The magnetic assembly can include an array of bar magnets which are perpendicular to a flow of fluid within the first magnetic trap 60 and have a magnetic field sufficient to force the magnetic particles against a surface of the magnetic trap, thereby separating the magnetic particles. The surface of the first magnetic trap 60 may include binding moieties specific to the magnetic particles that, in addition to the magnetic field, aid in separating magnetic particles from the sample/buffer solution. The magnetic assembly that interacts with the first magnetic trap 60 may also include a swiper magnet that generates a magnetic field to release the magnets from the surface of the magnetic trap 60 after separation. The magnetic trap overflow chamber 50 is for receiving and transferring buffer/particle/sample solution to and from the first magnetic trap 60.

As further shown in FIG. 2, the first magnetic trap 60 is in communication with a wash buffer reservoir 35. A wash buffer drip chamber 62 between the first magnet trap 60 and the wash buffer reservoir 35 can control flow of buffer into the first magnetic trap 60. The wash buffer reservoir 35 may contain buffer to rinse extra sample/buffer from magnetic particles isolated in the first magnetic trap 60. In addition, the wash buffer can be used to transfer the separated magnetic particles to the second magnetic trap 70.

Optionally, a pre-magnetic trap chamber 82 is between the first magnetic trap 60 and the second magnetic trap 80 as shown in FIG. 2. The pre-magnetic trap chamber 82 can be used to control flow of particles and wash buffer from the first magnetic trap 60 to the second magnetic trap 80. In certain aspects, the first magnetic trap 60 is macrofluidic and the second magnetic trap 80 is microfluidic. In such aspect, the pre-magnetic trap chamber 82 acts an intermediate component to aid in transitioning from macro-to-micro by controlling fluid flow from the first magnetic trap 60 and the second magnetic trap 80.

The second magnetic trap 80 is configured to engage with a magnet of the instrument to further separate any remaining sample/buffer from the magnetic particles. The second magnetic trap 80 is a flow through chamber in communication with a second magnetic trap overflow chamber 105. The second magnetic trap overflow chamber 105 is used to store unwanted buffer/sample (waste) from the second magnetic trap 80. The second magnetic trap 80 is in communication with a lysis buffer reservoir 90 and optionally, a lysis buffer drip chamber 107 to control flow of lysis buffer into the second magnetic trap 80. The second magnetic trap 80 is also configured to engage with a sonication device of the instrument. In one embodiment, a wall of the second magnetic trap 80 that interfaces with the instrument has a certain thickness, such as 125 µM, that allows vibrations of the sonication device to invoke cell lysis on targets within the second magnetic trap. The wall interfacing the sonication device can be a Mylar film. The second magnetic trap 80 can optionally include binding moieties specific to the magnetic particles to assist in isolating the magnetic particles.

The second magnetic trap 80 is also in communication with a pre-column mixer 85, which receives the lysate from the second magnetic trap 80. The pre-column mixer 85 is in communication with to a nucleic acid binding buffer reservoir and in communication with a nucleic acid extraction column 110. An output chamber 95 can be included between the pre-column mixer 85 and the nucleic acid extraction member 110. Any nucleic acid extraction member 110 that retains extracted nucleic acid while allowing the other fluids such as lysis debris to flow through the member is suitable for use in the invention. The nucleic acid extraction member 110 can be a filter or a column, such as an affinity column. Examples of nucleic acid extraction members are described in, for example, United States Patent Publication No. 2011/0300609.

One or more column wash reservoirs 65 are connected to the nucleic acid extraction member 110 to direct unwanted sample/buffer/ect. from the column 110 to a waste reservoir. An elution reservoir 55 contains a buffer or fluid that is capable of eluting nucleic acids disposed within the nucleic acid extraction member. The fluid, such as water, is flushed from the elution reservoir 55 through extraction member 110 to elute purified nucleic acids into a collection vial (not shown).

In one embodiment, the particle chamber 40, the wash buffer 35, the mixing chamber 70, the first magnetic trap 60 and the magnetic trap overflow 50 of the cartridge 100 are all macrofluidic components designed to process a macrofluidic volume of fluid. Because these components are macrofluidic, the entire sample can be subject to the incubation, agitation, and the first magnetic separation step. After the magnetic particles are isolated in the first magnetic trap 60, a wash buffer flows through the first magnetic trap 60 to transport the separated particles to the second magnetic trap 80. The cartridge 100 components after the first magnetic trap 60 are microfluidic, including the second magnetic trap 60, magnetic trap overflow 105, pre-column mixer 80. The second magnetic trap 80 isolates substantially the entire quantity of magnetic particles within a microfluidic volume of fluid from the macrofluidic volume of fluid. The rate of fluid flow between the first and second magnetic traps can be adjusted to allow for the second magnetic trap 80 to isolate all of the magnetic particles. Thus, the macrofluidic volume of sample is concentrated into a microfluidic volume of concentrated clinically relevant sample. The concentrated microfluidic volume of fluid allows for more efficient nucleic acid extraction.

Cartridge and Vessel Interface

For isolation and detection assays conducted on cartridges or chips (whether microfluidic or macrofluidic), it is important to transfer the entire obtained sample from a collection device into the cartridge to increase the efficiency of isolation or detection. Especially in situations where there is little sample, which is often the case in forensic analysis, or when there is a small concentration of targets per mL of sample (e.g. 1 CFU/mL), which is often the case for pathogenic detection. Cartridges of the invention include a cartridge/vessel interface designed to maximize the amount of sample transferred into the vessel and the amount of sample subject to the cartridge processes to avoid loss of clinically relevant within a sample collection device during sample transfer. It is understood that the cartridge/vessel interface can be included on the cartridge of the target capture system and any other cartridge for processing a sample.

The cartridge/vessel interface may include one or more input and/or output members that enter a vessel containing sample to maximize the amount of sample that is transferred from the vessel containing sample into the cartridge for processing. In one embodiment, the cartridge/sample interface includes an inlet member and an outlet member to facilitate communication of fluids and substances out of the cartridge and into the sample vessel and to facilitate communication of fluids and substances (including the sample) out of the vessel and into the cartridge. The outlet member also provides for 1) introducing air to force the sample into the cartridge via the inlet port and/or the inlet member to maximize drainage; 2) introducing a fluid into the vessel to rinse the vessel container to transfer any remaining sample in the vessel into the cartridge; and 3) introducing fluids/substances necessary for cartridge processes directly to the entire sample to ensure the entirety of the sample engages with those fluids/substances. The input member provides for transferring the vessel contents into the cartridge for processing.

In certain embodiments, the fluid is introduced into the vessel at the same time the vessel contents (including sample and/or fluid) is transferred into the cartridge. Alternatively, the sample is at least partially transferred from the vessel into the cartridge prior to introducing the fluid from the cartridge into the vessel.

In one embodiment, both the inlet member and outlet member define a lumen and include a penetrating tip. For example, the inlet member and the outlet member can be hollow pins or needles. The inlet member and outlet member correspond with inlet and outlet ports on the cartridge. The input member and output member are designed to penetrate the vessel containing the sample to place the vessel (and thus the sample) in communication with the cartridge. The communication between the vessel and the cartridge through the input members and output members may be fluidic, pneumatic, or both. The input and output members can also act to couple the vessel to the cartridge and maintain the position of the vessel on the interface.

In certain embodiments, the input and output members are in communication with a drive mechanism. The drive mechanism can be a part of the cartridge itself or located on an instrument for use with the cartridge. The drive mechanism can apply air pressure or a vacuum force to facilitate transportation between the vessel and cartridge. For example, the drive mechanism can apply air pressure through a channel of the cartridge, out of the output member, and into the vessel to force the vessel contents to drain through the input member. In addition, the drive mechanism can apply a vacuum force to the input member to force the sample to drain into member.

The input member is in communication with one or more components of the cartridge (e.g. a mixing chamber, magnetic trap, storage reservoir, reagent reservoirs, etc.) that process fluids delivered from the vessel into the cartridge. The input member allows for fluids to transfer out of the vessel and into the cartridge for processing.

The output member is in communication with one or more components of the cartridge (e.g. storage reservoir, reagent reservoir, magnetic trap, etc.) to allow delivery of fluids, substances, and/or gases from the cartridge into the vessel container. In one embodiment, fluid from a reagent reservoir is driven through the output member and into the vessel to rinse sides of the vessel. The fluid may contain one or more substances. In one aspect, the fluid includes capture particles having binding moieties specific to one or more suspected targets within the sample. The fluid can be any fluid that does not interfere with the processes of the cartridge. In another embodiment, the fluid is an essential element of the cartridge processes. For example, the fluid can be a buffer that promotes a reaction within the sample, such as promoting target capture. In addition, fluids, substances, and/or gases may be subject to a reaction/process within the cartridge prior to being delivered into the vessel. For example, a buffer may be heated in the cartridge prior to introducing the buffer into the vessel.

In certain embodiments, one or more input members and one or more output members are inserted into the vessel to place the vessel in communication with the cartridge. This allows, for example, the vessel contents to be directed through one or more input member into one or more different channels in the cartridge for processing. In addition, one or more output members may be for delivering different fluids or reagents into the vessel.

The vessel for coupling to the cartridge interface can be an open or closed container. In one embodiment, the vessel is a collection tube, such as a VACUTAINER (test tube specifically designed for venipuncture, commercially available from Becton, Dickinson and company). Ideally, the vessel is enclosed, such as a collection tube enclosed by a stopper or a plug. The stopper or plug can be rubber, silicone, or polymeric material. For coupling the vessel to the sample, the vessel or the vessel plug is pressed against the input and output member until the input and output member are inserted into the vessel. The cartridge interface can also include a vessel holder to properly position the vessel onto the needles and a locking mechanism to lock the vessel in place while coupled to the cartridge. These features provide a snug fit of the cartridge and the vessel.

Vessels suitable for use with the cartridge can be of any volume size. For example, the vessels can range in volumes from 0.1 to 1 mL to 100 mL. In one embodiment, the vessel has a volume of 10 mL. The volume of the vessel may depend on the sample and the suspected target to be detected. That is, the vessel should be of a sufficient volume to contain an amount of sample fluid in which it is more likely than not that a suspected target is present.

In an embodiment, the output member is positioned within the vessel so that the output member delivers a fluid to the top of the vessel. This causes the fluid to run down at least one side of the vessel and rinse any sample that may have collected along the side of the vessel. The drive mechanism can be set to apply a pressure sufficient to deliver the fluid out of the output member so that it hits the top surface of the vessel. In addition, the input member is positioned within the vessel to promote drainage of the vessel contents. For example, the input member is level with or below the bottom of the vessel. In one embodiment, the vessel or the vessel plug is shaped to drain into the input member. For example, the vessel plug is conically-shaped.

In addition, the drive mechanism may provide sufficient pressure to release capture particles out of the output member and into the vessel. For example, pressure from the drive mechanism releases a buffer into a chamber having a plurality of capture particles disposed therein. The buffer/capture particles are then driven from the cartridge through the output member and directly into the vessel. The drive mechanism continues to force the buffer through the particle chamber and into the vessel until all of the capture particles are transferred into the vessel. At the same time, the input member may transfer the sample, buffer, and capture particles out of the vessel and into the cartridge. After substantially all the sample and capture particles are transferred into the cartridge, fluid or the buffer can continue to be introduced into the sample for an additional rinse. In another embodiment, the input member transfers at least a portion of the sample into the cartridge prior to introduction of the capture particles/buffer to provide space within the vessel.

Figure 4:
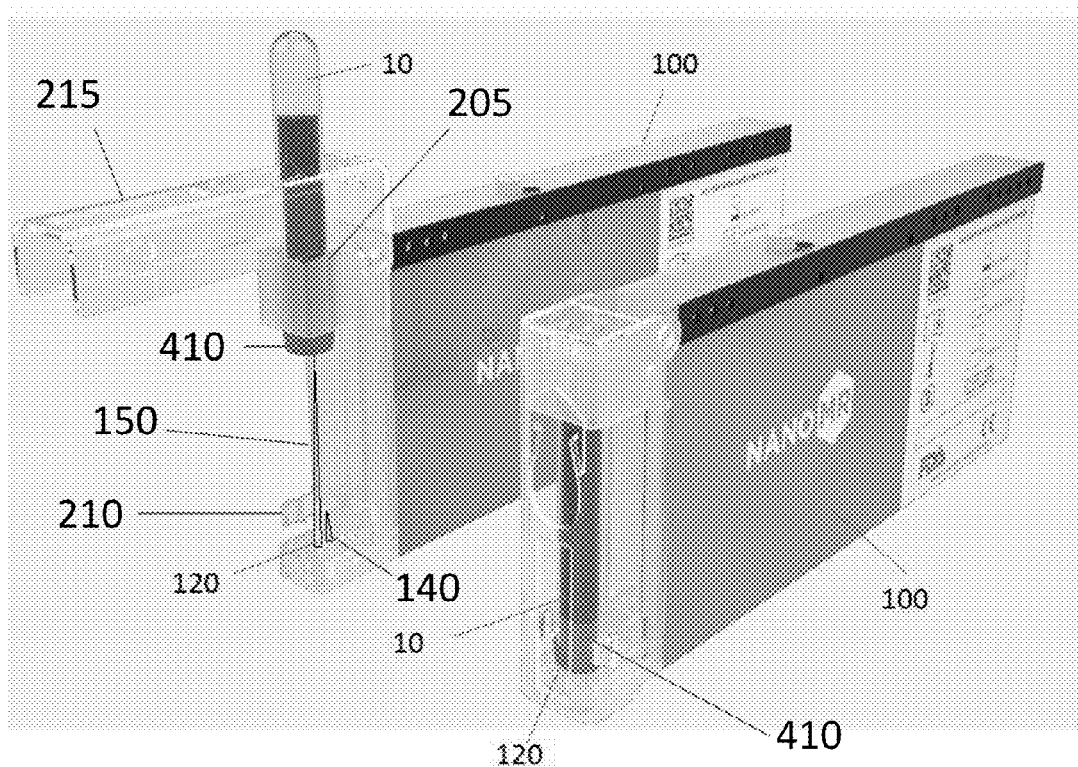
FIG. 4 depicts the cartridge/vessel interface according to certain embodiments.

FIG. 4 highlights the vessel/cartridge interface 120 of the cartridge 100. The vessel/cartridge interface couples the vessel 10 to the cartridge 100 and provides communication (including fluidic and pneumatic communication) between the cartridge and the vessel. The vessel/cartridge interface includes output member 150 and input member 140. The output member 150 and input member 140 are hollow pins or needles that penetrate the vessel 10 to place the vessel 10 in communication with the cartridge 100. The input member 140 and output member 150 penetrate a stopper 410 coupled to the vessel. The vessel/cartridge interface 120 can include guide 205. For loading, the vessel 10 is pushed through the guide 205 to direct and align the vessel 10 onto the input member 140 and output member 150. One or more positioning arms 210 are designed to hold the vessel 10 in place once positioned onto the input member 140 and output member 150. In addition, the cartridge can include a vessel cover 215 that closes over the vessel 10 as coupled to the cartridge 100.

Instrument

In certain aspects, the cartridge interfaces with and is used in conjunction with an instrument. The instrument provides, for example, the pneumatic, fluidic, magnetic, mechanical, chemical functions, as necessary to process the sample within the cartridge. In one aspect, the cartridge is inserted into the instrument for processing and the instrument is turned on by an operator to activate sample processing. Once the cartridge is loaded into the instrument, the system does not require further manual technical operations on behalf of the operator.

In one embodiment, the instrument contains drive mechanisms that connect to the cartridge when inserted into the instrument. Any drive mechanism known in the art may be used with target capture system, including pneumatic drive mechanisms, hydraulic drive mechanisms, magnetic drive systems, and fluidic drive systems. The drive mechanism provides a means for fluid control within the cartridge and allows for transport of fluid and substances between chambers. The drive mechanism can be used to initiate and control fluid flow, open valves, form bubbles (e.g. for mixing) and to initiate mechanical/chemical processes within the cartridge.

The drive mechanism can also be operably associated with a controller so that the controller engages the drive mechanism at certain stages in the pathogen capture process. The controller may engage with one or more sensors to determine when and how to activate the drive mechanism during sample processing. In certain aspects, the controller is a computing system. In certain embodiments, drive mechanism is a pneumatic. The pneumatic drive mechanism can include pumps, electromechanical valves, pressure regulators, tubing, pneumatic manifolds, flow and pressure sensors. Pneumatic drive mechanisms use air pressure and air displacement to control the flow of fluids within the cartridge. In certain aspects, the pneumatic drive mechanism is coupled to electronic regulators. When coupled to an electronic regulator, the pneumatic mechanism may be an external compressor with a reservoir for pumping compressed nitrogen, argon or air.

The instrument also includes one or more magnetic assemblies. The magnetic assemblies engage with one or more magnetic traps (typically, flow-through chambers) of the cartridge. The magnetic assemblies can include permanent magnets, removable magnets, electromagnets, or the like, or combinations thereof. The magnet assemblies may have magnets of various shapes, and of varying strengths, depending on the application thereof. If the instrument includes electromagnets, i.e. magnets that produce a magnetic field upon introduction of an electric current, the instrument may also include a current generator to activate the electromagnets. Depending on the stage of processing, the magnetic assembly includes one or magnet that are positioned against the cartridge to facilitate capture of one or more magnetic particles on a surface of a magnetic trap. Alternatively, the electromagnets can be prepositioned next to the cartridge and activated by an electric current to facilitate capture of one or more magnetic particles against the surface of the trap.

The size and strength of the magnet(s) of the magnetic assembly should produce a magnetic field suffice to force the magnetic particles within the sample against a surface of the magnetic trap of the cartridge, either macrofluidic or mircofluidic. For example, the magnetic assembly can include 7 bar NdFeB magnets that can be positioned against a magnetic trap of the cartridge. In another example, the magnet assembly includes a magnet with a magnetic flux of about 0.6 T and a magnetic gradient of about 150 T/m. This magnet's high magnetic gradient of about 150 T/m is capable of isolating a plurality of magnetic particles (for example, 1000 magnetic particles) in on a surface with a micro-scale surface area.

The instrument can also include mechanical, electrical, and thermo-electrical systems. For instance, instrument can include mechanical mechanism for engaging with a paddle mixer disposed within in a mixing chamber of the cartridge. The instrument can also include pistons and plungers to activate one or more push valves located on the cartridge. In addition, the instrument can include a heating system designed to control the temperatures of one or more components of the cartridge. For example, the instrument can include a heating apparatus operably associated with the mixing chamber to heat the chamber and encourage binding of one or more magnetic particles with targets contained within the sample. The instrument may include a control processor or a computing system to activate other subsystems, such as the drive mechanism. The control processor can be keyed into sensors designed to track the process through the cartridge. This allows the control processor to activate certain substances based on the location of the fluid within the cartridge or based upon the stage of processing.

The instrument can also include a lysing mechanism for invoking lysis of cells within the sample. The lysing mechanism can include any sonication device that is well-known in the art. In certain embodiments, the sonication device is the VCX 750 Sonicator sold under the trademark VIBRA-CELL (sonicator, commercially available from Sonics and Materials, Inc.). Generally, the probe of the sonicator is placed into the liquid containing the targets to be lysed. Electrical energy from a power source is transmitted to a piezoelectric transducer within the sonicator converter, where it is changed to mechanical vibrations. The longitudinal vibrations from the converter are intensified by the probe, creating pressure waves in the liquid. These in turn produce microscopic bubbles, which expand during the negative pressure excursion and implode violently during the positive excursion. This phenomenon, referred to as cavitation, creates millions of shock waves and releases high levels of energy into the liquid, thereby lysing the target. In another embodiment, the sonication transducer may be brought in contact with a chamber holding captured complexes by way of a structural interface. The sonication transducer vibrates structural interface, such as a thin film between the magnetic trap and the transducer, until lysis is achieved. In either method, the appropriate intensity and period of sonication can be determined empirically by those skilled in the art.

Figure 5:
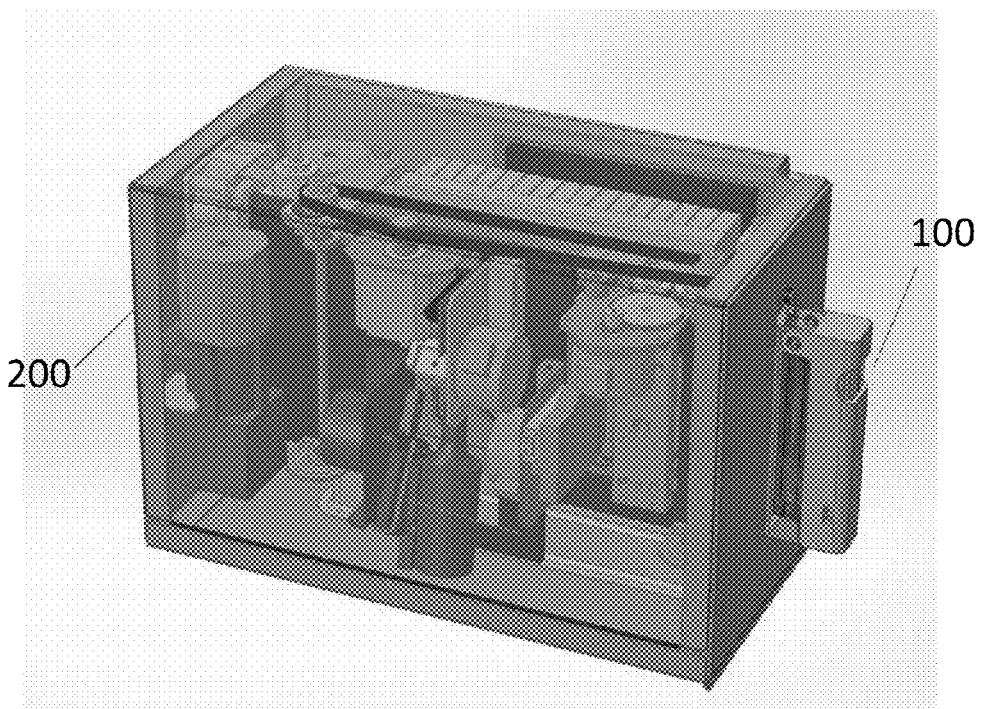
FIG. 5 depicts the instrument of the target capture system according to certain embodiments.
Figure 6:
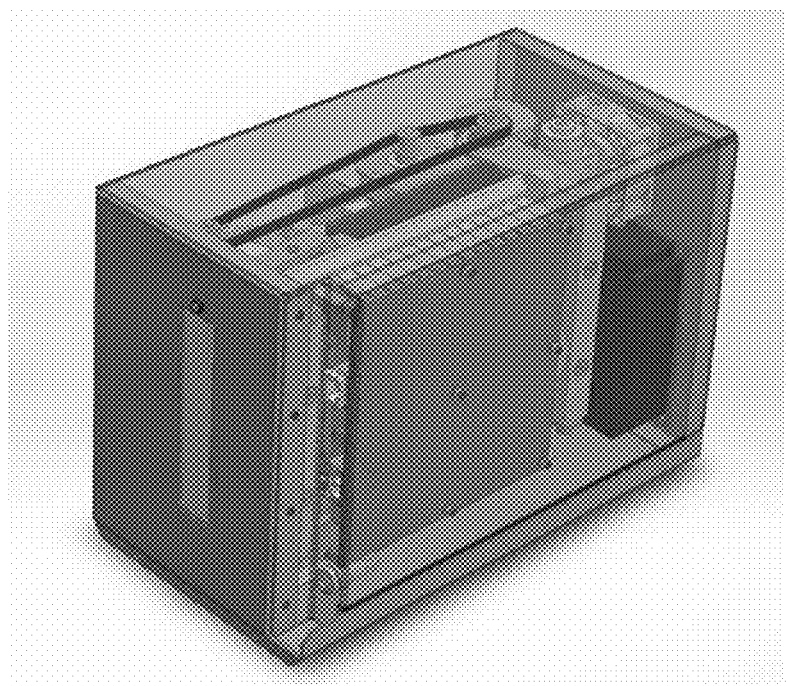
FIG. 6 depicts the instrument of the target capture system according to certain embodiments.

FIGS. 5 and 6 depict the instrument 200 of the target capture system for use with the cartridge 100. FIG. 5 depicts the cartridge 100 loaded into the instrument 200. FIG. 6 depicts the instrument 200 without a cartridge 100 loaded. The features of the instrument 200 are discussed in detail above.

Figure 7:
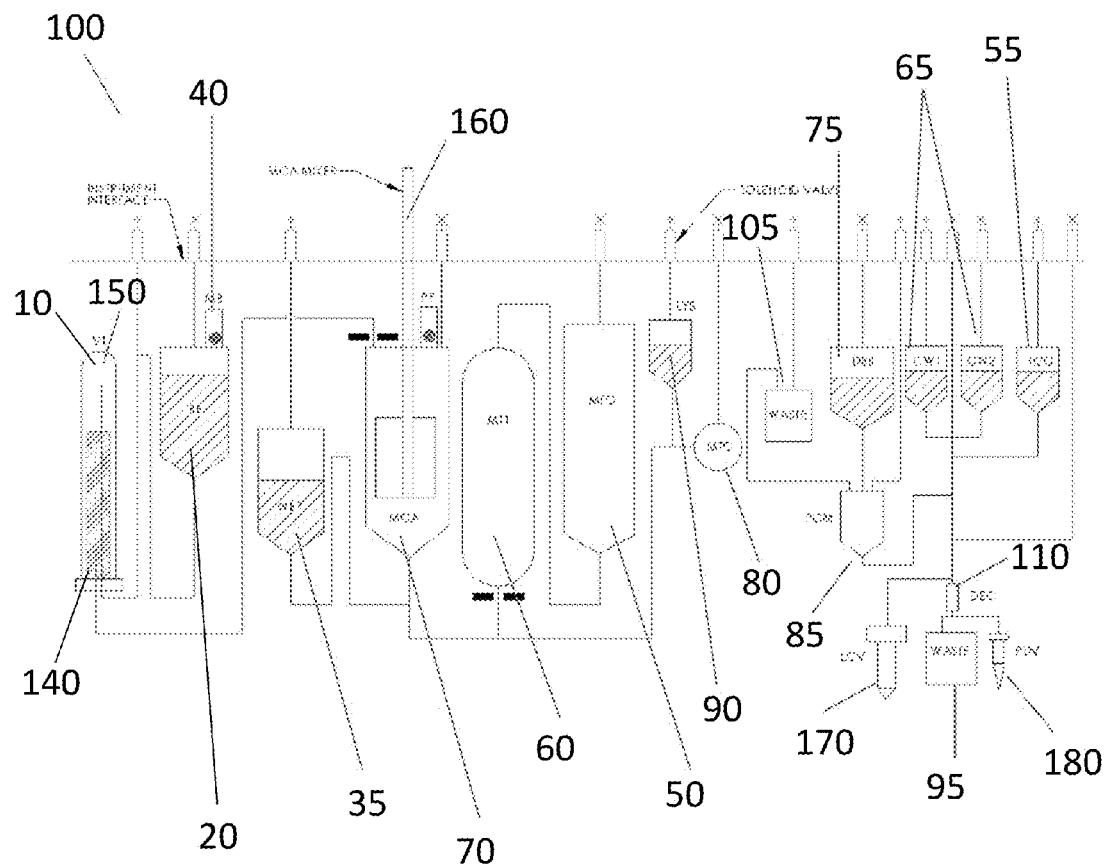
FIG. 7 depicts a schematic overview of a cartridge according to certain embodiments.

FIG. 7 depicts another schematic view of the cartridge 100 of the target capture system. FIGS. 8-23 depict the process of target capture within the target capture system as the sample is directed into and processed within the cartridge. The arrows within the figures indicate the path of fluid flow.

Figure 8:
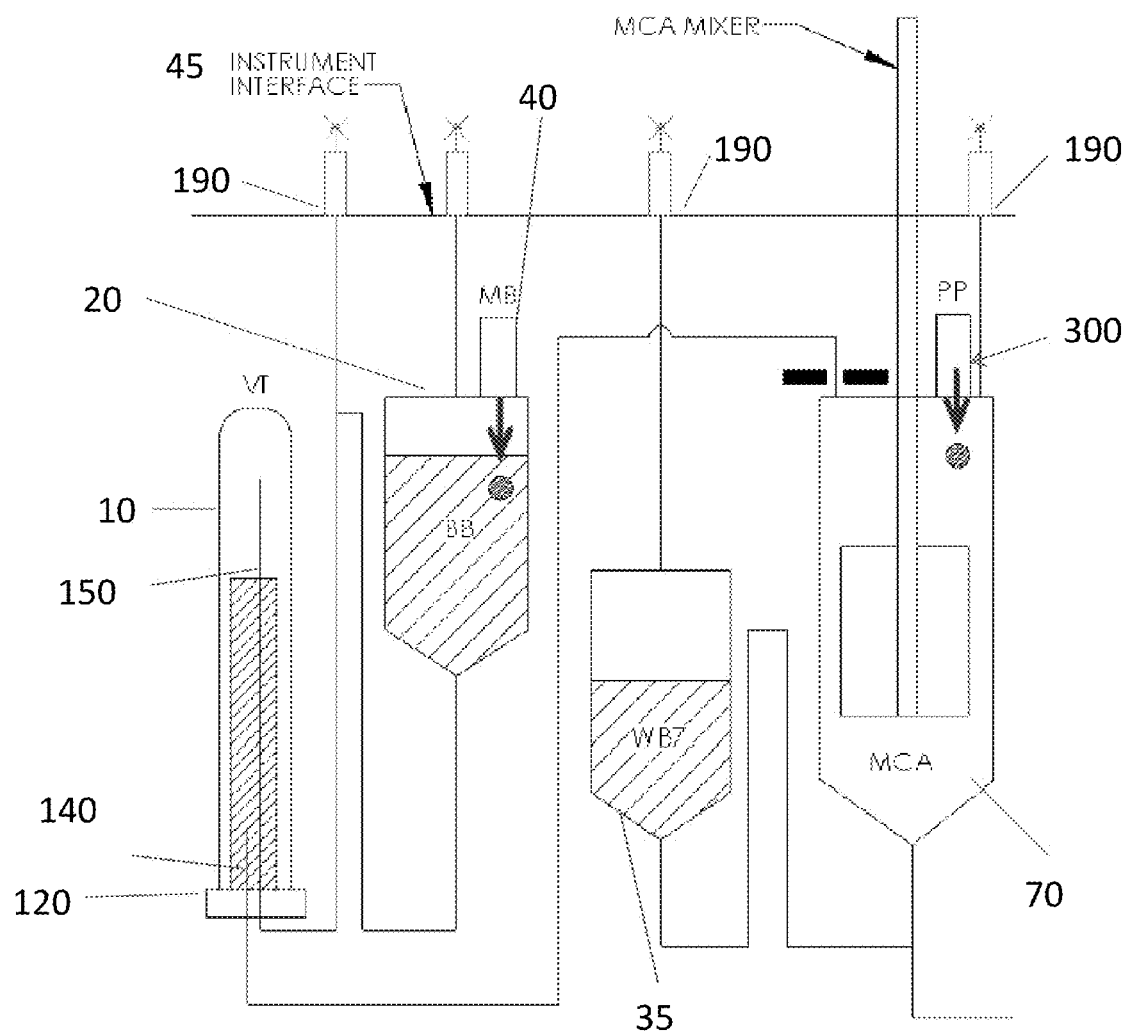

As shown in FIG. 8, a vessel 10 coupled to and in fluidic and pneumatic communication with the cartridge 100 via the output member 150 and input member 140. The vessel 10 is an enclosed collection tube containing a sample. In one embodiment, vessel contains 10 to 15 mL of blood. The cartridge 100 is placed within an instrument and connected to the instrument's 200 drive mechanism at the instrument interface 45 through interface ports 190. Once the vessel 10 is in communication with the cartridge 100, the user can activate the instrument to initiate the target capture process. The instrument 200 activates and empties a chamber containing magnetic particles 40 into a particle buffer reservoir 20. Each of the magnetic particles is conjugated to a moiety specific to at least one target. As discussed above, the plurality of magnetic particles in the chamber 40 may include different sets of magnetic particles in which each set is conjugated to capture moiety specific to a different target of interest (e.g. for multiplex capture of targets). The chamber containing magnetic particles 40 is typically a glass ampoule. A piston located on the instrument can apply pressure to the particle chamber 40 causing it to release the particles into the buffer reservoir 20. Alternatively and as shown in FIG. 2, the chamber containing the magnetic particles 40 is located between the buffer reservoir 20 and the vessel 10. In this configuration, the drive mechanism forces the buffer towards the particle chamber 40 with enough pressure to cause the buffer to break a seal on the particle chamber 40 and introduce the buffer into the particle chamber 40. In either embodiment, the result is having the buffer and particles in the same chamber/reservoir. Typically, the buffer/particle mixture is present in a 2:1 ratio to the initial volume of sample (e.g. buffer/particle mixture is about 20 mL to 30 mL for a sample of 10 mL to 15 mL). Any buffer suitable for promoting binding of magnetic particles (having binding moieties specific to targets) to targets is suitable for use in the cartridge 100. Once in the same chamber, a bubble can be introduced to ensure the magnetic particles are fully submersed in the buffer.

Figure 9:
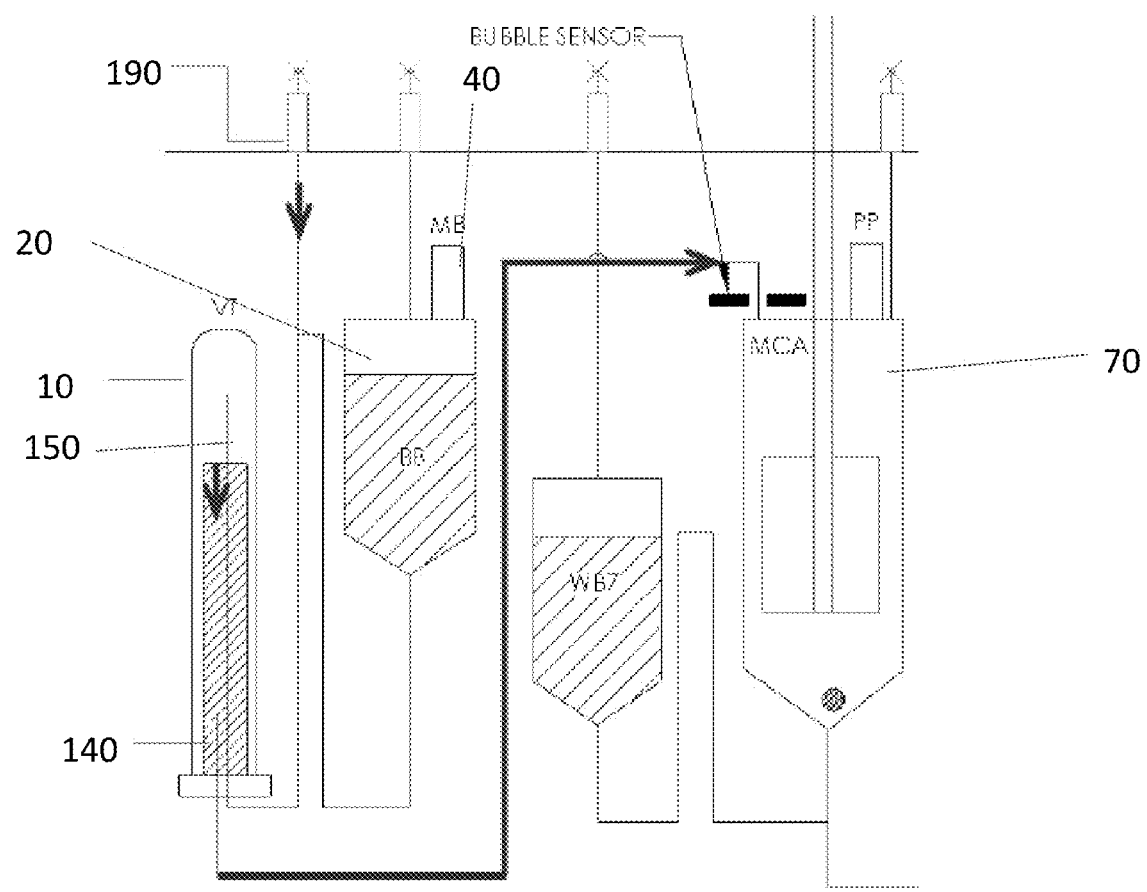

As shown in FIG. 9, prior to introducing the particle/buffer solution into the vessel, the drive mechanism of the instrument forces air into the vessel through output member 150. The air pressure causes at least a portion of the sample to flow through the input member 140 and into the cartridge 100. Within the cartridge 100, the sample is driven through a channel towards the mixing chamber 70. A bubble sensor prior to the inlet of the mixing chamber 70 and air displacement sensor monitor the amount of fluid flowing from the vessel to the mixing chamber 70. The instrument can alert an operator if the desired volume of fluid transferred is not as suspected. In certain embodiments, the drive mechanism forces the entire sample out of the vessel 10 and into the cartridge 100 prior to introducing the buffer/particle mixture into the vessel 10. Alternatively, the drive mechanism transfers none or a portion of the sample into the cartridge 100 prior to introducing the buffer/particle mixture into the vessel 10. In the addition, the step of introducing the particle/buffer mixture into the vessel 10 can be substantially concurrent with the step of transferring the sample and/or sample/particle/buffer mixture into the cartridge 100.

Figure 10:
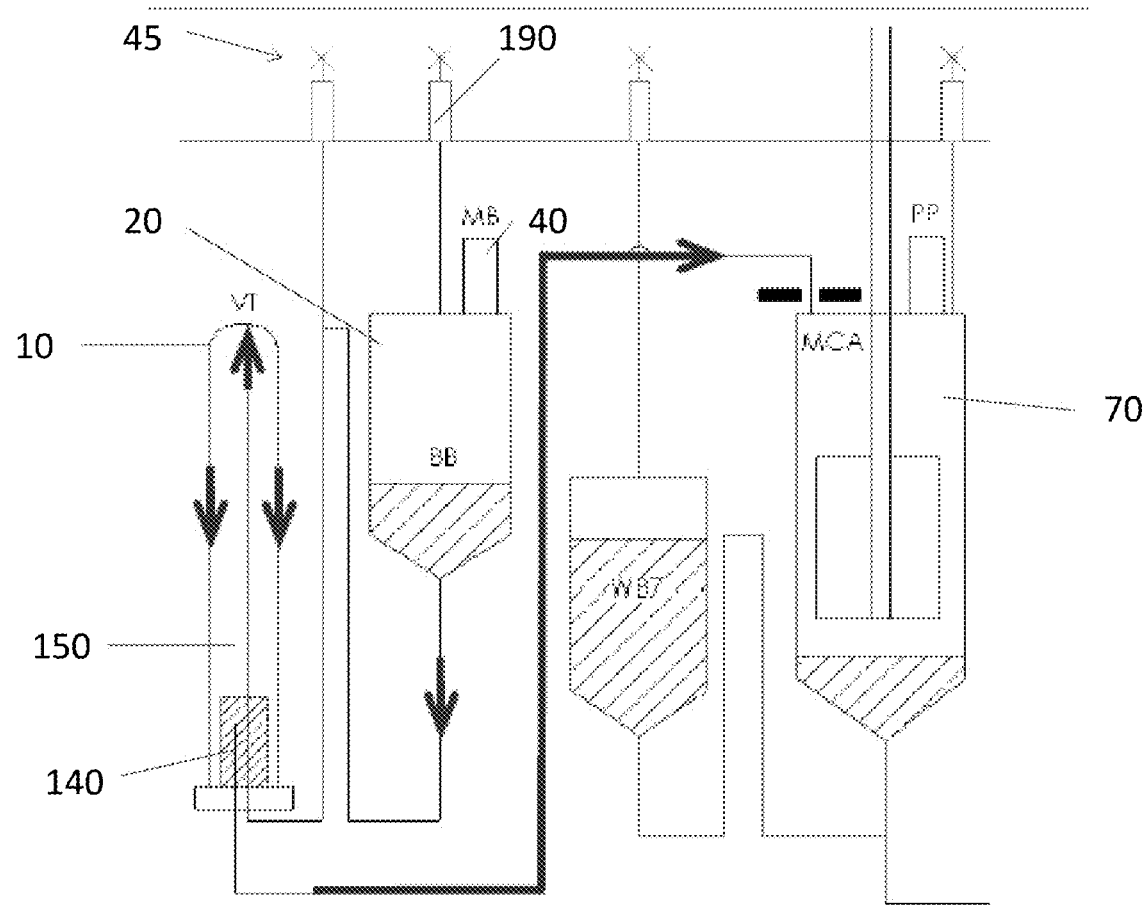

In FIG. 10, the buffer/particle mixture is transferred out of the particle buffer reservoir 20 and into the vessel 10 through output member 150 via air pressure from the drive mechanism. The buffer/particle mixture is transported into the vessel 10 with sufficient force to hit the top of the vessel 10 so that the buffer/particle mixture rinses down the sides of the vessel 10. This ensures any sample collected on the sides of the vessel 10 is introduced into the cartridge 100 through the input member 10. The sample/particle/buffer mixture is driven into the cartridge 100 through input member 140. In one embodiment, after substantially the entire sample and/or particles have been transferred into the cartridge, buffer is still introduced in to the cartridge to conduct an additional rinse. In certain embodiments, after transfer of the buffer into the vessel and draining of buffer/sample/particle mixture into the cartridge, the drive mechanism continues to force air into the vessel 10 to ensure any residual fluid is moved into cartridge 100. The process depicted in FIG. 10 increases the amount of initial sample that is introduced into the cartridge for processing. Because pathogens are often present in levels as 1 CFU/mL, the ability to transfer all of the initial sample fluid into the cartridge advantageously prevents the chance that sample containing the pathogen would remain in the vessel.

Figure 11:
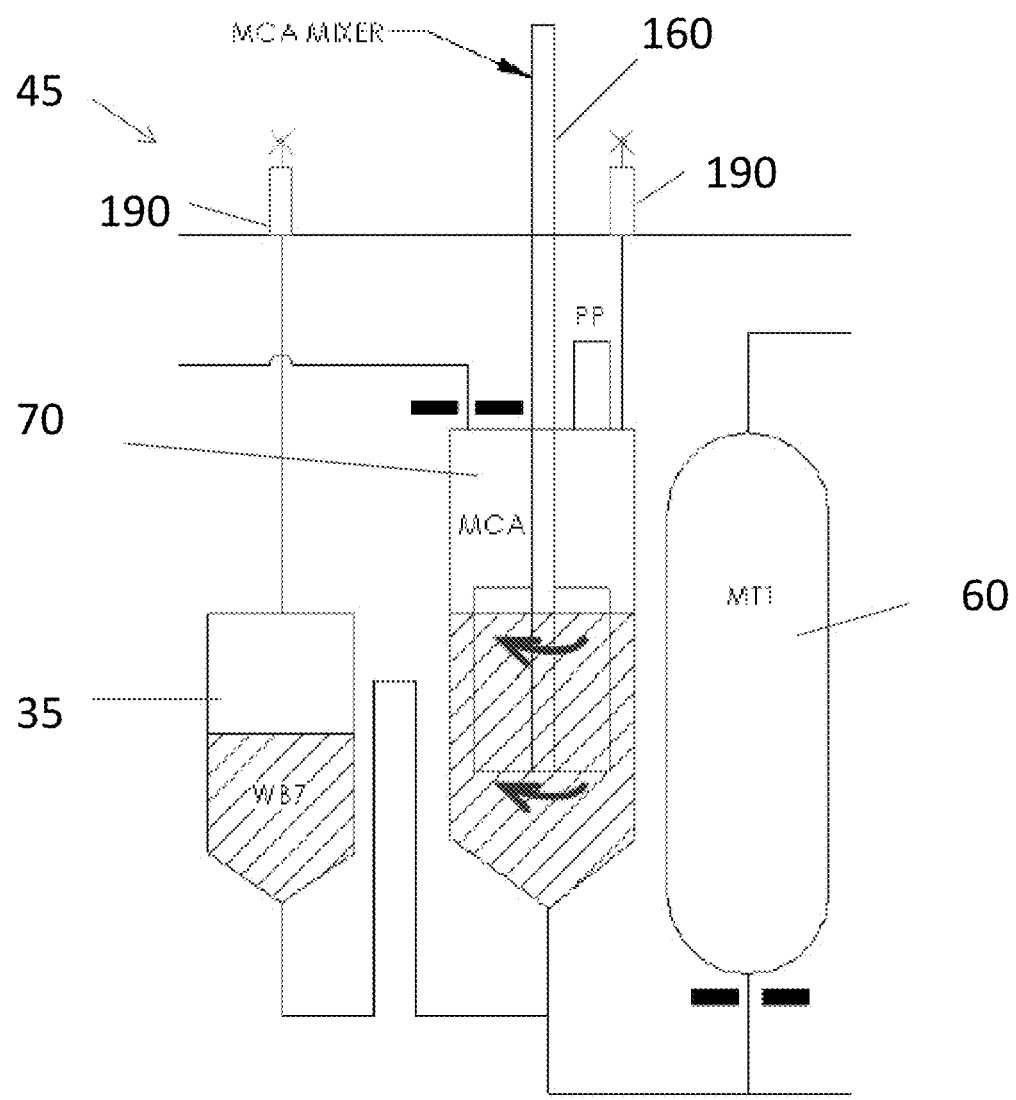

Once the sample/particle/buffer mixture is transferred from the vessel 10 to the mixing chamber 70 as shown in FIG. 11, the mixture is agitated and incubated in the mixing chamber 70. For agitation, the instrument 200 rotates the mixer paddle 170. In one embodiment, the instrument 200 heats the mixing chamber 70 to a temperature ideal for promoting binding of the magnetic particles and any targets present within the sample. The incubation/agitation process is to form target/particle complexes within the fluid. A temperature sensor can be included in the mixing chamber 70 to monitor temperature. The amount of time the sample/particle/buffer mixture is in the mixing chamber 70 can depend on a variety of factors. For example, incubation and agitation time will depend on the desired degree of binding between the pathogen and the compositions of the invention (e.g., the amount of moment that would be desirably attached to the pathogen), the amount of moment per target, the amount of time of mixing, the type of mixing, the reagents present to promote the binding and the binding chemistry system that is being employed. Incubation time can be anywhere from about 5 seconds to a few days. Exemplary incubation times range from about 10 seconds to about 2 hours. Binding occurs over a wide range of temperatures, generally between 15° C. and 40° C.

Figure 12:
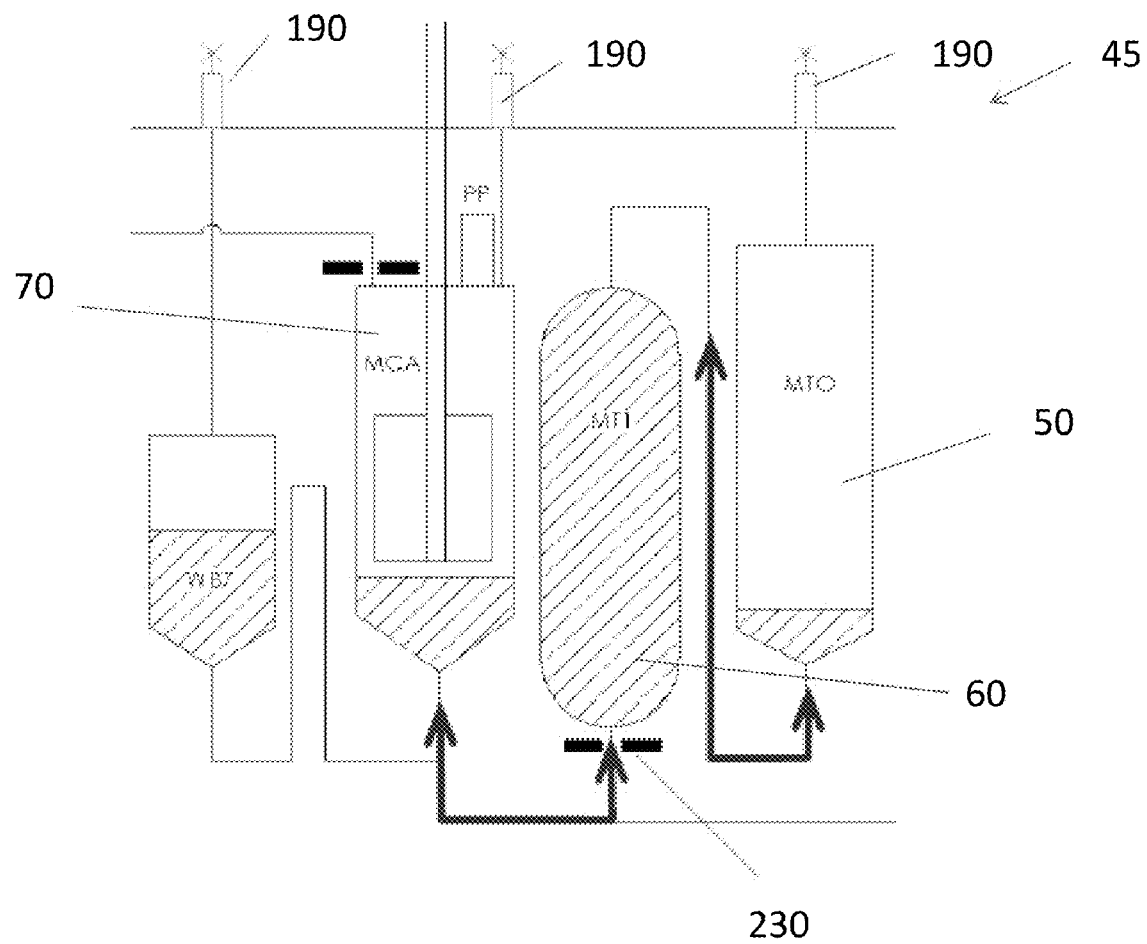

After incubation/agitation, the sample/particle/buffer mixture is cycled through the first magnetic trap 60, as shown in FIG. 12. During the cycling process, a magnetic assembly of the instrument engages with the first magnetic trap 60 to generate a magnetic field that captures the magnetic particles from the mixture cycled there through on a surface of the first magnetic trap 60. In one embodiment, the magnetic trap 60 has a flow path cross-section of 0.5 mm×20 mm (h×w) and the magnetic assembly is an array of bar NdFeB magnets positioned perpendicular to the flow of fluid into the magnetic trap. For cycling, the drive mechanism uses air pressure to force the sample/particle/buffer mixture from the mixing chamber 70 through the first magnetic trap 60 and to the first magnetic trap overflow chamber 50. Once the fluid is passed through the magnetic trap 60 and into the overflow chamber 50, the fluid is then moved back through the first magnetic trap 60 and into the mixing chamber 70. The fluid can be cycled back and forth between the mixing chamber 70 and overflow chamber 50 multiple times and at different flow rates to ensure all magnetic particles are captured. In one embodiment, a bubble sensor 230 associated with the first magnetic trap is used to detect when fluid entering or exiting the magnetic trap is replaced with air. This alerts the instrument 200 that the fluid from the mixing chamber 70 has substantially transferred through the first magnetic trap 60 and into the magnetic trap overflow chamber 50. Once alerted, the fluid is moved back through the first magnetic trap 60. The bubble sensor 230 can be placed at the entrance of the first magnetic trap 60 (as shown in FIG. 12) or at the exit of the first magnetic trap. As an alternative to the bubble sensor, the cycling of fluid can be time controlled.

After the final cycle of fluid through the first magnetic trap 60, the remaining fluid (sample/buffer) separated from the captured magnetic particles is moved into the mixing chamber 70 and stored as waste. Alternatively, the remaining fluid can be transferred to a designated waste chamber.

Figure 13:
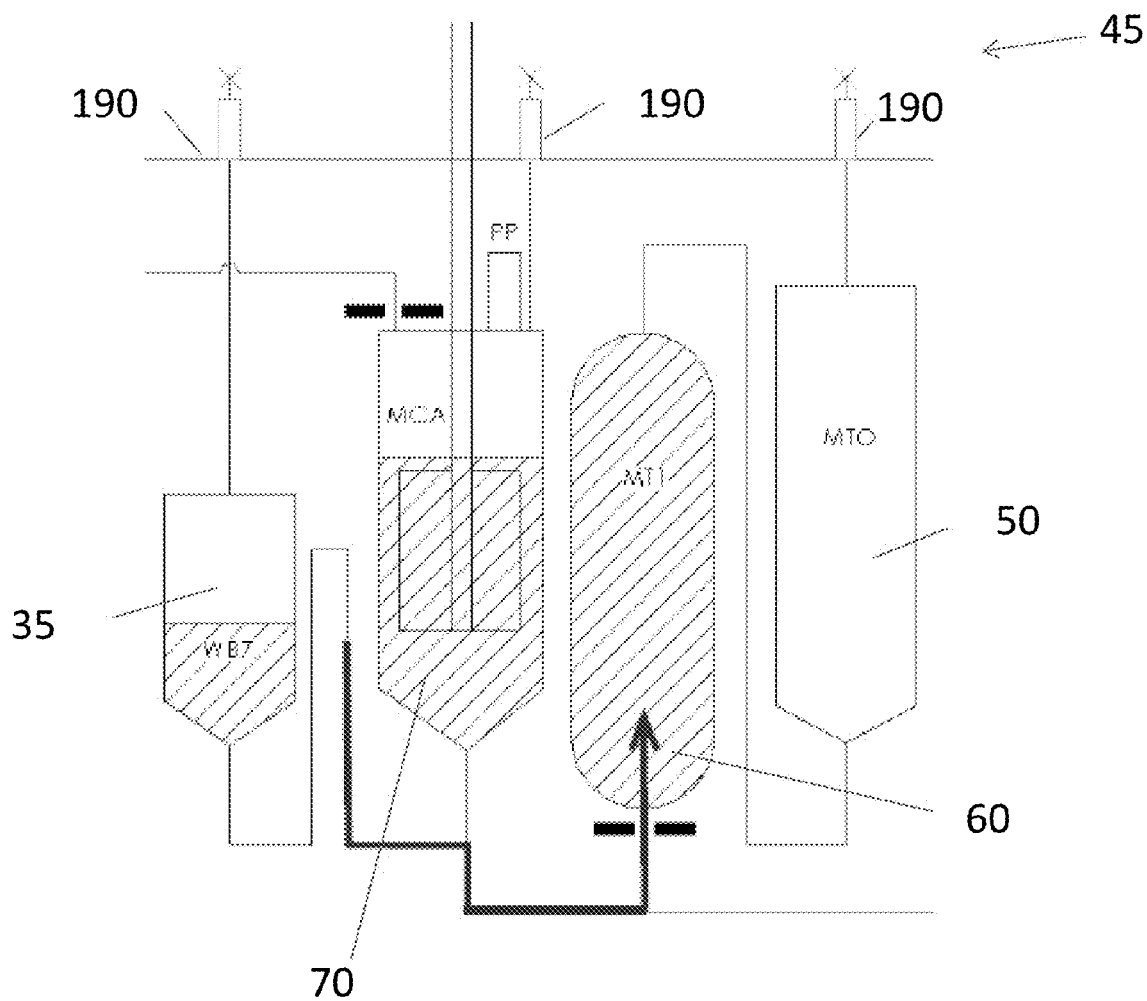
Figure 14:
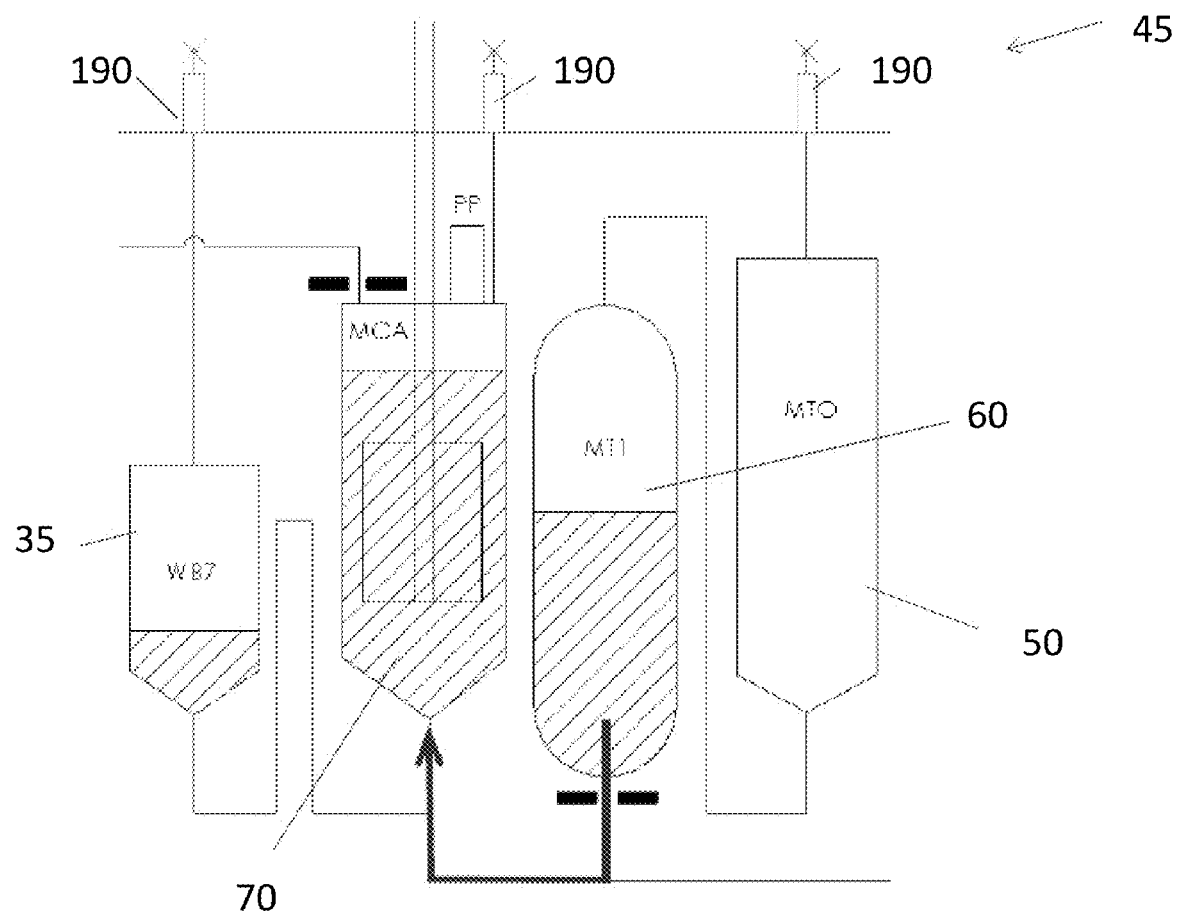

The captured particles within the first magnetic trap 60 are then subject to a wash process as shown in FIG. 13. During the wash process, the magnetic assembly is still engaged with the first magnetic trap 60. A wash solution from wash solution reservoir 35 is transferred into the first magnetic trap 60 until the first magnetic trap 60 is filled. As shown in FIG. 14, the wash solution is then moved out of the first magnetic trap 60, thereby washing/rinsing the particles captured on the surface of the first magnetic trap 60. The wash solution can be moved into the mixing chamber 70 and stored as waste or into a designated waste chamber. Pressure can used to avoid back flow of fluid into the first magnetic trap 60.

Figure 15:
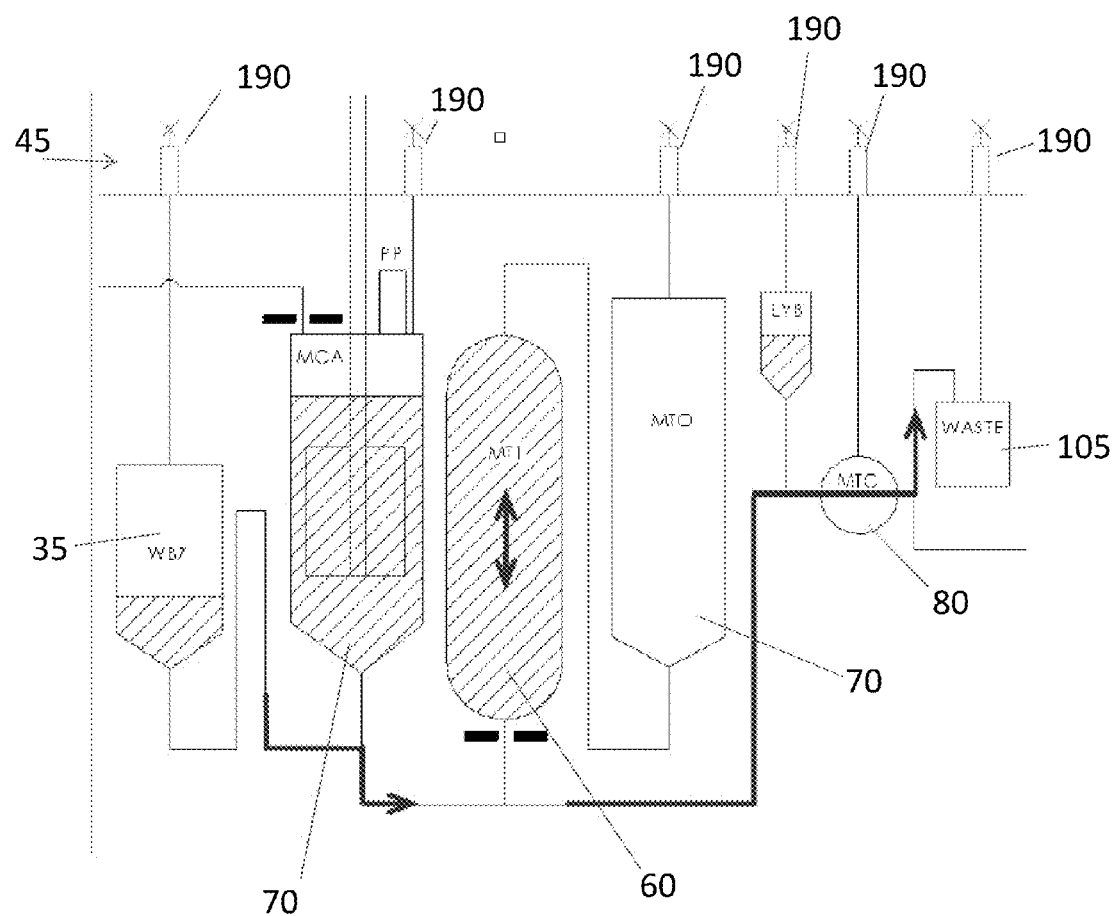

As shown in FIG. 15, the first magnetic trap 60 is further rinsed to suspend captured particles in a fluid and to move the magnetic particles into the second magnetic trap 80. The drive mechanism moves additional wash solution into the first magnetic trap 60, in which one opening of the magnetic trap is closed to prevent flow through. During introduction of wash solution to the first magnetic trap, the magnetic particles are released from the surface and suspended in the wash solution. To remove the magnetic particles from the surface of the first magnetic trap 60, the magnetic assembly is removed from against the first magnetic trap 60 or the magnetic assembly is no longer energized. In one embodiment, a swiper magnet engages an opposite side of the first magnetic trap 60 to encourage the particles to re-suspend. The fluid with the particles from the first magnetic trap 60 is then transported into the second magnetic trap 80. The second magnetic trap 80 is a flow through chamber. Prior to transfer of particles through the second magnetic trap 80, a magnetic assembly engages with the second magnetic trap 80. This magnetic assembly can be the same as or different from the magnetic assembly that engaged with the first magnetic trap 60. In one embodiment, the magnetic assembly is different and includes one or more magnets that emit a magnetic field capable of isolating the quantity of magnetic particles transferred from the first magnetic trap 60 within the second magnetic trap 80 having a microfluidic volume. For example, a second magnetic trap 80 having a volume 500 μL can engage with a magnet having a magnetic flux of 0.6 T and a magnetic gradient of 150 T/m to isolate about 1000 particles (assuming 1000 particles were initially introduced into the sample, processed through the first magnetic trap 60, and transferred to the second magnetic trap 80).

The second magnetic trap 80, as engaged with the magnetic assembly, captures magnetic particles as the fluid flows from the first magnetic trap 60 through the second magnetic trap 80 and into a waste chamber 105. Pressure from the drive mechanism is applied to ensure all the fluid/magnetic particles are transferred into the magnetic trap and to prevent any fluid back flow. The rate of the fluid flow can be controlled to ensure all magnetic particles are capture while the fluid flows through the second magnetic trap 80. In one embodiment, the rate of fluid flow is 1 mL/min. In one aspect, the second magnetic trap 80 has a significantly smaller volume than the first magnetic trap 60 which allows the second magnetic trap 80 to concentrate the substantially the entire quantity of particles initially introduced into the sample into a small volume of fluid. The high concentration of particles in a small volume of fluid provides for easier downstream analysis of or processes performed on targets bound to those particles. That is, the target capture system is able to isolate the clinically relevant portion of a macrofluidic fluid volume in a microfluidic fluid volume. In one embodiment, the first magnetic trap 80 is macrofluidic (volume capacity above 1 mL) and the second magnetic trap is microfluidic (volume capacity below 1000 μL). For example, the first magnetic trap 60 has a macrofluidic volume for processing 30 mL of fluid to initially capture magnetic particles disposed within the 30 mL of fluid and the second magnetic trap 80 has a microfluidic volume of 500 μL of less.

Figure 16:
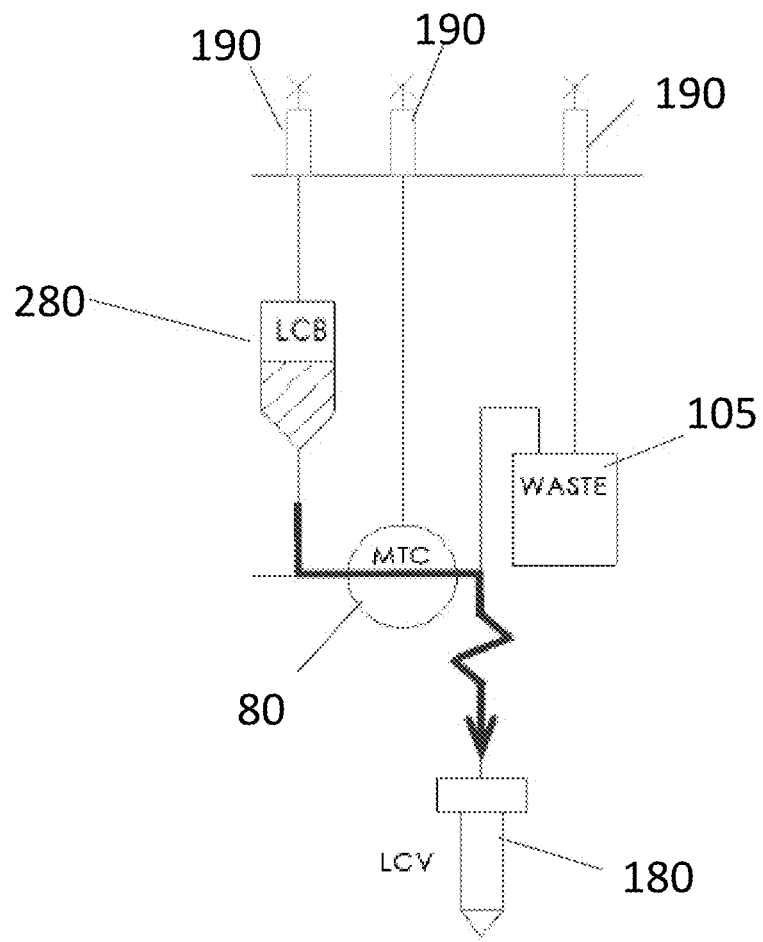

After the magnetic particles are concentrated in the second magnetic trap 80, the captured particles can be directed to a capture vial or subject to further processing. FIG. 16 shows the transfer of the captured particles from the second magnetic trap 80 to the capture vial 170. For transfer to the capture vial 170, the magnet assembly is disengaged from the second magnetic trap 80. Then, a target culture buffer from a reservoir 280 flushes the contents of the second magnetic trap 80 into the capture vial 170. This provides for direct capture of the particles and molecules attached thereto. Direct capture of particles from the second magnetic trap 80 can be used to capture whole live cell targets bound to the particles.

Figure 17:
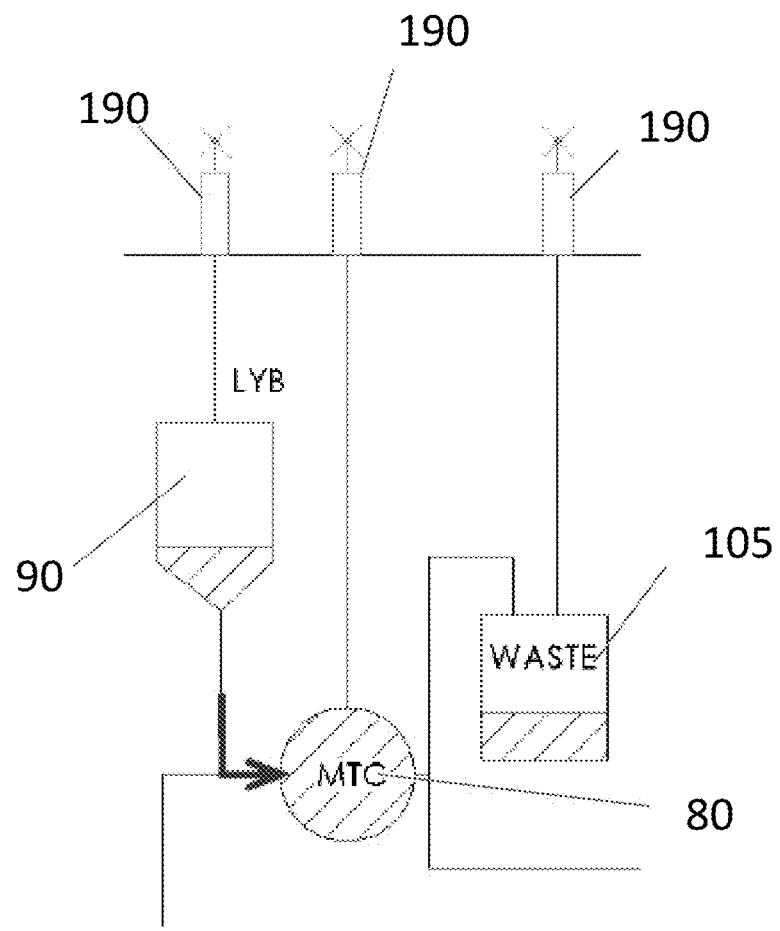

FIGS. 17-22 depict further processing of captured particles to obtain nucleic acids from any targets bound to the captured particles. First, the captured magnetic particles are subject to sonication to invoke cell lysis of target cells bound to the particles. This step allows lysis of target cells in the presence of the magnetic particles without pre-separation of the particles from the target. This step avoids potential loss of targets during the pre-separation step. As shown in FIG. 17, a fluid from reservoir 90 is transferred into the second magnetic trap 80. In one embodiment, the fluid is a lysing buffer or agent. The outlet port of the second magnetic trap 80 is closed to allow the cell lysis buffer to fill the second magnetic trap 80. Once filled, the magnetic assembly is disengaged from the second magnetic trap 80 to suspend the magnetic particles in the buffer. A sonicator probe (such as a VibraCell, sonicator commercially available from Sonics and Materials, Inc.) of the instrument is positioned against a surface of the second magnetic trap 80. In one embodiment, the surface is a formed from a thin film, such as a Mylar film of 125 μM. The sonicator can be activated for different lengths and at different settings to achieve cell lysis. In one embodiment, the cartridge 100 further includes a reservoir of lysis bashing beads that can be transferred into the second magnetic trap 80 to assist with cell lysis.

After lysis by sonication is complete, the lysate can be forced into a pre-column mixer 85 as shown in FIG. 18. A nucleic acid extraction buffer can also be introduced into the pre-column mixer 85 from reservoir 75. The lysate and the extraction buffer are mixed within the pre-column mixer 85. In one embodiment, the pre-column mixer 85 is a bubble mixer and the lysate/extraction buffer mixture is agitated via bubbling air into the mixer 85. FIG. 19 depicts the lysate/extraction buffer mixture is transferred from the pre-column mixer 85 through nucleic acid extraction matrix 110 and into a waste chamber 95. In one embodiment, the nucleic acid extraction matrix 110 is an affinity column. The nucleic acid extraction matrix 110 retains nucleic acids from the lysate/extraction buffer mixture.

Figure 20:
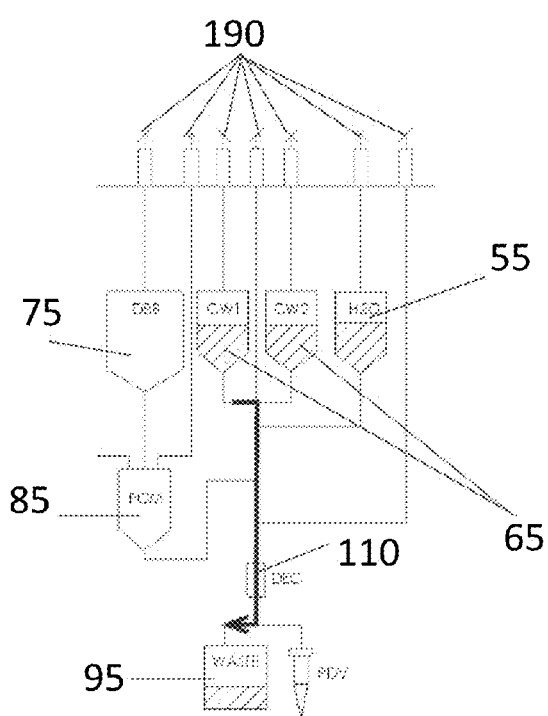
Figure 21:
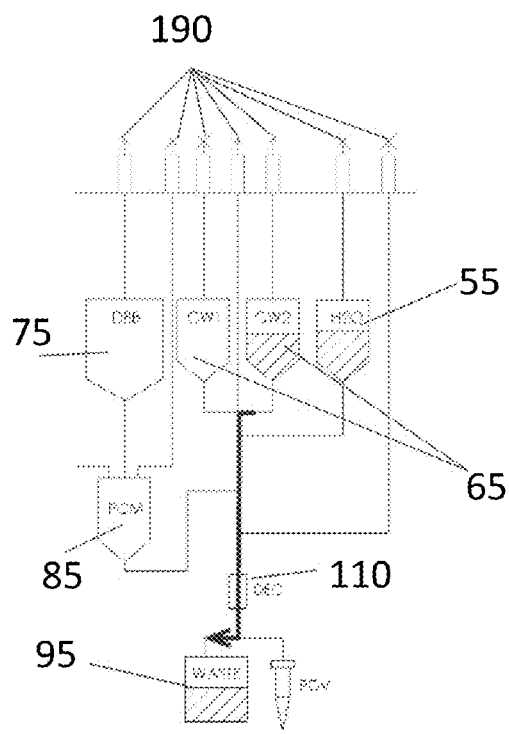
Figure 22:
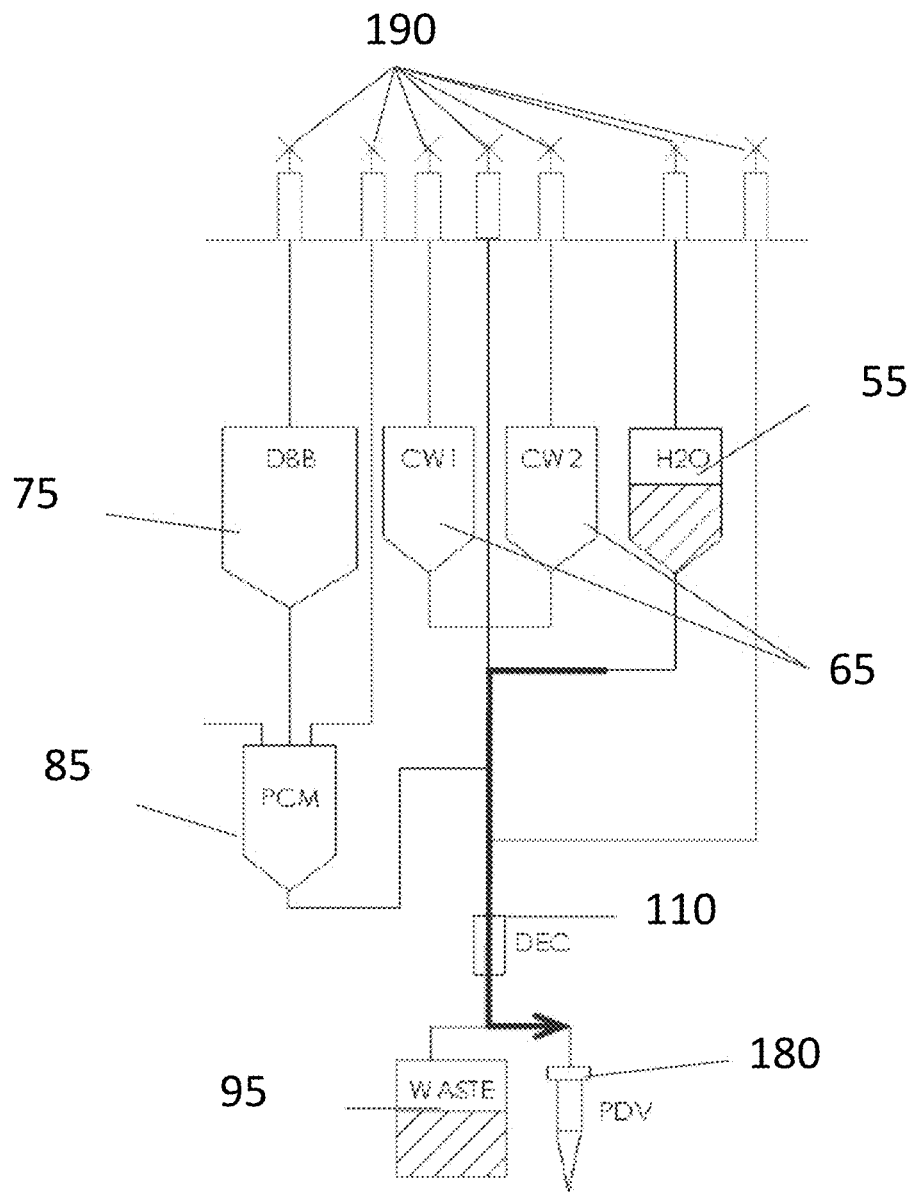

The nucleic acid extraction matrix 110 can then be subject to one or more washes. As shown in FIGS. 20 and 21, the nucleic acid extraction matrix 95 is subject to two washes. Air pressure forces wash buffers from chambers 65 through the nucleic acid extraction member 110 and into waste chamber 95 to remove any unwanted particulates. In one embodiment, any remaining volatiles within the nucleic acid extraction matrix 110 are removed with air pressure from the drive mechanism.

After the washes, the nucleic acid extraction matrix 110 can be eluted with a fluid from the elution reservoir 55. In one embodiment, the fluid is water. The drive mechanism uses high air pressure to force the fluid through the nucleic acid extraction matrix 110 into a nucleic acid capture vial 180 (SEE FIG. 22). This elution step transfers extracted nucleic acids into the vial. The capture vial 180 can be removed from the cartridge by the operator and subject to further analysis. In certain embodiments, the capture vial 180 may include one or more components required for subsequent analysis of the extracted nucleic acids. For example, the one or more components may include primer/probe sets for real-time PCR quantification. Preferably, the one or more components for subsequent analysis of the extracted nucleic acids are specific to same pathogens that the magnetic particles were designed to capture.

Detection of Target Cell or Detection of Nucleic Acids

In particular embodiments, the isolated targets or the extracted nucleic acid from the captured targets, as isolated with the target capture system, may be analyzed by a multitude of technologies. These technologies include, for example, miniature NMR, Polymerase Chain Reaction (PCR), mass spectrometry, fluorescent labeling and visualization using microscopic observation, fluorescent in situ hybridization (FISH), growth-based antibiotic sensitivity tests, and variety of other methods that may be conducted with purified target without significant contamination from other sample components.

In one embodiment, isolated bacteria are eluted from the magnetic particles and are lysed with a chaotropic solution, and DNA is bound to DNA extraction resin. After washing of the resin, the bacterial DNA is eluted and used in quantitative RT-PCR to detect the presence of a specific species, and/or, subclasses of bacteria.

In another embodiment, captured bacteria is removed from the magnetic particles to which they are bound and the processed sample is mixed with fluorescent labeled antibodies specific to the bacteria or fluorescent Gram stain. After incubation, the reaction mixture is filtered through 0.2 μm to 1.0 μm filter to capture labeled bacteria while allowing majority of free particles and fluorescent labels to pass through the filter. Bacteria is visualized on the filter using microscopic techniques, e.g. direct microscopic observation, laser scanning or other automated methods of image capture. The presence of bacteria is detected through image analysis. After the positive detection by visual techniques, the bacteria can be further characterized using PCR or genomic methods.

Detection of bacteria of interest can be performed by use of nucleic acid probes following procedures which are known in the art. Suitable procedures for detection of bacteria using nucleic acid probes are described, for example, in Stackebrandt et al. (U.S. Pat. No. 5,089,386), King et al. (WO 90/08841), Foster et al. (WO 92/15883), and Cossart et al. (WO 89/06699), each of which is hereby incorporated by reference.

A suitable nucleic acid probe assay generally includes sample treatment and lysis, hybridization with selected probe(s), hybrid capture, and detection. Lysis of the bacteria is necessary to release the nucleic acid for the probes. The nucleic acid target molecules are released by treatment with any of a number of lysis agents, including alkali (such as NaOH), guanidine salts (such as guanidine thiocyanate), enzymes (such as lysozyme, mutanolysin and proteinase K), and detergents. Lysis of the bacteria, therefore, releases both DNA and RNA, particularly ribosomal RNA and chromosomal DNA both of which can be utilized as the target molecules with appropriate selection of a suitable probe. Use of rRNA as the target molecule(s), may be advantageous because rRNAs constitute a significant component of cellular mass, thereby providing an abundance of target molecules. The use of rRNA probes also enhances specificity for the bacteria of interest, that is, positive detection without undesirable cross-reactivity which can lead to false positives or false detection.

Hybridization includes addition of the specific nucleic acid probes. In general, hybridization is the procedure by which two partially or completely complementary nucleic acids are combined, under defined reaction conditions, in an anti-parallel fashion to form specific and stable hydrogen bonds. The selection or stringency of the hybridization/reaction conditions is defined by the length and base composition of the probe/target duplex, as well as by the level and geometry of mis-pairing between the two nucleic acid strands. Stringency is also governed by such reaction parameters as temperature, types and concentrations of denaturing agents present and the type and concentration of ionic species present in the hybridization solution.

The hybridization phase of the nucleic acid probe assay is performed with a single selected probe or with a combination of two, three or more probes. Probes are selected having sequences which are homologous to unique nucleic acid sequences of the target organism. In general, a first capture probe is utilized to capture formed hybrid molecules. The hybrid molecule is then detected by use of antibody reaction or by use of a second detector probe which may be labelled with a radioisotope (such as phosphorus-32) or a fluorescent label (such as fluorescein) or chemiluminescent label.

Detection of pathogen of interest can also be performed by use of PCR techniques. A suitable PCR technique is described, for example, in Verhoef et al. (WO 92/08805). Such protocols may be applied directly to the pathogen captured on the magnetic particles. The pathogen is combined with a lysis buffer and collected nucleic acid target molecules are then utilized as the template for the PCR reaction.

In certain embodiments, nucleic acids derived from the captured pathogen are analyzed in a multiplex reaction in order to rapidly detect two or more pathogens present in the sample. Any multiplex reaction known in the art may be used, such as multiplex ELISA, multiplex sequencing, multiplex probe hybridization, etc. In certain embodiments, multiplex reactions may involve the amplification and quantification of two or more targets in the same reaction volume. Typical multiplex reactions involve PCR, qPCR (real-time PCR), and sequencing.

Multiplex PCR refers to the use of more than one primer pair in a single reaction vessel in order to amplify more than one target sequence. In the case of real-time PCR, more than one primer pair/probe set is utilized. Multiplex PCR allows for simultaneous detection of different targets in the same reaction. The target sequences may be identified by an identifiable label (e.g. fluorescent probe) or by subsequent sequencing. Multiplex real-time PCR uses multiple probe-based assays, in which each assay has a specific probe labeled with a unique fluorescent dye, resulting in different observed colors for each assay. Real-time PCR instruments can discriminate between the fluorescence generated from different dyes. Different probes are labeled with different dyes that each have unique emission spectra. Spectral signals are collected with discrete optics, passed through a series of filter sets, and collected by an array of detectors. Spectral overlap between dyes is corrected by using pure dye spectra to deconvolute the experimental data by matrix algebra. An overview of real-time PCR techniques is described in detail in Elnifro, Elfath M., et al. "Multiplex PCR: optimization and application in diagnostic virology." Clinical Microbiology Reviews 13.4 (2000): 559-570. Multiplex PCR reaction techniques are described in U.S. Publication Nos. 20130059762, and 2005/0026144 as well as Carroll, N. M., E. E. Jaeger, et al. (2000). "Detection of and discrimination between gram-positive and gram-negative bacteria in intraocular samples by using nested PCR." J Clin Microbiol 38(5): 1753-1757, and Klaschik, S., L. E. Lehmann, et al. (2002). "Real-time PCR for detection and differentiation of gram-positive and gram-negative bacteria." J Clin Microbiol 40(11): 4304-4307.

Multiplex sequencing involves the simultaneous sequencing of multiple target sequences in a single sequencing run. Multiplex sequencing allows for differentiation between target sequences of different pathogens in a sample and differentiation between nucleic acid sequences of pooled samples (e.g. differentiate between two or more patient samples). In order to differentiate between target sequences, one or more different barcodes may be introduced to the nucleic acid of a sample. Early multiplex sequencing is described in more detail in G. M. Church in U.S. Pat. No. 4,942,124 and further by G. M. Church and S. Kieffer-Higgins in U.S. Pat. No. 5,149,625. Multiplex sequencing of multiple samples involves sequencing of a plurality of template nucleic acid molecules from different samples at the same time on the same platform by attaching a unique oligonucleotide sequence (i.e., a bar code) to the template nucleic acid molecules from different samples prior to pooling and sequencing of the template molecules. The bar code allows for template nucleic acid sequences from different samples to be differentiated from each other. Once bar coded, template molecules from different samples may be pooled and sequenced at the same time on the same platform. Because the bar code on each template molecule is sequenced as part of the sequencing reaction, the bar code is a component of the sequence data, and thus the sequence data for different samples is always associated with the sample from which it originated. Due to the association in the sequence data, the sequence data from the pooled samples may be separated after sequencing has occurred and correlated back to the sample from which it originated.

Any sequencing technique (for singleplex and multiplex assays) may be utilized to identify isolated pathogens by their nucleic acid extracts. Suitable sequencing techniques include, for example, classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

For detection of the selected pathogen by use of antibodies, isolated pathogen are contacted with antibodies specific to the pathogen of interest. As noted above, either polyclonal or monoclonal antibodies can be utilized, but in either case have affinity for the particular pathogen to be detected. These antibodies, will adhere/bind to material from the specific target pathogen. With respect to labeling of the antibodies, these are labeled either directly or indirectly with labels used in other known immunoassays. Direct labels may include fluorescent, chemiluminescent, bioluminescent, radioactive, metallic, biotin or enzymatic molecules. Methods of combining these labels to antibodies or other macromolecules are well known to those in the art. Examples include the methods of Hijmans, W. et al. (1969), Clin. Exp. Immunol. 4, 457-, for fluorescein isothiocyanate, the method of Goding, J. W. (1976), J. Immunol. Meth. 13, 215-, for tetramethylrhodamine isothiocyanate, and the method of Ingrall, E. (1980), Meth. in Enzymol. 70, 419-439 for enzymes.

These detector antibodies may also be labeled indirectly. In this case the actual detection molecule is attached to a secondary antibody or other molecule with binding affinity for the anti-bacteria cell surface antibody. If a secondary antibody is used it is preferably a general antibody to a class of antibody (IgG and IgM) from the animal species used to raise the anti-bacteria cell surface antibodies. For example, the second antibody may be conjugated to an enzyme, either alkaline phosphatase or to peroxidase. To detect the label, after the bacteria of interest is contacted with the second antibody and washed, the isolated component of the sample is immersed in a solution containing a chromogenic substrate for either alkaline phosphatase or peroxidase. A chromogenic substrate is a compound that can be cleaved by an enzyme to result in the production of some type of detectable signal which only appears when the substrate is cleaved from the base molecule. The chromogenic substrate is colorless, until it reacts with the enzyme, at which time an intensely colored product is made. Thus, material from the bacteria colonies adhered to the membrane sheet will become an intense blue/purple/black color, or brown/red while material from other colonies will remain colorless. Examples of detection molecules include fluorescent substances, such as 4-methylumbelliferyl phosphate, and chromogenic substances, such as 4-nitrophenylphosphate, 3,3', 5,5'-tetramethylbenzidine and 2,2'-azino-di-[3-ethelbenzthiazoliane sulfonate (6)]. In addition to alkaline phosphatase and peroxidase, other useful enzymes include β-galactosidase, β-glucuronidase, α-glucosidase, β-glucosidase, α-mannosidase, galactose oxidase, glucose oxidase and hexokinase.

Detection of bacteria of interest using NMR may be accomplished as follows. In the use of NMR as a detection methodology, in which a sample is delivered to a detector coil centered in a magnet, the target of interest, such as a magnetically labeled bacterium, may be delivered by a fluid medium, such as a fluid substantially composed of water. In such a case, the magnetically labeled target may go from a region of very low magnetic field to a region of high magnetic field, for example, a field produced by an about 1 to about 2 Tesla magnet. In this manner, the sample may traverse a magnetic gradient, on the way into the magnet and on the way out of the magnet. As may be seen via equations 1 and 2 below, the target may experience a force pulling into the magnet in the direction of sample flow on the way into the magnet, and a force into the magnet in the opposite direction of flow on the way out of the magnet. The target may experience a retaining force trapping the target in the magnet if flow is not sufficient to overcome the gradient force.

$$m \cdot (\nabla B) = F \qquad \text{Equation 1}$$

$$v_t = -F/(6 * p * n * r) \qquad \text{Equation 2}$$

where n is the viscosity, r is the particle diameter, F is the vector force, B is the vector field, and m is the vector moment of the particle The detection method is based on a miniature NMR detector tuned to the magnetic resonance of water. When the sample is magnetically homogenous (no bound targets), the NMR signal from water is clearly detectable and strong. The presence of magnetic material in the detector coil disturbs the magnetic field, resulting in reduction in water signal. One of the primary benefits of this detection method is that there is no magnetic background in biological samples which significantly reduces the requirements for stringency of sample processing. In addition, since the detected signal is generated by water, there is a built-in signal amplification which allows for the detection of a single labeled bacterium. NMR detection is described in further detail in co-pending and co-assigned U.S. application Ser. No. 13/091,506.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for isolating a pathogen from a sample, the method comprising
   removably coupling a vessel comprising a pathogen-containing sample to a cartridge via a cartridge interface that is configured to provide communication between the vessel and the cartridge;
   flowing magnetic particles conjugated to a capture moiety from the cartridge into the vessel to form a mixture;
   flowing the mixture from the vessel into the cartridge;
   flowing a fluid from the cartridge into the vessel to flush residual mixture from the vessel into the cartridge; and
   incubating the mixture in the cartridge to allow the particles to bind to the pathogen;
   applying a magnetic field to capture pathogen/magnetic particle complexes on a surface of a first magnetic trap;
   washing the captured pathogen/magnetic particle complexes with a wash solution, thereby isolating the pathogen/magnetic particle complexes;
   removing the magnetic field;
   re-introducing the wash solution, thereby re-suspending the pathogen/magnetic particle complexes;
   flowing the re-suspended pathogen/magnetic particle complexes through a channel and into a second magnetic trap; and
   engaging the second magnetic trap, thereby re-capturing the pathogen/magnetic particle complexes;
   wherein the first magnetic trap is configured to capture the pathogen/magnetic particle complexes from a macro-scale volume of fluid, and the second magnetic trap is configured to concentrate substantially all of the pathogen/magnetic particle complexes into a micro-scale volume of fluid.

2. The method of claim 1, further comprising lysing the captured pathogen in a region selected from the group consisting of the first magnetic trap, the second magnetic trap, and a combination thereof.

3. The method of claim 2, further comprising separating nucleic acid from the lysate; and collecting the separated nucleic acid into a vial.

4. The method of claim 3, further comprising analyzing the nucleic acid to thereby identify the pathogen.

5. The method of claim 4, wherein analyzing comprises conducting a sequencing reaction.

6. The method of claim 4, wherein analyzing comprises conducting an amplification reaction.

7. The method of claim 6, wherein the vial comprises at least one detectably labeled nucleic acid probe specific for the pathogen.

8. The method of claim 1, wherein the sample comprises a plurality of pathogen.

9. The method of claim 8, wherein the plurality of magnetic particles are composed of different sets, wherein members of the different sets are conjugated to different capture moieties that are specific for the different pathogen.

10. The method of claim 9, further comprising conducting a multiplex reaction to analyze nucleic acid from the plurality of isolated pathogen and thereby identify the plurality of pathogen.

11. The method of claim 10, wherein the multiplex reaction is a multiplex sequencing reaction.

12. The method of claim 10, wherein the multiplex reaction is a multiplex amplification reaction.

13. The method of claim 1, wherein the capture moiety is a type selected from the group consisting of antibodies, lectins, bacteriophages, antimicrobial agents, oligonucleotides, and combinations thereof.

14. The method of claim 1, wherein the pathogen is selected from the group consisting of fungi, bacteria or both.

15. The method of claim 14, wherein the fungi are selected from the group consisting of the *Candida* genus, the *Aspergillus* genus, the *Cryptococcus* genus, and a combination thereof.

16. The method of claim 14, wherein the bacteria are selected from the group consisting of the *Staphylococcus* genus, the Enterobacteriaceae genus, the *Acinetobacter* genus, the *Stenotrophomas* genus, the *Pseudomonas* genus, the *Neisseria* genus, the *Clostridium* genus, and the *Enterococcus* genus.

17. The method of claim 1, wherein said sample is a human tissue or body fluid.

* * * * *